United States Patent
Cha et al.

(10) Patent No.: US 12,428,429 B2
(45) Date of Patent: Sep. 30, 2025

(54) AMINE COMPOUND AND ORGANIC LIGHT-EMITTING DIODE INCLUDING SAME

(71) Applicant: SFC CO., LTD., Cheongju-si (KR)

(72) Inventors: Soon-Wook Cha, Goyang-si (KR); Sang-Woo Park, Seoul (KR); Yoona Shin, Seoul (KR); Jung-Ho Yoo, Seosan-si (KR); Ji-Hwan Kim, Anyang-si (KR); Sung Woo Kim, Anyang-si (KR)

(73) Assignee: SFC CO., LTD., Cheongju-si (KR)

( * ) Notice: Subject to any disclaimer, the term of this patent is extended or adjusted under 35 U.S.C. 154(b) by 946 days.

(21) Appl. No.: 16/072,223

(22) PCT Filed: Feb. 7, 2017

(86) PCT No.: PCT/KR2017/001339
§ 371 (c)(1),
(2) Date: Jul. 24, 2018

(87) PCT Pub. No.: WO2017/146397
PCT Pub. Date: Aug. 31, 2017

(65) Prior Publication Data
US 2019/0067588 A1    Feb. 28, 2019

(30) Foreign Application Priority Data

Feb. 22, 2016 (KR) .................. 10-1026-0020370

(51) Int. Cl.
| | | |
|---|---|---|
| *C07D 493/04* | (2006.01) | |
| *C07D 307/93* | (2006.01) | |
| *C07D 495/04* | (2006.01) | |
| *C07F 7/08* | (2006.01) | |
| *C09K 11/06* | (2006.01) | |
| *H05B 33/14* | (2006.01) | |
| *H10K 50/11* | (2023.01) | |
| *H10K 50/15* | (2023.01) | |
| *H10K 50/16* | (2023.01) | |
| *H10K 50/17* | (2023.01) | |
| *H10K 59/10* | (2023.01) | |
| *H10K 71/12* | (2023.01) | |
| *H10K 71/16* | (2023.01) | |
| *H10K 85/40* | (2023.01) | |
| *H10K 85/60* | (2023.01) | |

(52) U.S. Cl.
CPC ......... *C07D 493/04* (2013.01); *C07D 307/93* (2013.01); *C07D 495/04* (2013.01); *C07F 7/0812* (2013.01); *C09K 11/06* (2013.01); *H05B 33/14* (2013.01); *H10K 85/40* (2023.02); *H10K 85/636* (2023.02); *H10K 85/6574* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 59/10* (2023.02); *H10K 71/12* (2023.02); *H10K 71/16* (2023.02); *H10K 85/6572* (2023.02)

(58) Field of Classification Search
CPC ............ H01L 51/0061; H01L 51/0073; H01L 51/0094; H01L 51/5012; H01L 51/5056; H01L 51/5072; H01L 51/5088; C07D 307/91; C07D 333/76; C07C 211/16; C07C 211/18; C07F 9/5022; H10K 50/11; H10K 50/15; H10K 50/16; H10K 50/17; H10K 50/171; H10K 85/636; H10K 85/6572; H10K 85/6574; H10K 85/40
See application file for complete search history.

(56) References Cited

U.S. PATENT DOCUMENTS

| | | | | |
|---|---|---|---|---|
| 10,014,479 B2 * | 7/2018 | Kim | .................. | H01L 51/0054 |
| 10,468,603 B2 * | 11/2019 | Cha | .................. | H01L 51/0073 |
| 10,741,768 B2 * | 8/2020 | Lee | .................. | C07D 493/10 |
| 10,790,450 B2 * | 9/2020 | Pyo | .................. | C07D 493/10 |
| 10,797,259 B2 * | 10/2020 | Cha | .................. | H01L 51/006 |
| 10,947,449 B2 * | 3/2021 | Kim | .................. | H10K 85/649 |
| 10,950,802 B2 * | 3/2021 | Park | .................. | H01L 51/0053 |
| 2006/0227081 A1 * | 10/2006 | Joo | .................. | G09G 3/3233 |
| | | | | 345/76 |
| 2016/0351818 A1 * | 12/2016 | Kim | .................. | H01L 51/0052 |
| 2017/0342318 A1 * | 11/2017 | Kim | .................. | H10K 85/631 |

FOREIGN PATENT DOCUMENTS

| | | | | |
|---|---|---|---|---|
| KR | 1020080015865 A | 2/2008 | | |
| KR | 1020120047706 A | 5/2012 | | |
| KR | 1020150130206 A | 11/2015 | | |
| KR | 1020160013678 A | 2/2016 | | |
| WO | WO2015174682 A1 | 11/2015 | | |
| WO | WO-2016108419 A1 * | 7/2016 | ................ | C07F 7/30 |

OTHER PUBLICATIONS

International Search Report of PCT/KR2017/001339, May 17, 2017, English translation.

* cited by examiner

*Primary Examiner* — Dylan C Kershner
(74) *Attorney, Agent, or Firm* — STIP Law Group, LLC

(57) ABSTRACT

The present invention relates to a novel amine compound and an organic light-emitting diode including the same. More particularly, the present disclosure relates to an amine compound that allows for high efficiency and a long lifespan in an organic light-emitting diode if used as an element therein and to an organic light-emitting diode including the same.

11 Claims, 1 Drawing Sheet

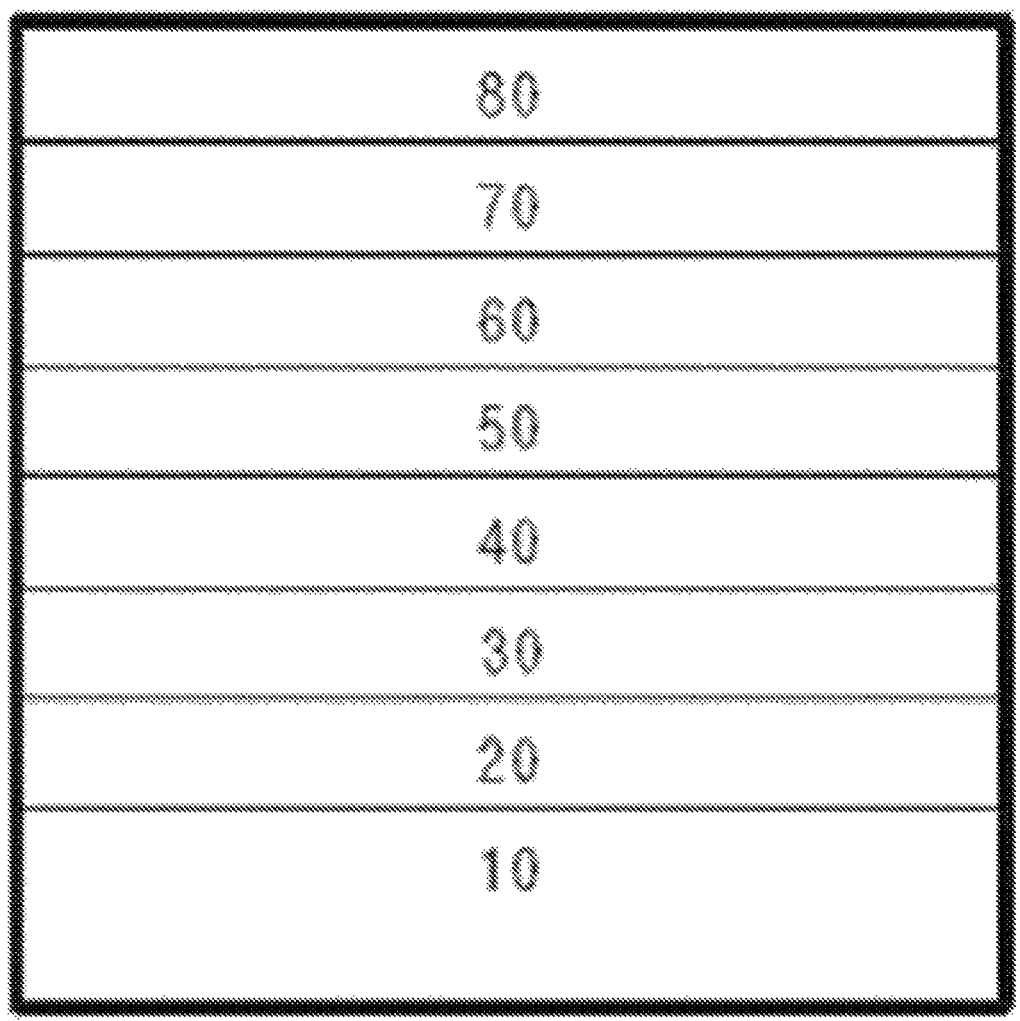

AMINE COMPOUND AND ORGANIC LIGHT-EMITTING DIODE INCLUDING SAME

CROSS-REFERENCE TO RELATED APPLICATIONS

This application is the U.S. National Phase under 35 U.S.C. § 371 of International Application No. PCT/KR2017/001339 filed on Feb. 7, 2017, which in turn claims the benefit of Korean Application No. 10-2016-0020370, filed on Feb. 22, 2016, the disclosures of which are incorporated by reference into the present application.

TECHNICAL FIELD

The present disclosure relates to a novel amine compound and an organic light-emitting diode including the same. More particularly, the present disclosure relates to an amine compound that allows for high efficiency and a long lifespan in an organic light-emitting diode if used as an element therein and to an organic light-emitting diode including the same.

BACKGROUND ART

Organic light-emitting diodes (OLEDs), based on self-luminescence, are used to create digital displays with the advantage of having a wide viewing angle and being able to be made thinner and lighter than liquid crystal displays. In addition, an OLED display exhibits a very fast response time. Accordingly, OLEDs find applications in the full color display field or the illumination field.

Materials used as the organic layers in organic light emitting diodes may be divided into luminescent materials and charge carrier materials, for example, a hole injection material, a hole transport material, an electron injection material, and an electron transport material. According to the luminescent materials, there are two main families of OLED: those based on small molecules and those employing polymers. The light emitting mechanisms allow the luminescent materials to be classified as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emitting efficiency. In this regard, a host-dopant system may be used as a luminescent material so as to increase the color purity and the light emitting efficiency through energy transfer.

This is based on the principle that, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of the dopant because the wavelength of the host moves to a wavelength range of the dopant.

With regard to related arts of dopant compounds in the light-emitting layer, reference may be made to Korean Patent No. 10-2008-0015865 A (Feb. 20, 2008), which describes an organic light emitting device using an arylamine-coupled indenofluorene derivative, and Korean Patent No. 10-2012-0047706 A (May 14, 2012), which describes an organic photoelectric device using a compound in which dibenzofuran or dibenzothiophene coexists with fluorene or carbazole.

A recent study on an organic light-emitting diode exhibiting high efficiency and a long lifespan is found in Korean Patent No. 2015-0130206 (Nov. 23, 2015), which discloses an heterocyclic compound comprising an aromatic amine group and an organic light-emitting diode including the same.

Despite such related arts, there is still a need for research and development of novel compounds for organic light-emitting diodes which provide high efficiency or a long lifespan, compared to organic luminescent materials developed thus far.

DETAILED DESCRIPTION OF THE INVENTION

Technical Problem

Accordingly, a purpose to be accomplished by the present disclosure is to provide a novel amine compound for organic light-emitting diodes (OLEDs) which exhibit high luminescence efficiency.

Another purpose to be accomplished by the present disclosure is to provide an OLED of high luminescence efficiency including the amine compound.

Technical Solution

In order to accomplish the purposes, the present disclosure provides an amine compound represented by the following Chemical Formula A:

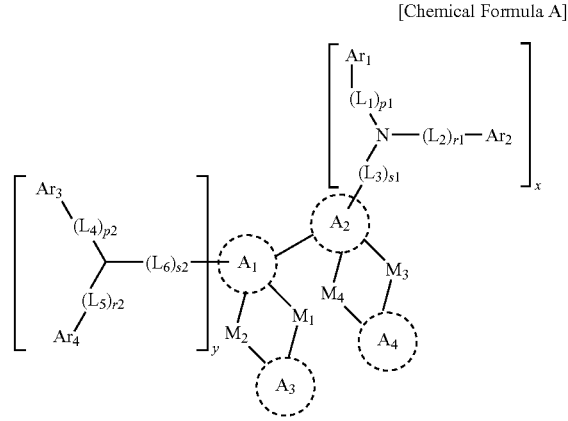

[Chemical Formula A]

wherein, $A_1$, $A_2$, $A_3$, and $A_4$ may be the same or different and are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of $A_1$ and two adjacent carbon atoms within the aromatic ring of $A_2$ form a 5-membered ring with a carbon atom connected to both substituents $R_1$ and $R_2$, thus establishing a fused ring structure;

two adjacent carbon atoms within the aromatic ring of $A_1$, which do not participate in forming the 5-membered ring with the carbon atom connected to both substituents $R_1$ and $R_2$, are linked to $M_1$ and $M_2$, respectively, in order to form a 5-membered, fused ring, two adjacent carbon atoms within the aromatic ring of $A_2$, which do not participate in forming the 5-membered ring with the carbon atom connected to both substituents $R_1$ and $R_2$, are linked to $M_3$ and $M_4$, respectively, in order to form a 5-membered, fused ring, two adjacent carbon atoms within the aromatic ring of $A_3$ are linked to $M_1$ and $M_2$, respectively, in order to form a 5-membered, fused ring, and two adjacent carbon atoms within the aromatic ring of $A_4$ are linked to $M_3$ and $M_4$, respectively, in order to form a 5-membered, fused ring;

linkers $L_1$ to $L_6$ may be the same or different and are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

at least one of the aromatic rings of $A_1$ to $A_4$ has one to four substituents selected from among a substituted or unsubstituted alkyl of 1 to 30 carbon atoms, a substituted or unsubstituted cycloalkyl of 1 to 30 carbon atoms, a substituted or unsubstituted aryl of 6 to 50 carbon atoms, and a halogen selected from F, Cl, Br, and I;

$M_1$ to $M_4$ may be the same or different and are each independently a single bond, O, S, $CR_3R_4$, $SiR_3R_4$, $GeR_3R_4$, Se, $PR_3$, $BR_3$, or $P(=O)R_3$, with a proviso that one of $M_1$ and $M_2$ is a single bond, and one of $M_3$ and $M_4$ is a single bond;

substituents $R_1$ to $R_4$ and $Ar_1$ to $Ar_4$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 5 to 30 carbon atoms, a substituted or unsubstituted alkyl amine of 1 to 30 carbon atoms, a substituted or unsubstituted aryl amine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen;

in the alterative for $R_1$ and $R_2$, $R_1$ and $R_2$ may be connected to each other to form a mono- or polycyclic aliphatic or aromatic ring which may bear at least one heteroatom selected from among N, O, P, Si, S, Ge, Se, and Te as a ring member;

p1 and p2, r1 and r2, and s1 and s2 are each independently an integer of 1 to 3 and when any of them is 2 or greater, the corresponding linkers $L_1$ to $L_6$ may be the same or different;

x is an integer of 1 or 2;

y is an integer of 0 to 3; and in the alternative for $Ar_1$ and $Ar_4$, $Ar_1$ and $Ar_2$ may be connected to each other to form a ring and/or $Ar_3$ and $Ar_4$ may be connected to each other to form a ring, Also, the present disclosure provides an organic light-emitting diode, comprising: a first electrode; a second electrode facing the first electrode; and a light-emitting layer interposed between the first electrode and the second electrode, wherein the light-emitting layer includes at least one of the organic compounds represented by Chemical Formula A.

Advantageous Effects

Over conventional organic light-emitting diodes, the organic light-emitting diode including the amine compound according to the present disclosure has the advantage of exhibiting improved efficiency.

BRIEF DESCRIPTION OF THE DRAWINGS

The FIGURE is a schematic view of an organic light-emitting diode according to an embodiment of the present disclosure.

BEST MODE FOR INVENTION

Mode for Carrying Out the Invention

Below, a detailed description will be given of the present disclosure.

The present disclosure provides an amine compound represented by the following Chemical Formula A:

[Chemical Formula A]

wherein, $A_1$, $A_2$, $A_3$, and $A_4$ may be the same or different and are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of $A_1$ and two adjacent carbon atoms within the aromatic ring of $A_2$ form a 5-membered ring with a carbon atom connected to both substituents $R_1$ and $R_2$, thus establishing a fused ring structure;

two adjacent carbon atoms within the aromatic ring of $A_1$, which do not participate in forming the 5-membered ring with the carbon atom connected to both substituents $R_1$ and $R_2$, are linked to $M_1$ and $M_2$, respectively, in order to form a 5-membered, fused ring, two adjacent carbon atoms within the aromatic ring of $A_2$, which do not participate in forming the 5-membered ring with the carbon atom connected to both substituents $R_1$ and $R_2$, are linked to $M_3$ and $M_4$, respectively, in order to form a 5-membered, fused ring, two adjacent carbon atoms within the aromatic ring of $A_3$ are linked to $M_1$ and $M_2$, respectively, in order to form a 5-membered, fused ring, and two adjacent carbon atoms within the aromatic ring of $A_4$ are linked to $M_3$ and $M_4$, respectively, in order to form a 5-membered, fused ring;

linkers $L_1$ to $L_6$ may be the same or different and are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

at least one of the aromatic rings of $A_1$ to $A_4$ has one to four substituents selected from among a substituted or unsubstituted alkyl of 1 to 30 carbon atoms, a substituted or unsubstituted cycloalkyl of 1 to 30 carbon atoms, a substituted or unsubstituted aryl of 6 to 50 carbon atoms, and a halogen selected from F, Cl, Br, and I;

$M_1$ to $M_4$ may be the same or different and are each independently a single bond, O, S, $CR_3R_4$, $SiR_3R_4$, $GeR_3R_4$, Se, $PR_3$, $BR_3$, or $P(=O)R_3$, with a proviso that one of $M_1$ and $M_2$ is a single bond, and one of $M_3$ and $M_4$ is a single bond;

substituents $R_1$ to $R_4$ and $Ar_1$ to $Ar_4$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 5 to 30 carbon atoms, a substituted or unsubstituted alkyl amine of 1 to 30 carbon atoms, a substituted or unsubstituted aryl amine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen;

in the alterative for $R_1$ and $R_2$, $R_1$ and $R_2$ may be connected to each other to form a mono- or polycyclic aliphatic or aromatic ring which may bear at least one heteroatom selected from among N, O, P, Si, S, Ge, Se, and Te as a ring member;

p1 and p2, r1 and r2, and s1 and s2 are each independently an integer of 1 to 3 and when any of them is 2 or greater, the corresponding linkers $L_1$ to $L_6$ may be the same or different;

x is an integer of 1 or 2;

y is an integer of 0 to 3; and in the alternative for $Ar_1$ and $Ar_4$, $Ar_1$ and $Ar_2$ may be connected to each other to form a ring and/or $Ar_3$ and $Ar_4$ may be connected to each other to form a ring, wherein the term "substituted" in the expression "substituted or unsubstituted" used for Chemical Formula A means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to carbon atoms, a heteroaryl of 2 to 24 carbon atoms or a heteroarylalkyl of 2 to 24 carbon atoms, an alkoxy of 1 to 24 carbon atoms, an alkylamine of 1 to 24 carbon atoms, an arylamine of 1 to 24 carbon atoms, a heteroarylamine of 1 to carbon atoms, an alkylsilyl of 1 to 24 carbon atoms, an arylsilyl of 1 to 24 carbon atoms, and an aryloxy of 1 to 24 carbon atoms.

The expression for a number of carbon atoms such as in "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical, derived from an aromatic hydrocarbon by removing one hydrogen atom, including a mono- or fused ring system consisting of 5 to 7 members and preferably 5 or 6 members. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—$NH_2$, —NH(R), —N(R') (R") wherein R' and R" are each independently an alkyl of 1 to 10 alkyl, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

The amine compound represented by Chemical Formula A according to the present disclosure has the technical feature wherein the aromatic rings of $A_1$ to $A_4$ form a 5-membered ring bearing the carbon atom connected to both substituents $R_1$ and $R_2$ as a ring member, a 5-membered ring bearing $M_1$ and $M_2$ as ring members, a 5-memberered ring bearing $M_3$ and $M_4$ as ring members, thus establishing a fused ring structure, wherein the $A_2$ ring has an amine moiety attached thereto, the amine moiety including $Ar_1$ and $Ar_2$, and at least one of the aromatic rings of $A_1$ to $A_4$ has one to four substituents selected from among a substituted or unsubstituted alkyl of 1 to 30 carbon atoms, a substituted or unsubstituted cycloalkyl of 1 to 30 carbon atoms, a substituted or unsubstituted aryl of 6 to 50 carbon atoms, and a halogen selected from F, Cl, Br, and I, whereby an organic light-emitting diode exhibiting the improved characteristics of high efficiency and long lifespan can be provided.

In a particular embodiment, at least one of the aromatic rings of $A_1$ to $A_4$ has one or two substituents selected from among a substituted or unsubstituted alkyl of 1 to 30 carbon atoms, a substituted or unsubstituted cycloalkyl of 1 to 30 carbon atoms, a substituted or unsubstituted aryl of 6 to 50 carbon atoms, and a halogen selected from F, Cl, Br, and I.

In the amine compound represented by Chemical Formula A according to the present disclosure, $A_1$, $A_2$, $A_3$, and $A_4$ may be the same or different and are each independently a substituted or unsubstituted aromatic hydrocarbon ring of 6 to 50 carbon atoms.

When $A_1$, $A_2$, $A_3$, and $A_4$ in Chemical Formula A each correspond to a substituted or unsubstituted aromatic hydrocarbon ring of 6 to 50 carbon atoms as mentioned above, the aromatic hydrocarbon rings may be the same or different and are each independently one selected from among [Structural Formula 10] to [Structural Formula 21]:

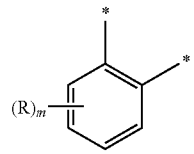

[Structural Formula 10]

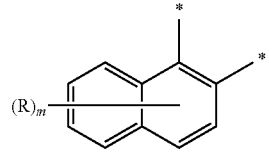

[Structural Formula 11]

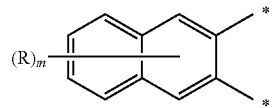

[Structural Formula 12]

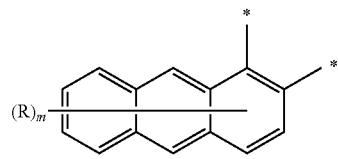

[Structural Formula 13]

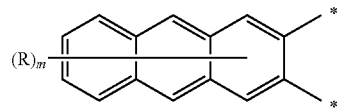

[Structural Formula 14]

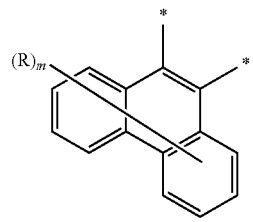

[Structural Formula 15]

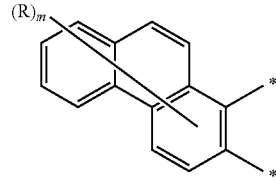

[Structural Formula 16]

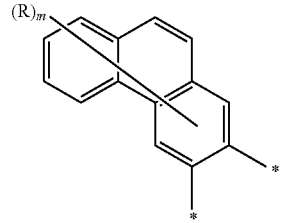

[Structural Formula 17]

[Structural Formula 18]

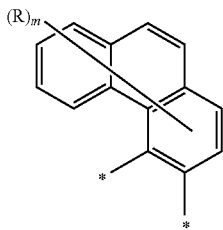

[Structural Formula 19]

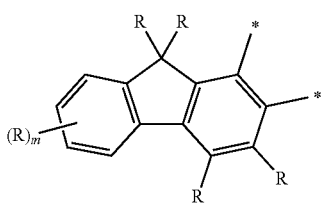

[Structural Formula 20]

[Structural Formula 21]

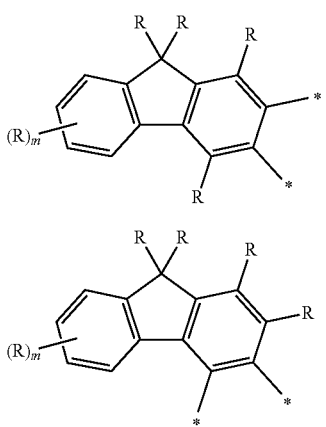

wherein,
when the aromatic hydrocarbon ring is $A_1$ or $A_2$, "-*" denotes a bonding site participating in forming a 5-membered ring bearing the carbon atom connected to both substituents $R_1$ and $R_2$ as a ring member and two other adjacent carbon atoms within the ring are linked to $M_1$ and $M_2$ or to $M_3$ and $M_4$ to form a fused ring,
when the aromatic hydrocarbon ring is $A_3$ or $A_4$, "-*" denotes a bonding site linked to $M_1$ to $M_4$ to form a fuse ring; and
R is as defined for $R_1$ and $R_2$, and m is an integer of 1 to 8 wherein when m is 2 or greater or when R exists as multiple radicals, the resulting R's may be the same or different.

According to one embodiment, the linkers $L_1$ to $L_6$ may each be a single bond, or one selected from among a substituted or unsubstituted arylene of 6 to 20 carbon atoms and a substituted or unsubstituted heteroarylene of 2 to 20 carbon atoms.

In this context, the linkers $L_1$ to $L_6$ may each be a single bond or one selected from among the following [Structural Formula 22] to [Structural Formula 30], p1 and p2, r1 and r2, and s1 and s2 may each be 1 or 2, and x may be 1:

[Structural Formula 22]

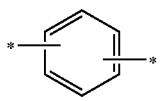

[Structural Formula 23]

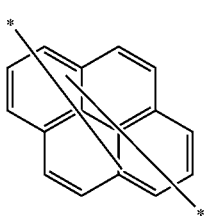

[Structural Formula 24]

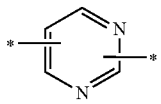

[Structural Formula 25]

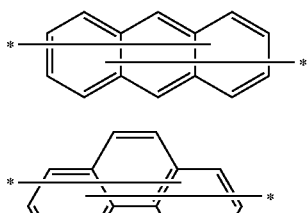

[Structural Formula 26]

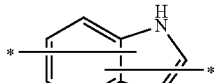

[Structural Formula 27]

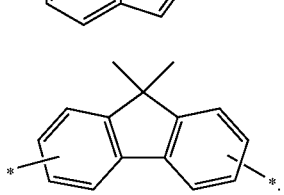

[Structural Formula 28]

[Structural Formula 29]

[Structural Formula 30]

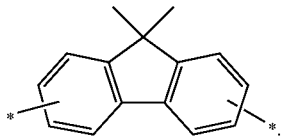

In the linkers, each of unsubstituted carbon atoms of the aromatic ring moiety may be bound with a hydrogen atom or a deuterium atom.

According to some embodiments, the substituents $R_1$ to $R_4$, and $Ar_1$ to $Ar_4$ in Chemical Formula A may be the same or different and are each independently one selected from among a hydrogen atom, a deuterium atom, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms bearing at least one selected from among O, N, S, and Si as a heteroatom, a cyano, and a halogen.

In addition, the amine compound represented by Chemical Formula A may be one selected from among the compounds represented by the following [Chemical Formula 1] to [Chemical Formula 51]:

<Chemical Formula 1>
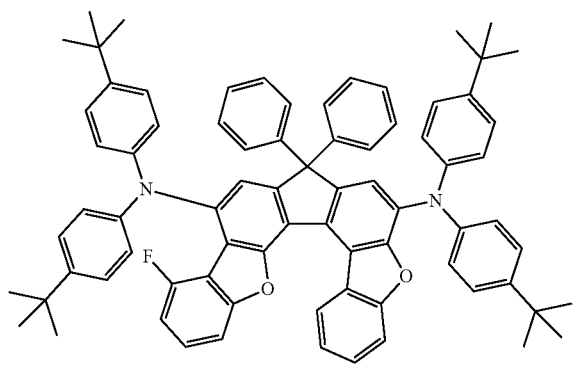
<Chemical Formula 2>
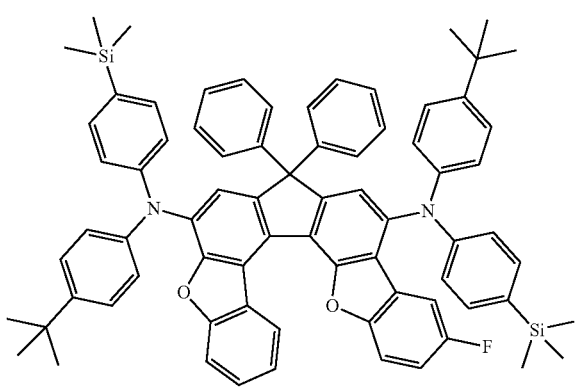
<Chemical Formula 3>
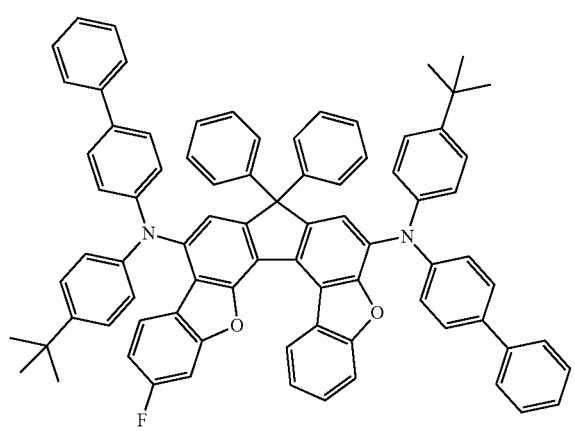
<Chemical Formula 4>
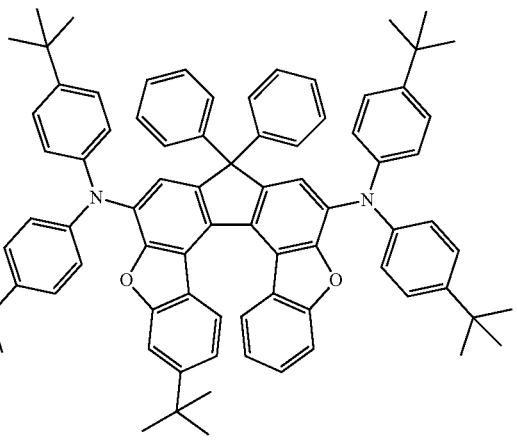
<Chemical Formula 5>
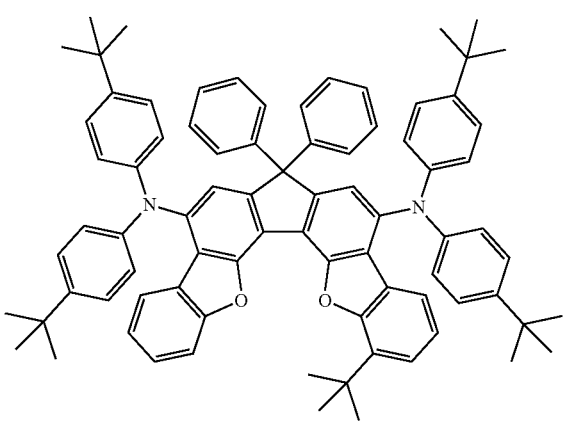
<Chemical Formula 6>
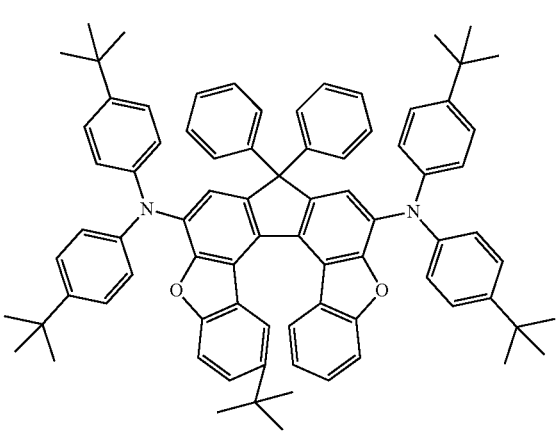

<Chemical Formula 7>
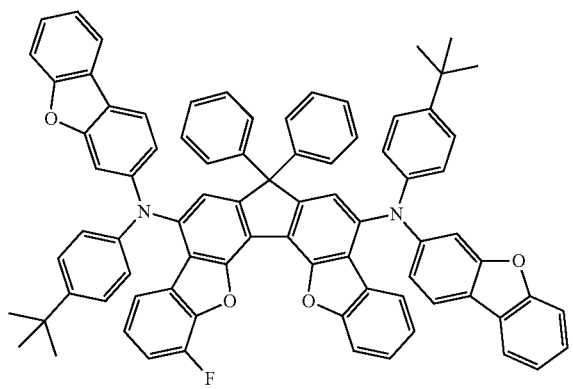
<Chemical Formula 8>
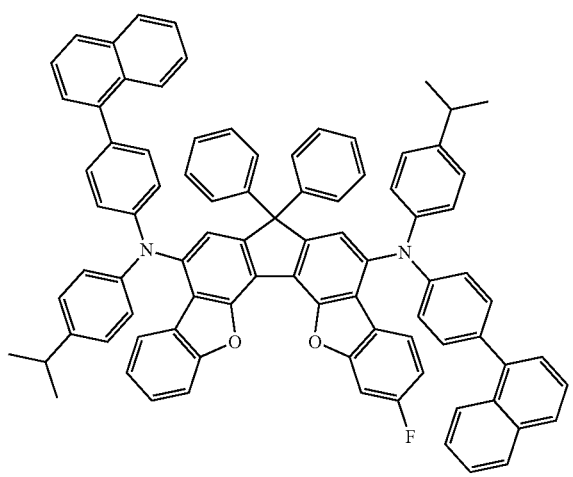
<Chemical Formula 9>
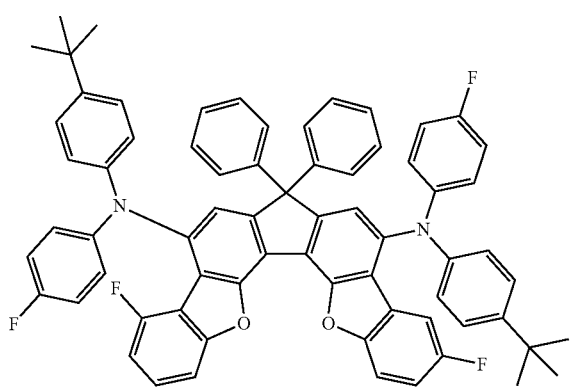
<Chemical Formula 10>
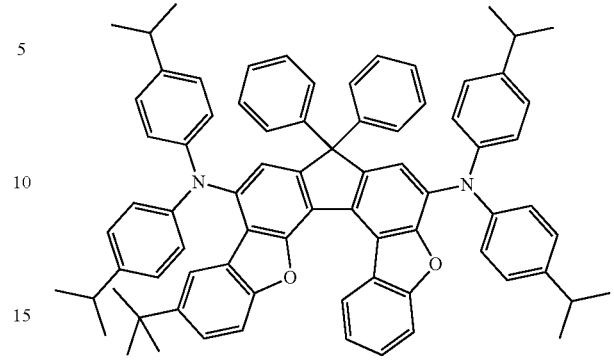
<Chemical Formula 11>
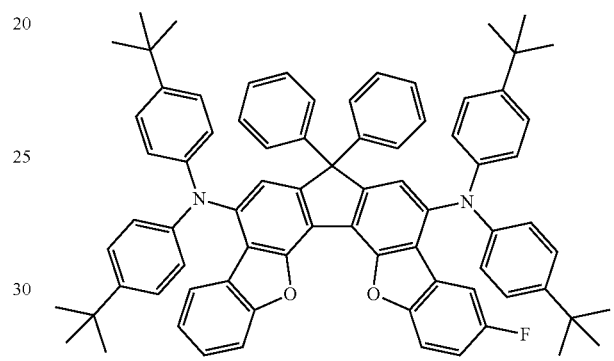
<Chemical Formula 12>
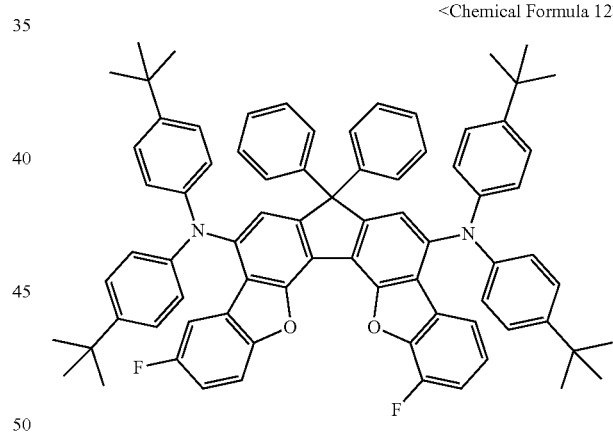
<Chemical Formula 13>
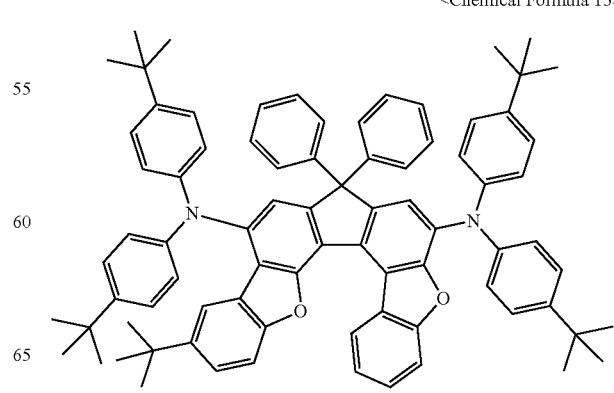

<Chemical Formula 14>
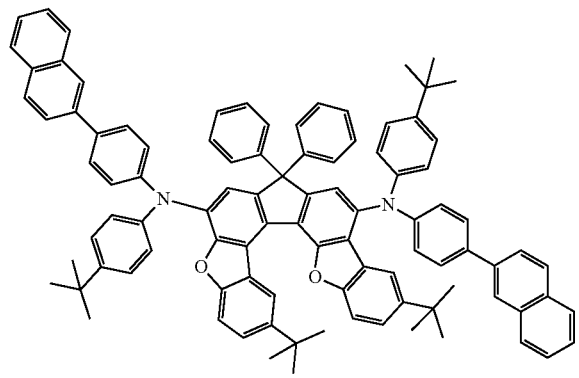
<Chemical Formula 15>
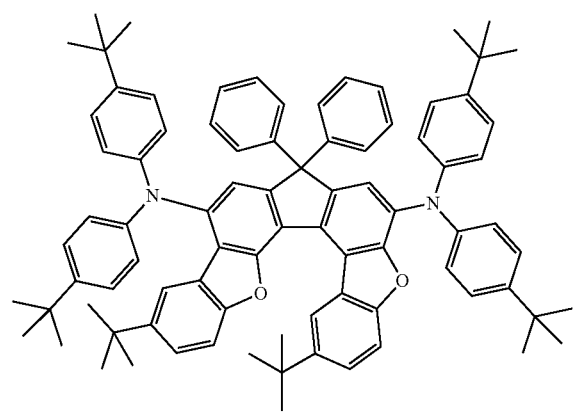
<Chemical Formula 16>
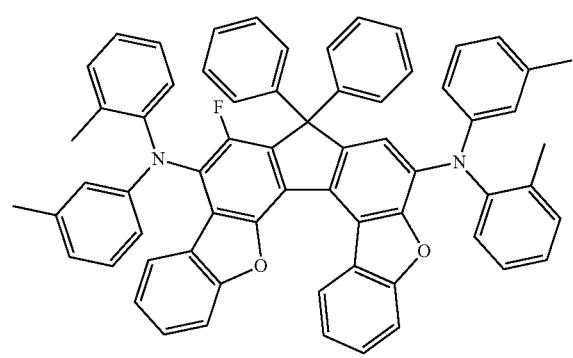
<Chemical Formula 17>
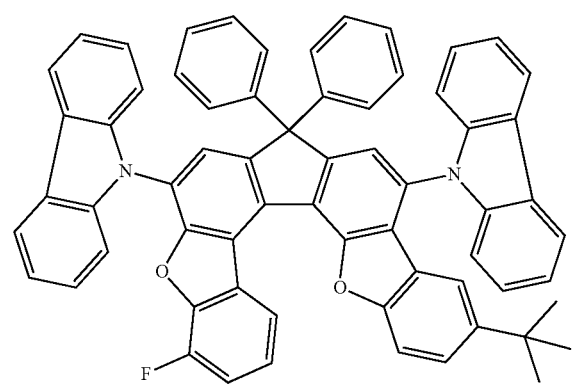
<Chemical Formula 18>
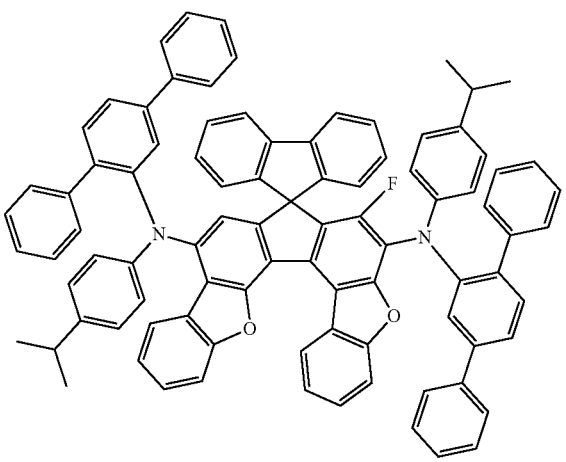
<Chemical Formula 19>
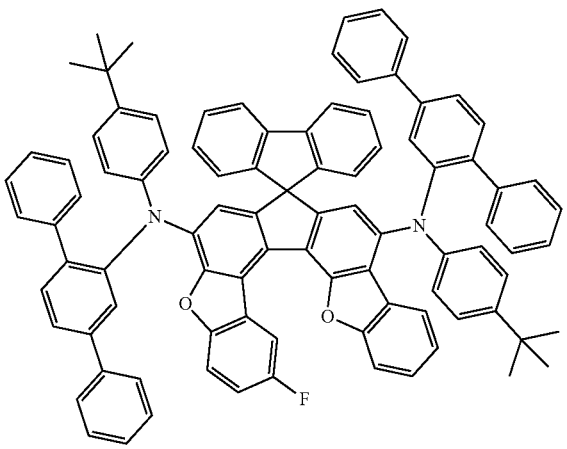
<Chemical Formula 20>
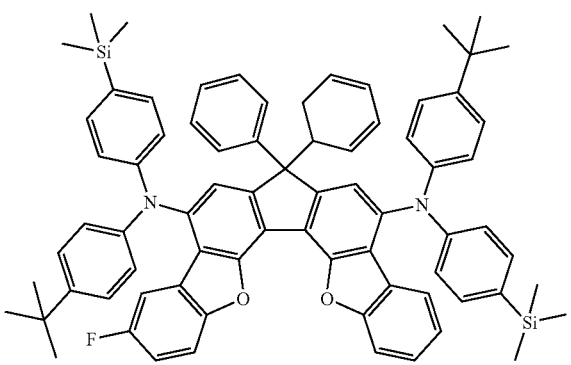

-continued
<Chemical Formula 21>
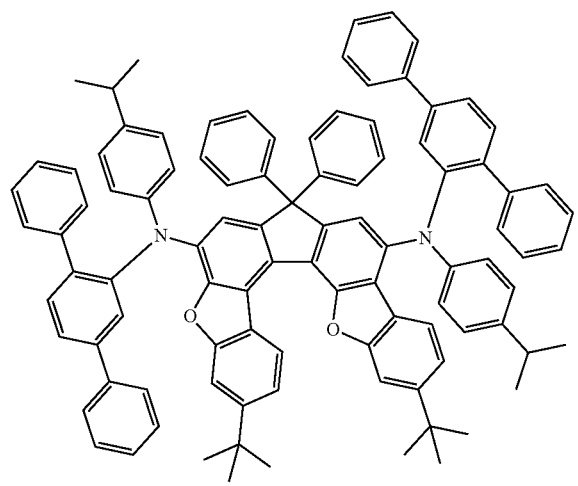
<Chemical Formula 22>
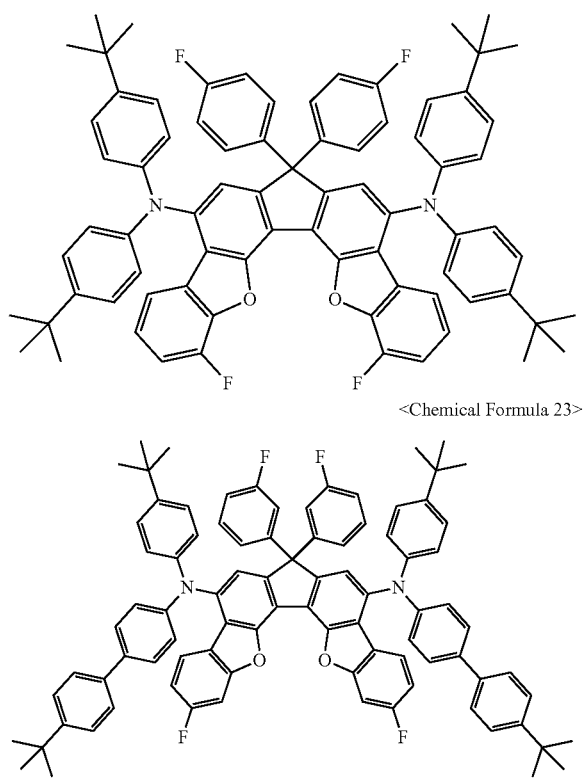
<Chemical Formula 23>
<Chemical Formula 24>
-continued
<Chemical Formula 25>
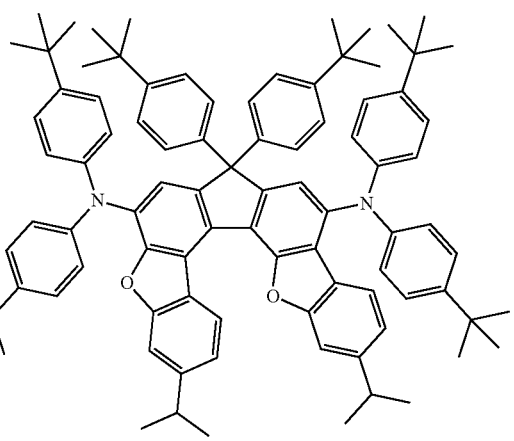
<Chemicla Formula 26>
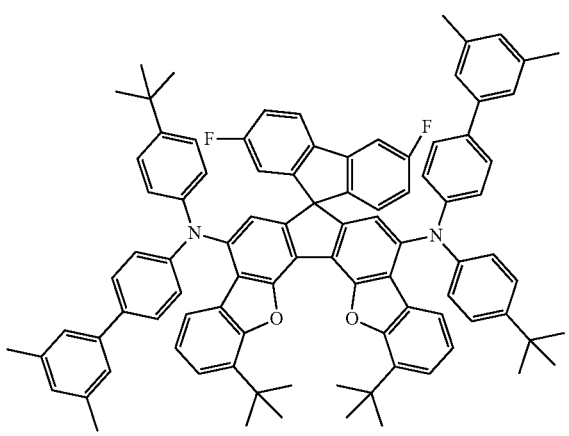
<Chemical Formula 27>
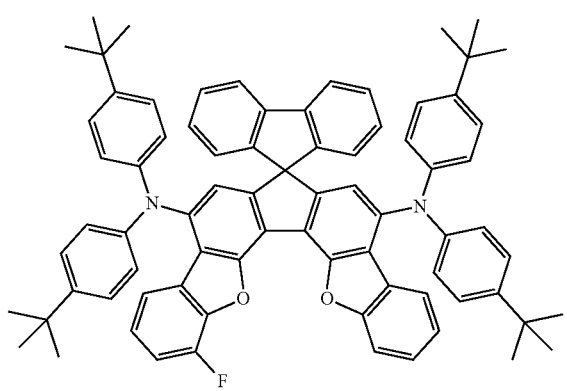

<Chemical Formula 28>
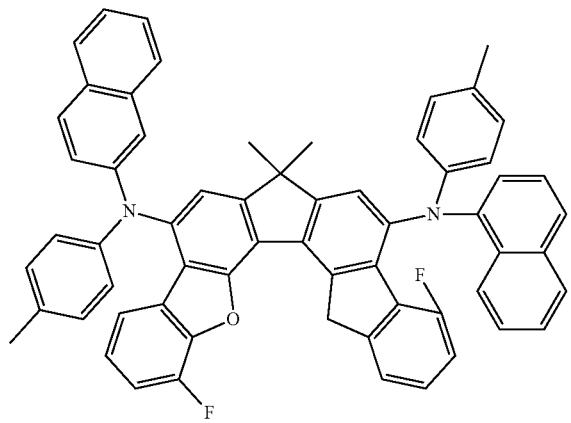
<Chemical Formula 29>
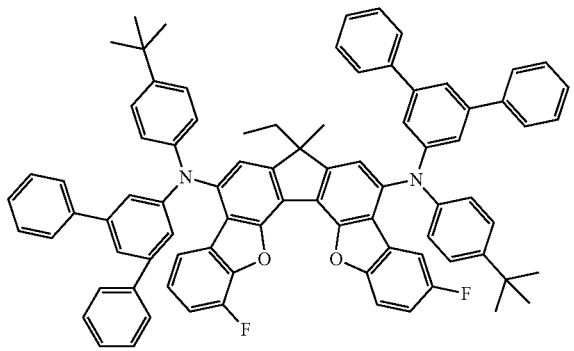
<Chemical Formula 30>
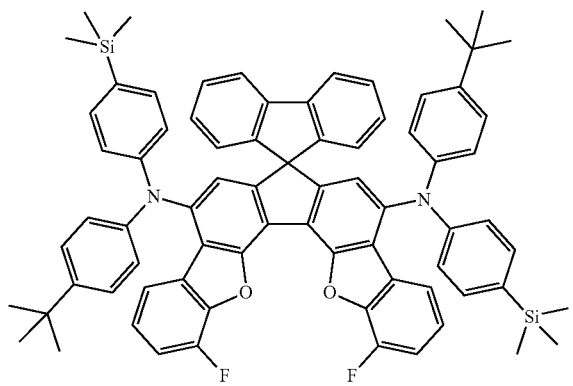
<Chemical Formula 31>
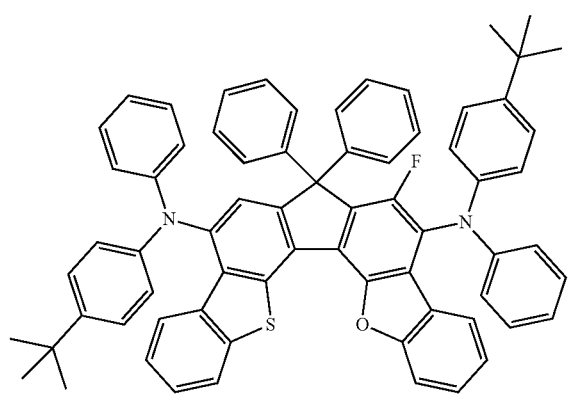
<Chemical Formula 32>
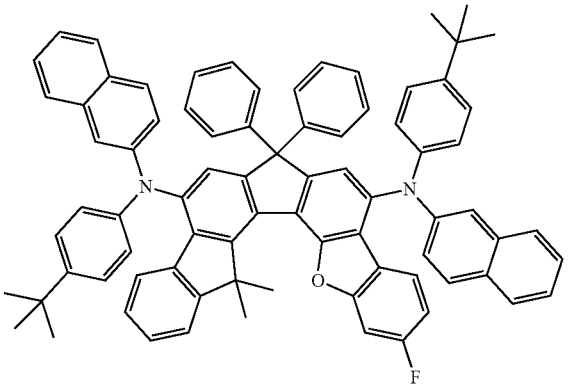
<Chemical Formula 33>
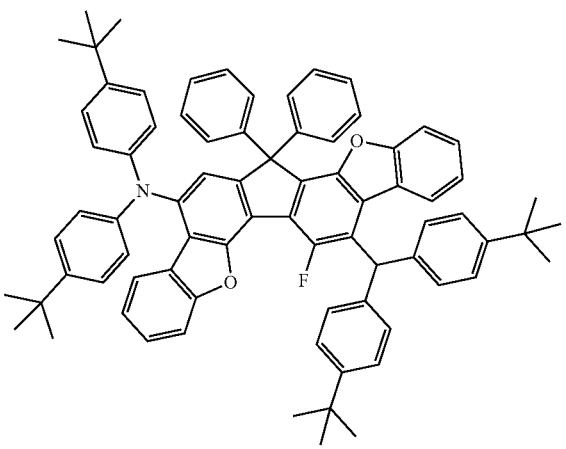
<Chemical Formula 34>
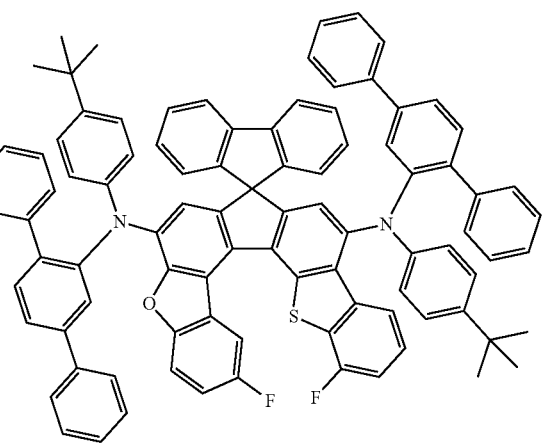

<Chemical Formula 35>
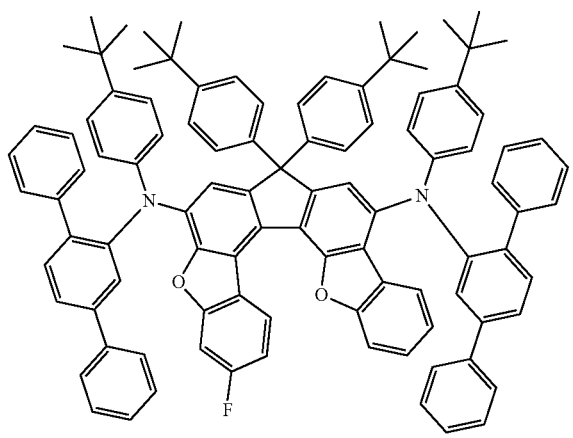
<Chemical Formula 36>
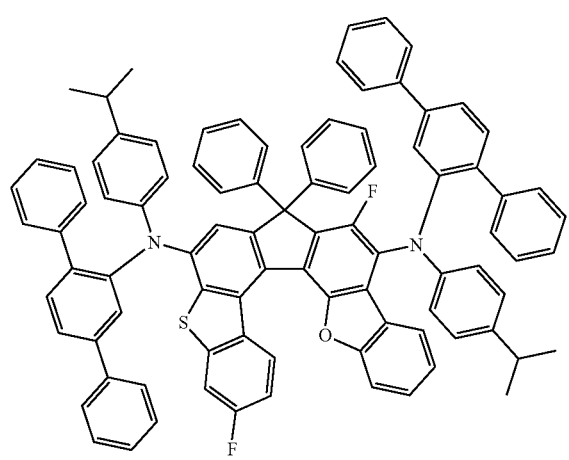
<Chemical Formula 37>
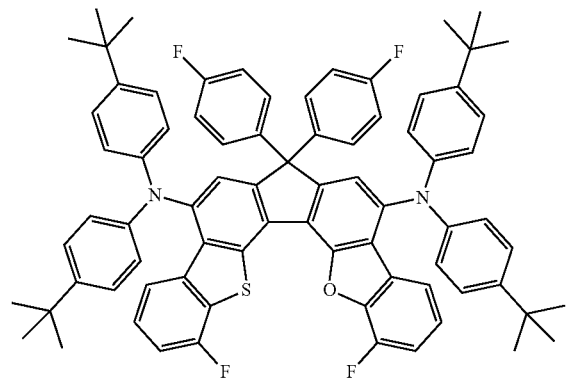
<Chemical Formula 38>
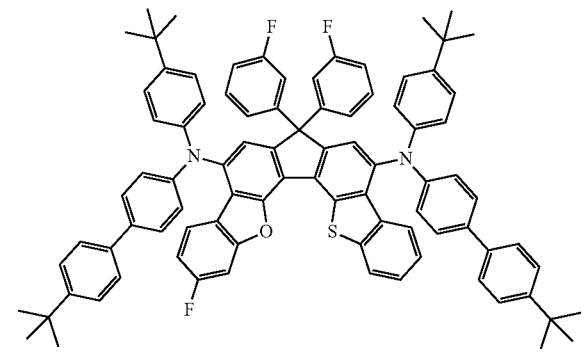
<Chemical Formula 39>
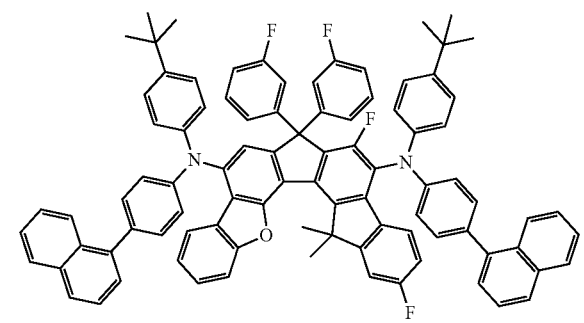
<Chemical Formula 40>
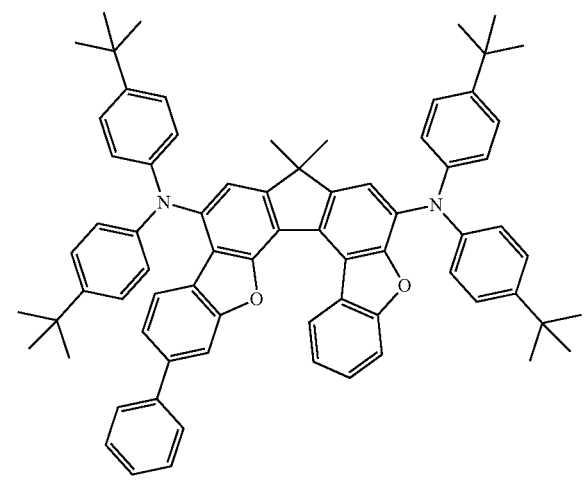

<Chemical Formula 41>
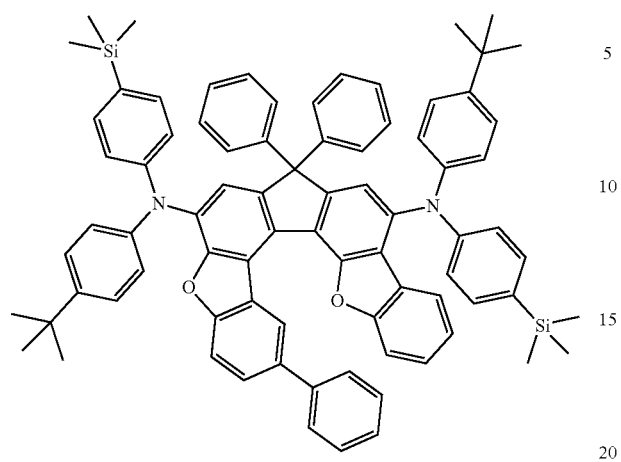
<Chemical Formula 42>
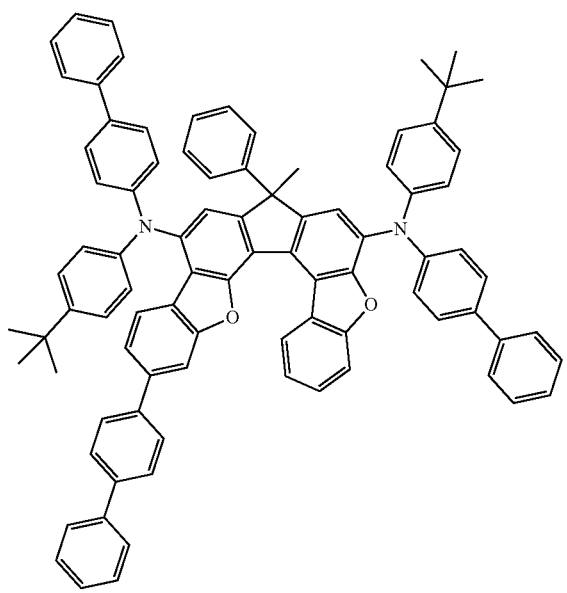
<Chemical Formula 43>
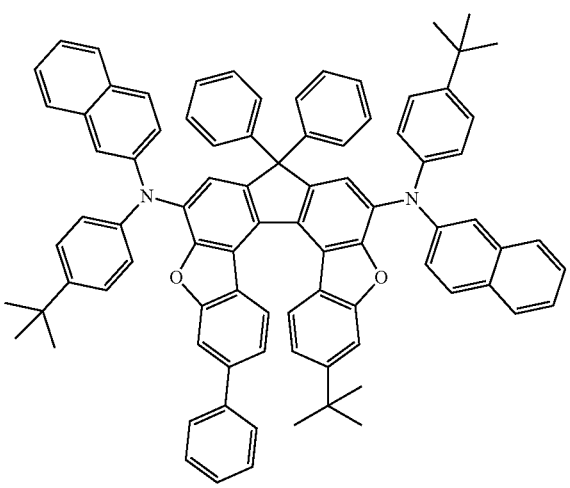
<Chemical Formula 44>
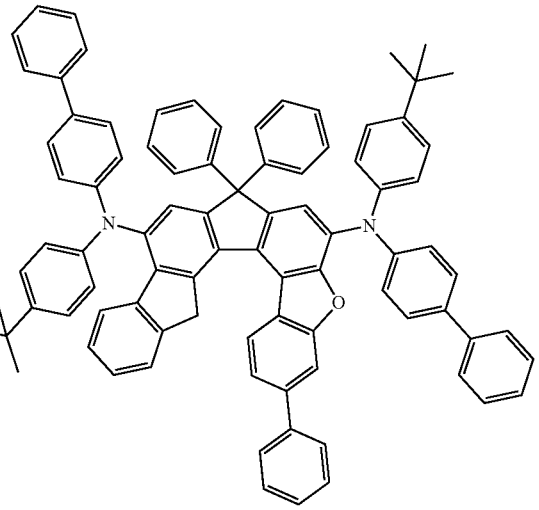
<Chemical Formula 45>
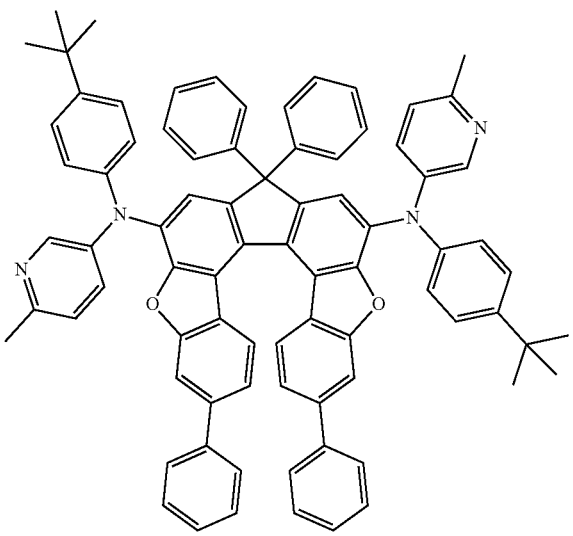
<Chemical Formula 46>
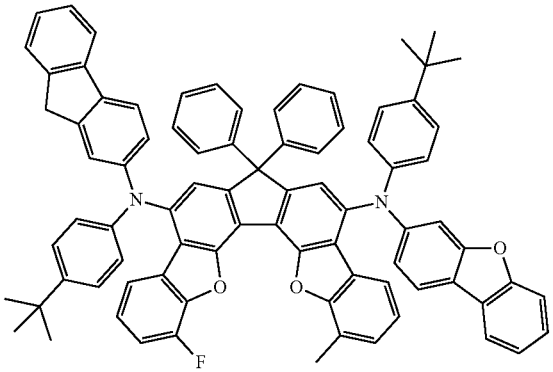

<Chemical Formula 47>

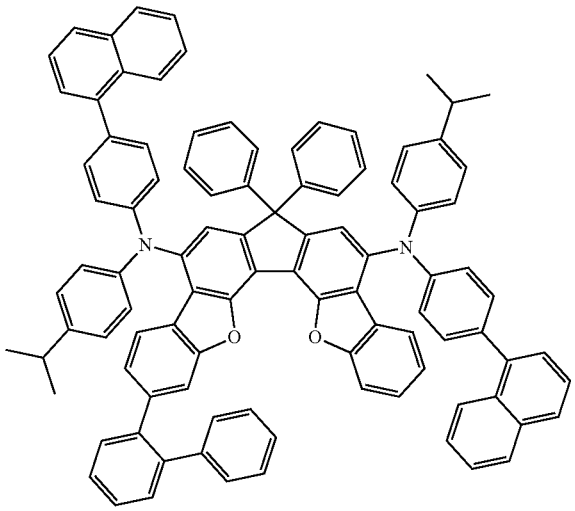

<Chemical Formula 48>

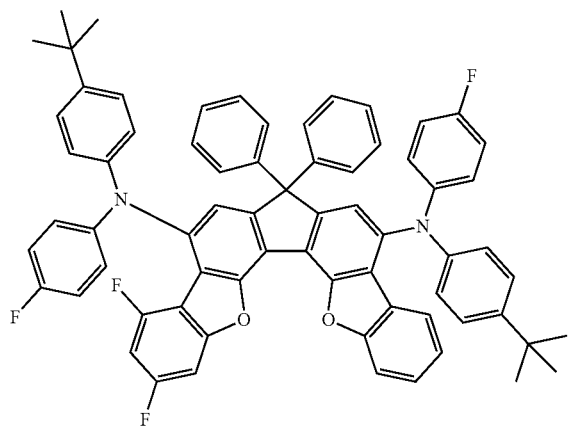

<Chemical Formula 49>

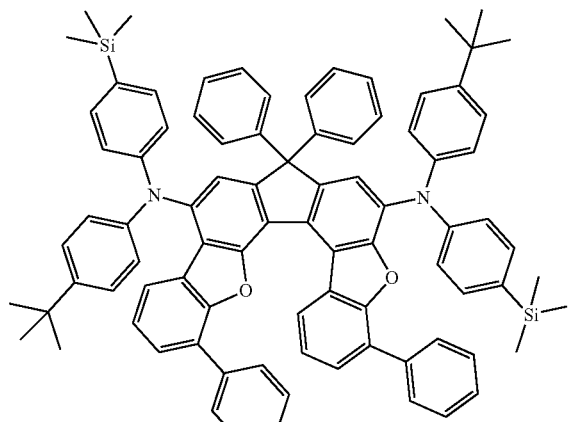

<Chemical Formula 50>

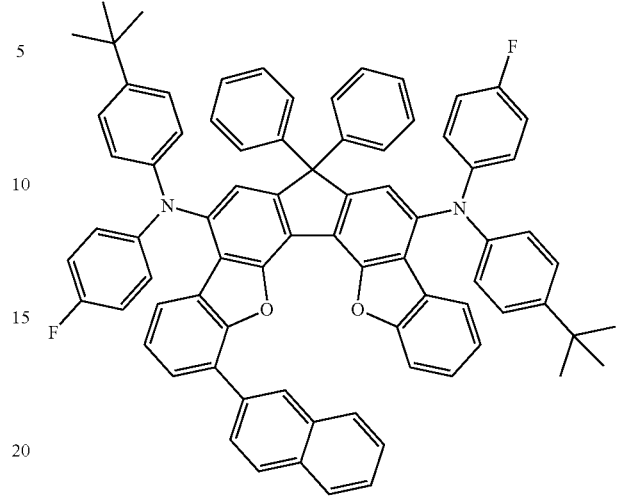

<Chemical Formula 51>

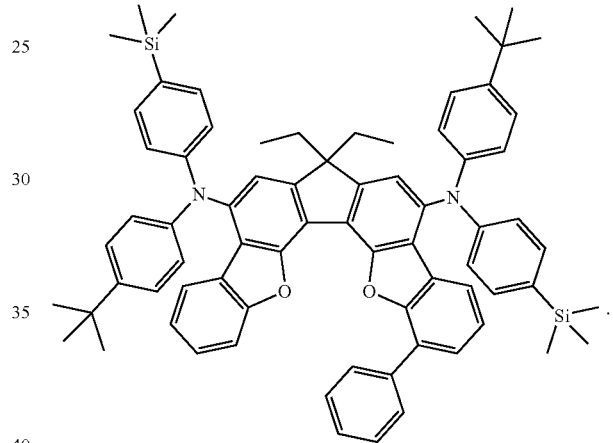

Also, the present disclosure provides an organic light-emitting diode, comprising: a first electrode; a second electrode facing the first electrode; and a light-emitting layer interposed between the first electrode and the second electrode, wherein the light-emitting layer includes at least one of the amine compounds represented by Chemical Formula A according to the present disclosure.

In the present disclosure, the phrase "(a light-emitting layer) includes at least one organic compound" may be construed to mean that "(a light-emitting layer) may include a single organic compound species or two or more different species of organic compounds falling within the scope of the present disclosure".

Here, the light-emitting layer includes a host and a dopant, wherein the organic luminescent compound of the present disclosure may be used as the dopant. Together with the dopant, a host material may be employed in the light-emitting layer. When the light-emitting layer comprises a host and a dopant, the content of the dopant may range from about 0.01 to 20 parts by weight, based on 100 parts by weight of the host, but is not limited thereto.

When the amine compound represented by Chemical Formula A is used as a dopant, together with a host in the light-emitting layer, suitable selection of the substituents on the amine compound may control and further improve efficiency and lifespan characteristics in the organic light-emitting diode.

In an illustrative embodiment of the organic light-emitting diode according to the present disclosure, a host used in the light-emitting layer may be an anthracene derivative represented by the Chemical Formula B:

[Chemical Formula B]

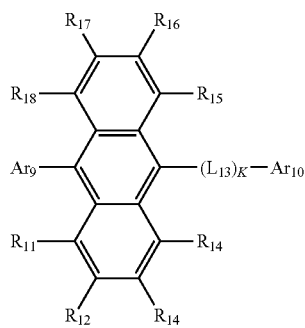

wherein $R_{11}$ to $R_{18}$ may be the same or different and are each as defined for $R_1$ to $R_9$ above;

$Ar_9$ and $Ar_{10}$ may be the same or different and are each independently one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 5 to 30 carbon atoms, a substituted or unsubstituted alkyl amine of 1 to 30 carbon atoms, a substituted or unsubstituted aryl amine of 5 to 30 carbon atoms, a substituted or unsubstituted alkylsilyl of 1 to 30 carbon atoms, and a substituted or unsubstituted arylsilyl of 5 to 30 carbon atoms;

$L_{13}$ is a single bond, or one selected from a substituted or unsubstituted arylene of 6 to 20 carbon atoms and a substituted or unsubstituted heteroarylene of 2 to 20 carbon atoms, and k is an integer of 1 to 3 and when k is 2 or greater, the corresponding $L_{13}$'s may be the same or different.

In more detail, $Ar_9$ in Chemical Formula B may be a substituent represented by the following Chemical Formula C-1:

[Chemical Formula C-1]

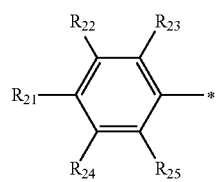

wherein $R_{21}$ to $R_{25}$, which may be the same or different, are each as defined for $R_1$ and $R_9$; and may each be linked to an adjacent one to form a saturated or unsaturated cyclic ring.

In this case, $L_{13}$ may be a single bond or a substituted or unsubstituted arylene of 6 to 20 carbon atoms, and k may be 1 or 2, with the proviso that when k is 2, corresponding $L_{13}$'s may be the same or different.

According to one embodiment, the anthracene derivative may be one selected from the compounds represented by the following [Chemical Formula 61] to [Chemical Formula 99]:

<Chemical Formula 61>

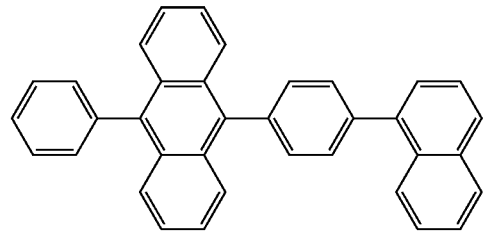

<Chemical Formula 62>

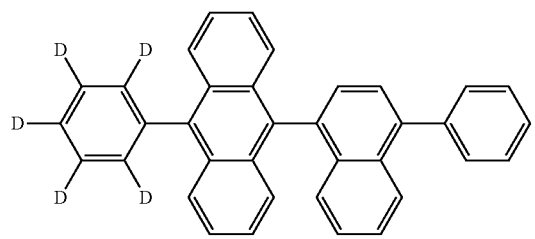

<Chemical Formula 63>

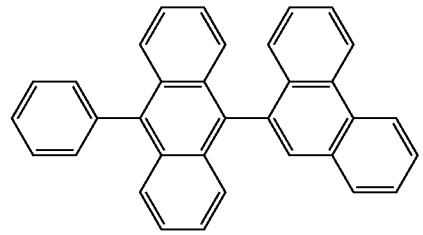

<Chemical Formula 64>

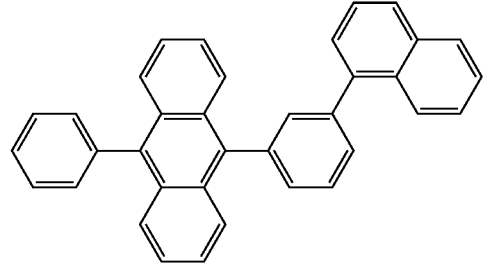

<Chemical Formula 65>
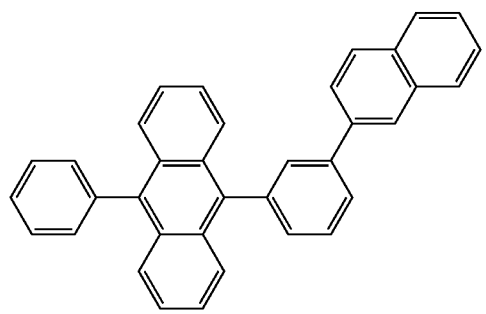
<Chemical Formula 66>
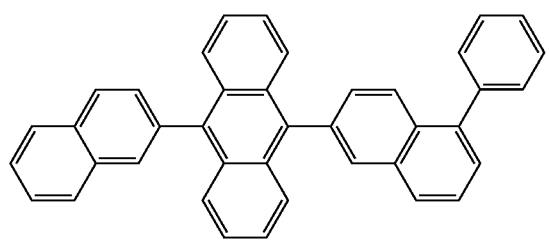
<Chemical Formula 67>
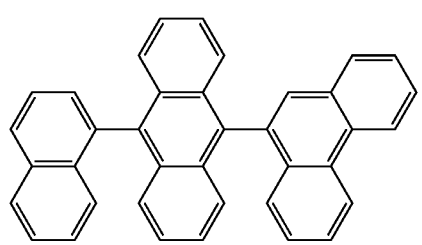
<Chemical Formula 68>
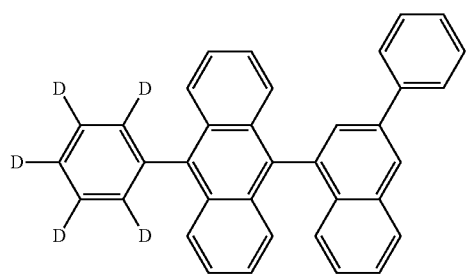
<Chemical Formula 69>
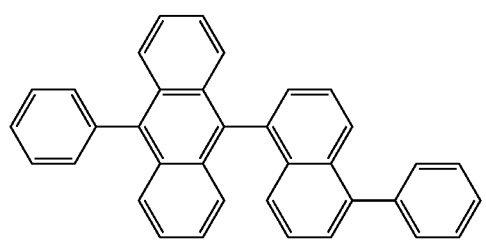
<Chemical Formula 70>
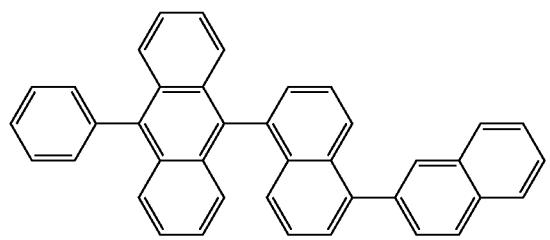
<Chemical Formula 71>
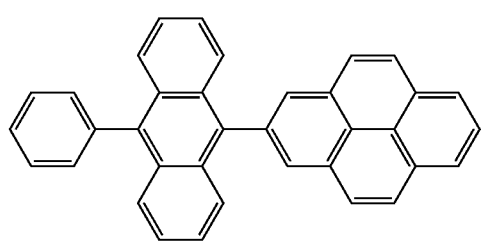
<Chemical Formula 72>
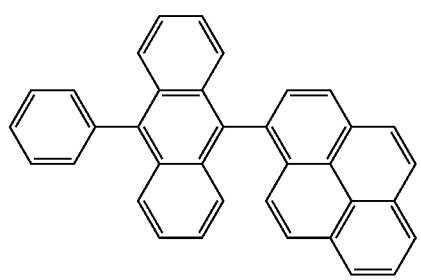
<Chemical Formula 73>
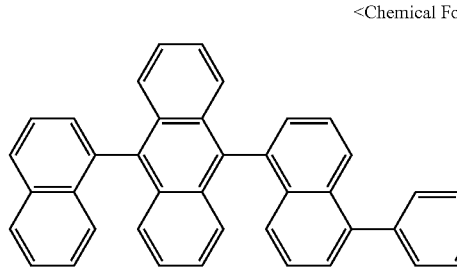
<Chemical Formula 74>
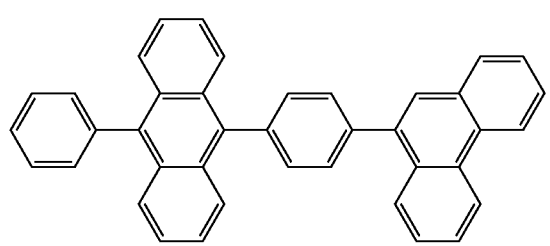

<Chemical Formula 75>
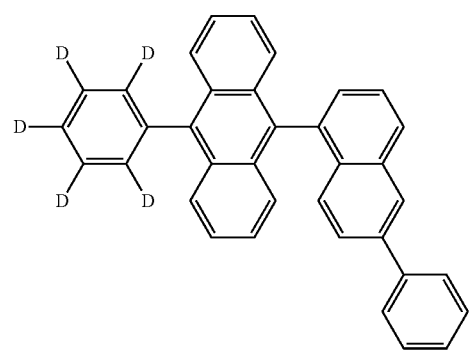
<Chemical Formula 76>
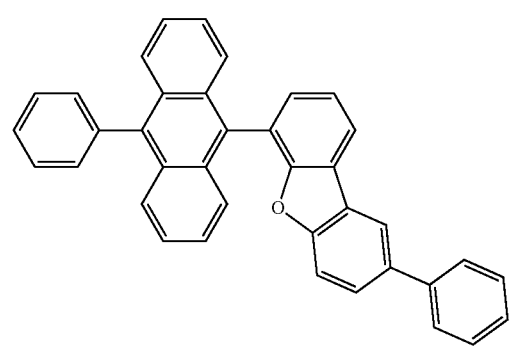
<Chemical Formula 77>
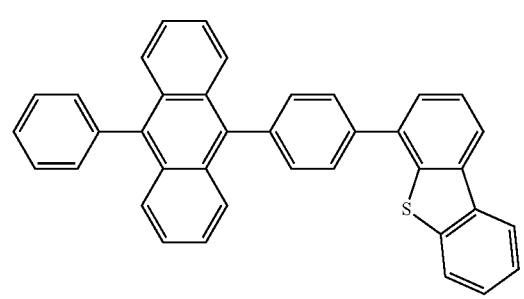
<Chemical Formula 78>
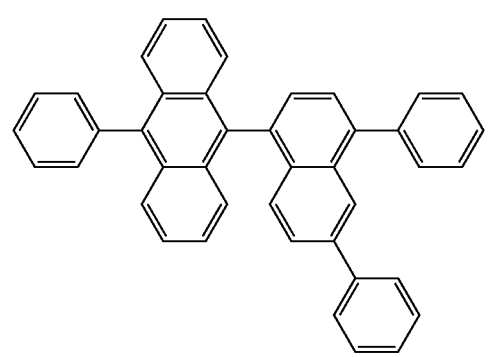
<Chemical Formula 79>
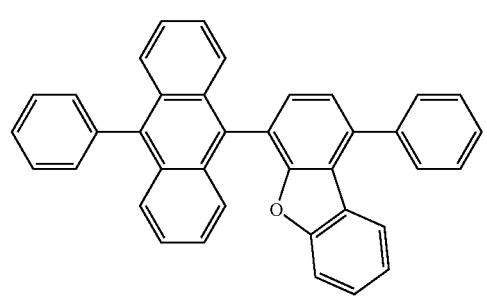
<Chemical Formula 80>
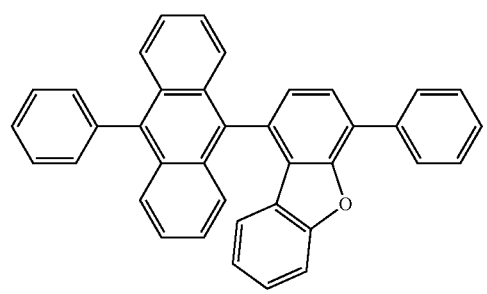
<Chemical Formula 81>
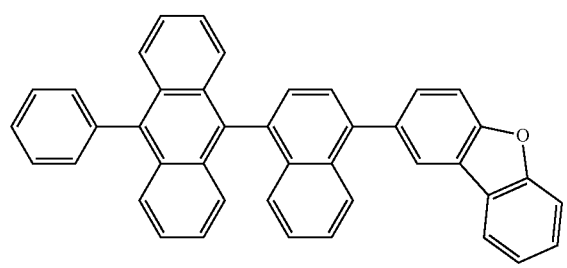
<Chemical Formula 82>
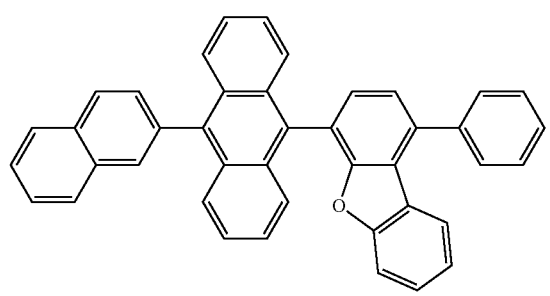
<Chemical Formula 83>
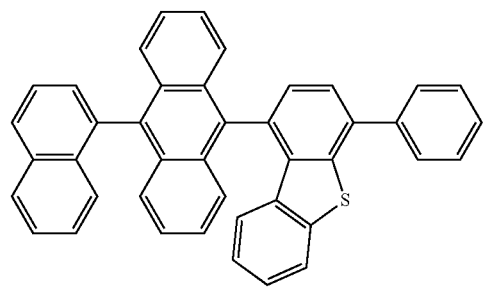

<Chemical Formula 84>
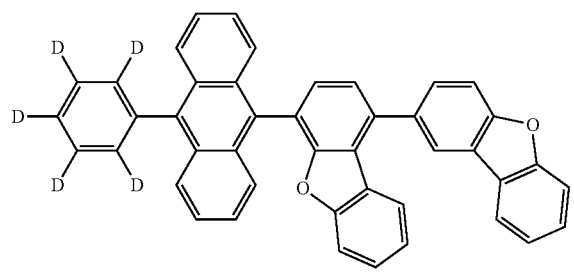
<Chemical Formula 85>
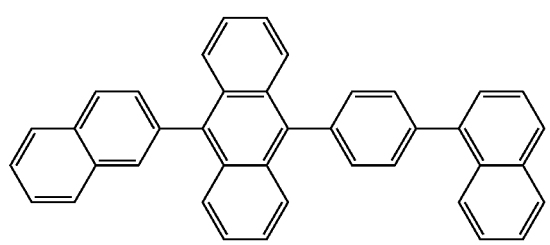
<Chemical Formula 86>
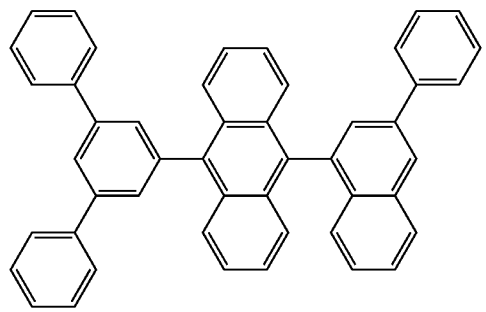
<Chemical Formula 87>
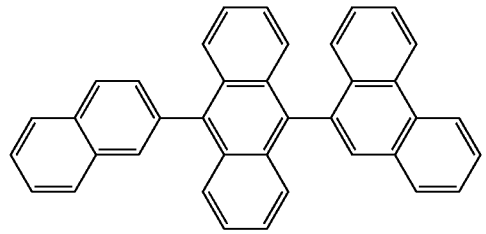
<Chemical Formula 88>
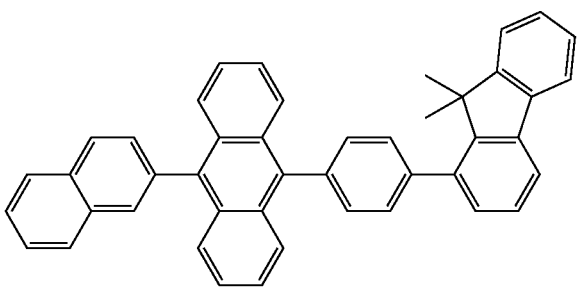
<Chemical Formula 89>
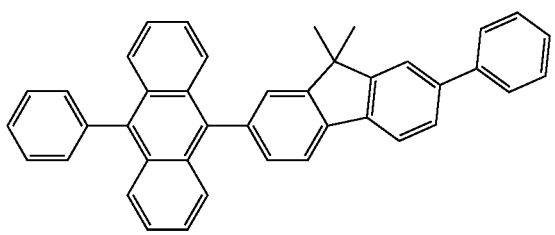
<Chemical Formula 90>
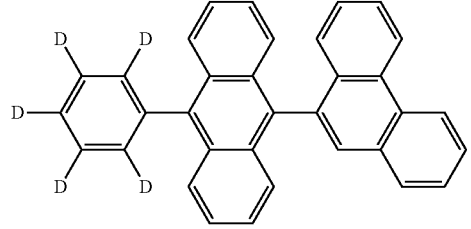
<Chemical Formula 91>
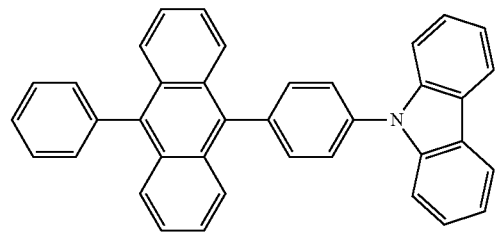
<Chemical Formula 92>
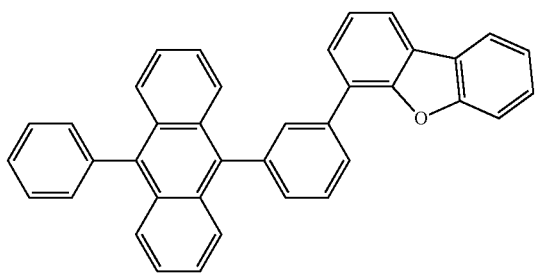
<Chemical Formula 93>
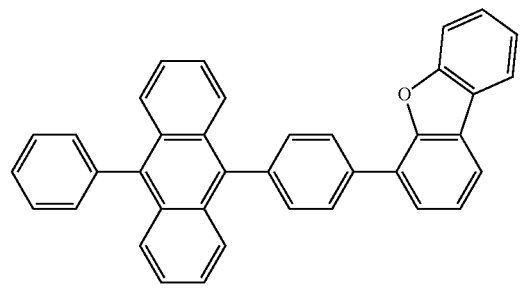
<Chemical Formula 94>
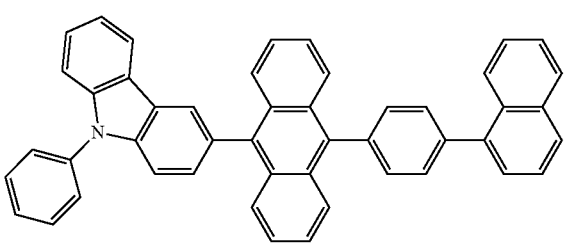

-continued

<Chemical Formula 95>

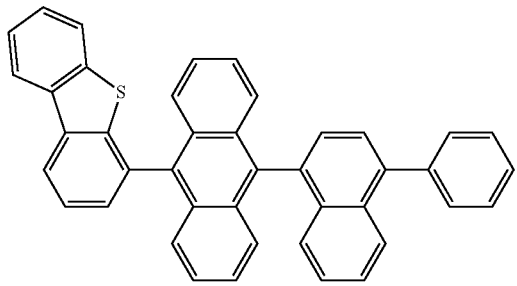

<Chemical Formula 96>

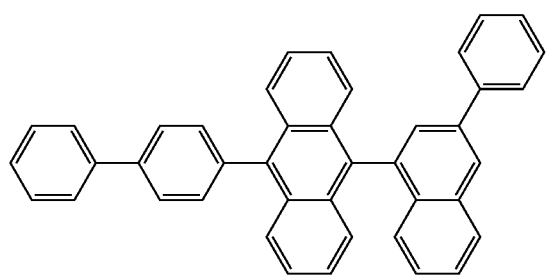

<Chemical Formula 97>

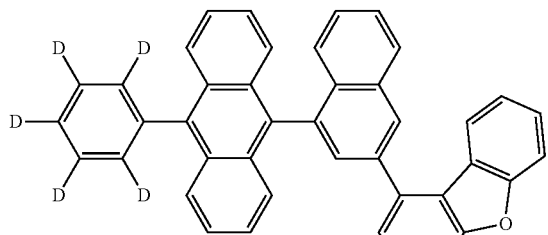

<Chemical Formula 98>

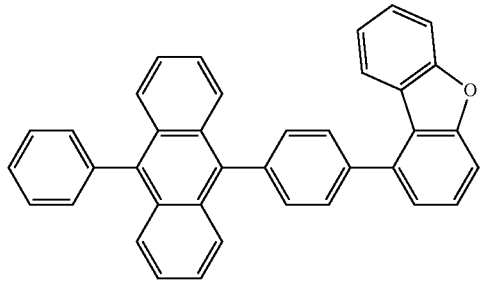

<Chemical Formula 99>

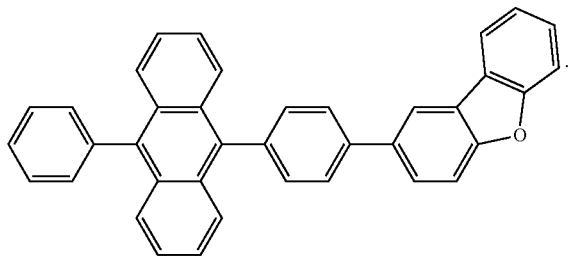

In addition to the above-mentioned dopants and hosts, the light-emitting layer may further include various hosts and dopant materials.

According to some particular embodiments of the present disclosure, the organic light-emitting diode may comprise at least one of a hole injection layer, a hole transport layer, a functional layer capable of both hole injection and hole transport, an electron transport layer, and an electron injection layer, in addition to the light-emitting layer.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum (Alq3), TAZ, Balq, beryllium bis(benzoquinolin-10-olate) (Bebq2), ADN, Compound 201, Compound 202, BCP, and oxadiazole derivatives such as PBD, BMD, BND, etc., but are not limited thereto:

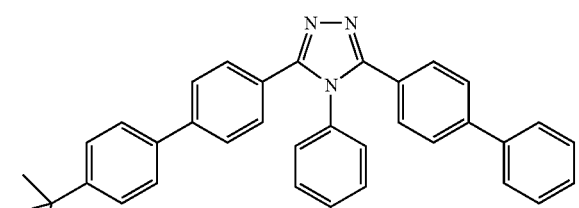

TAZ

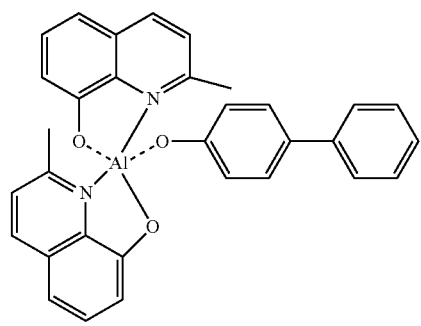

Balq

<compound 201>

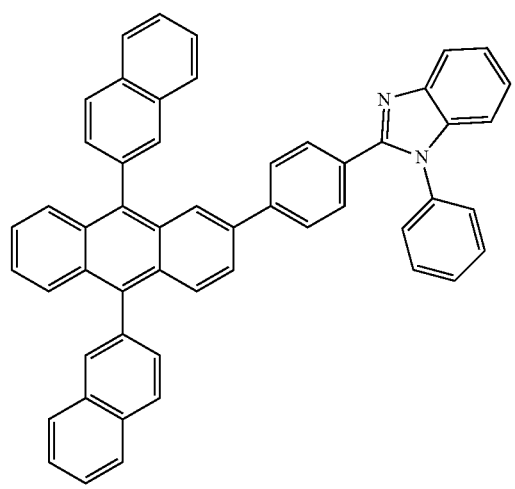

<compound 202>

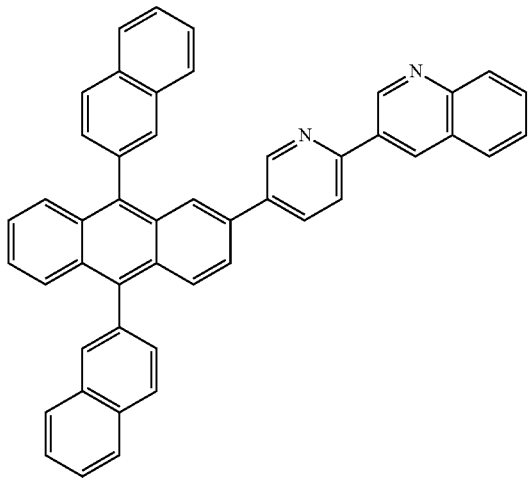

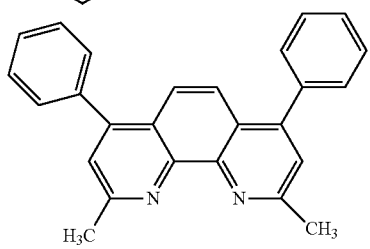

BCP

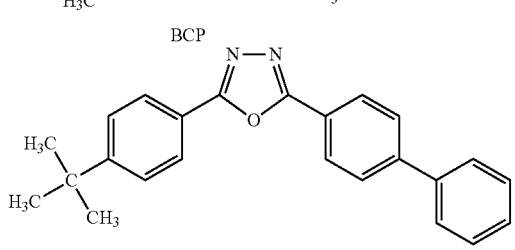

PBD

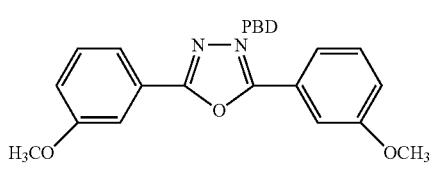

BMD

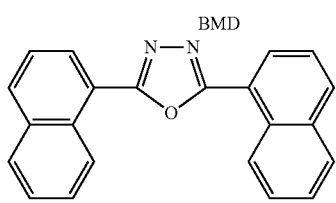

BND

In addition, the electron transport layer may be made of the organic metal compound represented by Chemical Formula C, either alone or in combination with the aforementioned material:

$$Y_m\text{-}M\text{-}(OA)_n \quad \text{[Chemical Formula C]}$$

wherein,

Y is a ligand that contains two moieties respectively responsible for forming a single bond with M through a direct bond M and for forming a coordinate bond with M, each moiety being selected from among C, N, O and S, and which is chelated by the single bond and the coordinate bond;

M is an alkali metal, an alkaline earth metal, aluminum (Al), or a boron (B) atom, wherein:

when M is an alkali metal, m=1 and n=0 when M is an alkaline earth metal, m=1 and n=1, or m=2 and n=0, or when M is aluminum or a boron, m is an integer of 1 to 3 and n is an integer of 0 to 2, satisfying the relationship m+n=3;

OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms baring a heteroatom selected from among O, N, S, and Si as a ring member;

wherein the term 'substituted' in the expression 'substituted or unsubstituted' means having at least one substituent selected from the group consisting of a deuterium atom, a cyano, a halogen, a hydroxy, a nitro, an alkyl, an alkoxy, an alkylamino, an arylamino, a hetero arylamino, an alkylsilyl, an arylsilyl, an aryloxy, an aryl, a heteroaryl, germanium, phosphorus, and boron.

In the present disclosure, the Y's may be the same or different and are each independently selected from among the following Structural Formulas [Structural Formula C1] to [Structural Formula C39], but are not limited thereto:

[Structural Formula C1]

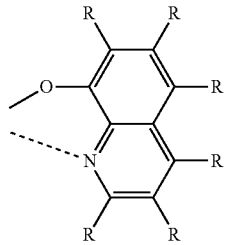

[Structural Formula C2]

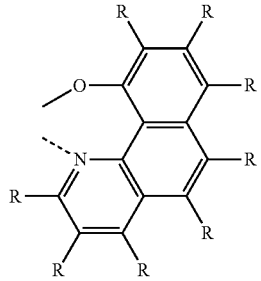

[Structural Formula C3]
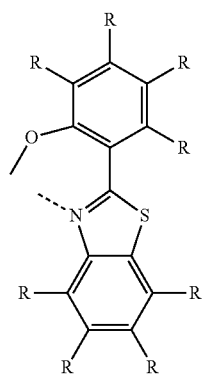
[Structural Formula C4]
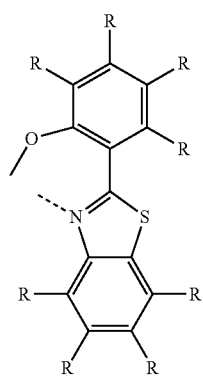
[Structural Formula C4]
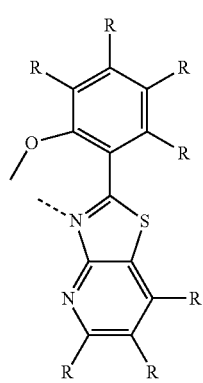
[Structural Formula C5]
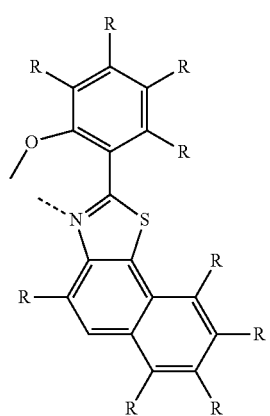
[Structural Formula C6]
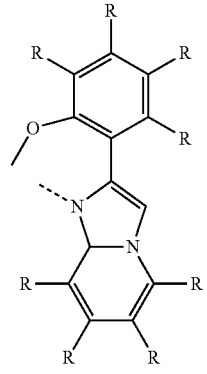
[Structural Formula C7]
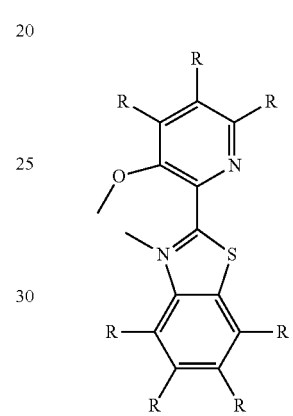
[Structural Formula C8]
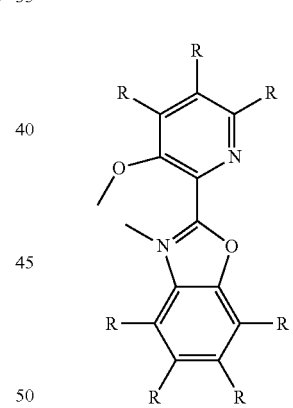
[Structural Formula C9]
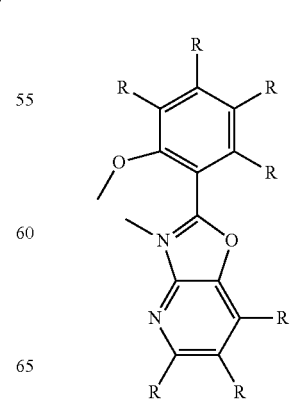

[Structural Formula C10]
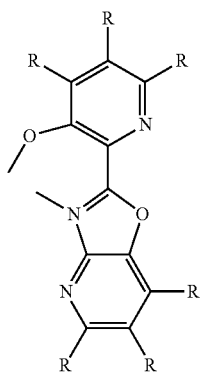
[Structural Formula C11]
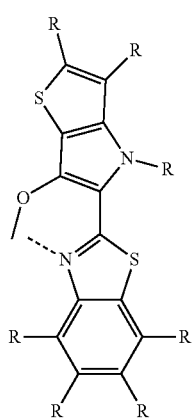
[Structural Formula C12]
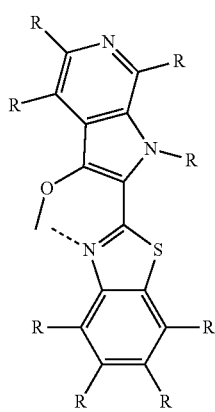
[Structural Formula C13]
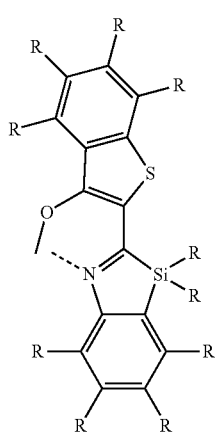
[Structural Formula C14]
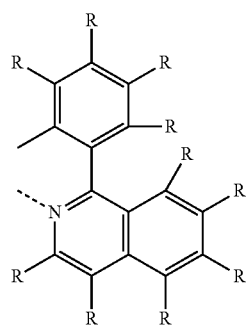
[Structural Formula C15]
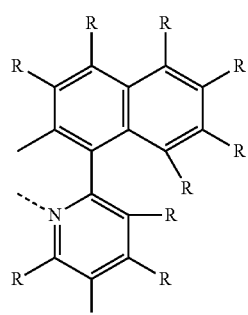
[Structural Formula C16]
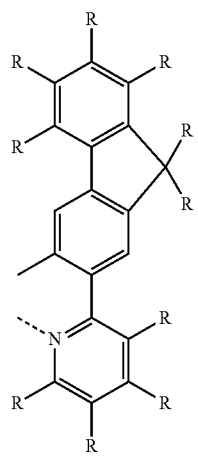
[Structural Formula C17]
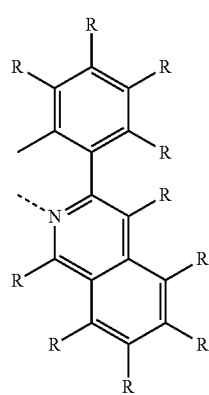

[Structural Formula C18]
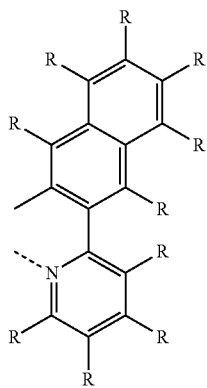
[Structural Formula C19]
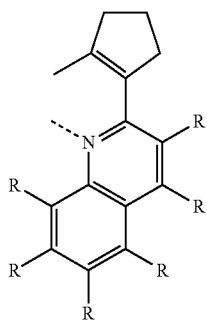
[Structural Formula C20]
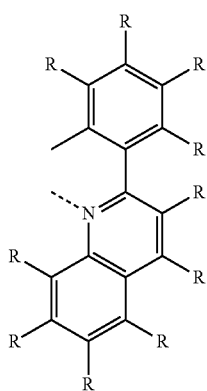
[Structural Formula C21]
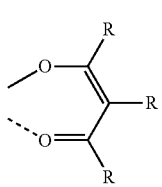
[Structural Formula C22]
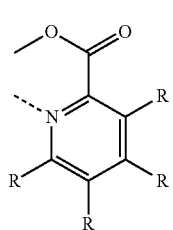
[Structural Formula C23]
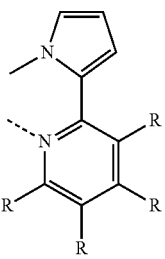
[Structural Formula C24]
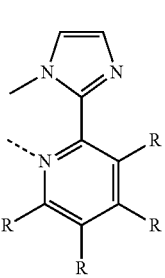
[Structural Formula C25]
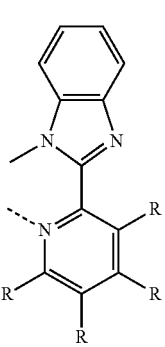
[Structural Formula C26]
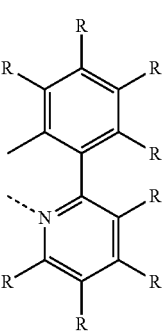
[Structural Formula C27]
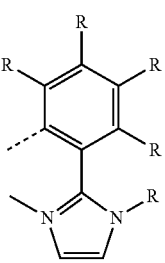

[Structural Formula C28]
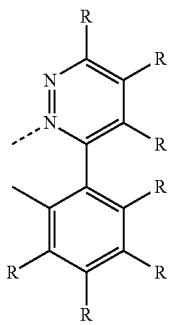
[Structural Formula C32]
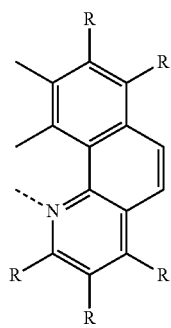
[Structural Formula C29]
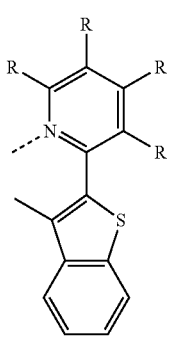
[Structural Formula C33]
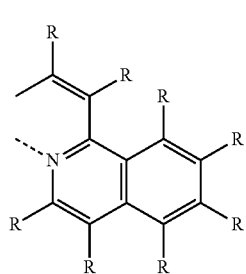
[Structural Formula C30]
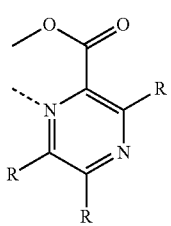
[Structural Formula C34]
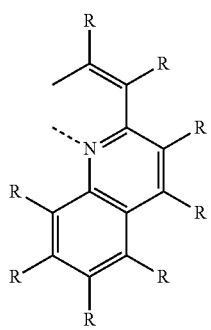
[Structural Formula C31]
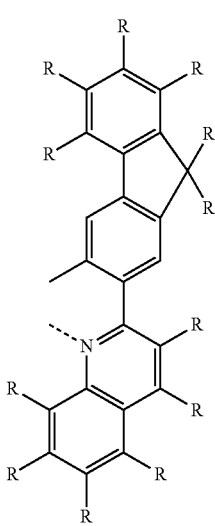
[Structural Formula C35]
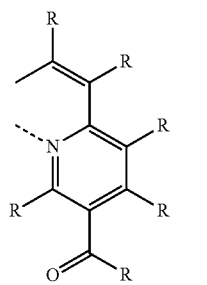
[Structural Formula C36]
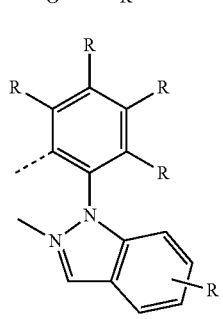

-continued

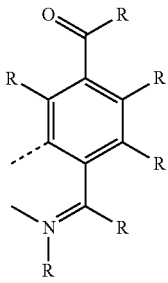
[Structural Formula C37]

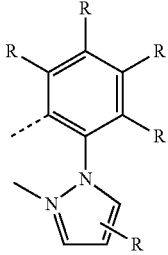
[Structural Formula C38]

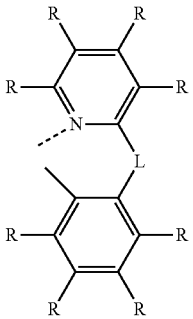
[Structural Formula C39]

wherein,

R's, which may be the same or different, are each independently selected from a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker.

Below, the organic light-emitting diode of the present disclosure is explained with reference to the FIGURE.

The FIGURE is a schematic cross-sectional view of the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injection layer 30 and an electron injection layer 70. In addition, one or two intermediate layers may be further formed in the organic light-emitting diode, or a hole barrier layer or an electron barrier layer may also be employed.

Reference is made to the FIGURE with regard to the fabrication of the organic light-emitting diode of the present disclosure. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO$_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imposed on the hole injection layer material, as long as it is one that is typically used in the art. For example, mention may be made of 2-TNATA [4,4',4''-tris(2-naphthylphenyl-phenylamino)-triphenylamine], NPD [N,N'-di(1-naphthyl)-N,N'-diphenylbenzidine], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine], but the present disclosure is not limited thereby.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenyl-benzidine (a-NPD).

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å.

Further, one or more layers selected from among a hole injection layer, a hole transport layer, an electron barrier layer, a light-emitting layer, a hole barrier layer, an electron transport layer, and an electron injection layer may be deposited using a single-molecule deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting, the present disclosure.

EXAMPLES

Synthesis Example 1

Synthesis of Compound of Chemical Formula 10

Synthesis Example 1-(1)

Synthesis of Intermediate 1-a

Intermediate 1-a was synthesized as illustrated in the following Reaction Scheme 1:

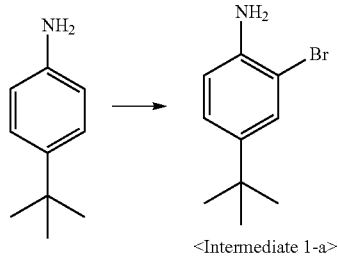

In a 2-L round-bottom flask reactor, 4-tert-butylaniline (120 g, 804 mmol) was dissolved in dimethyl formamide (960 ml). The solution was cooled to 0° C. before N-bromosuccinimide (143.1 g, 0.804 mmol) was added thereto. The reaction mixture was added with excess water, followed by extraction with ethyl acetate. The organic layer was concentrated in a vacuum and isolation by column chromatography afforded <Intermediate 1-a>. (172 g, 93.8%)

Synthesis Example 1-(2)

Synthesis of Intermediate 1-b

Intermediate 1-b was synthesized as illustrated in the following Reaction Scheme 2:

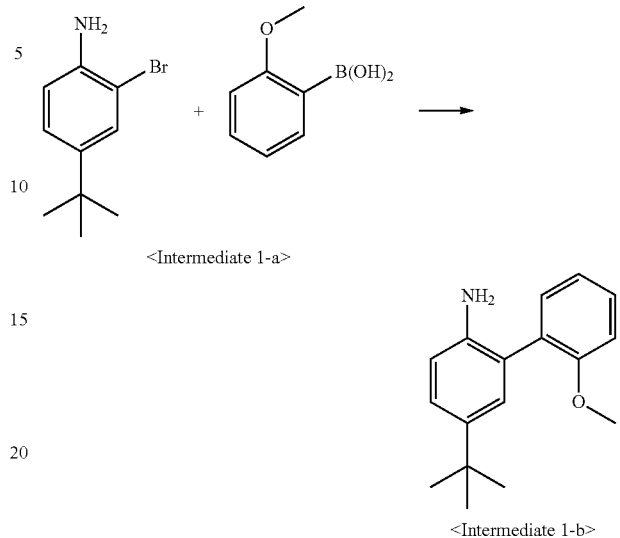

In a 2-L round-bottom flask reactor, <Intermediate 1-a> (70 g, 307 mmol), 2-methoxyphenylboronic acid (60.6 g, 0.399 mmol), tetrakis(triphenylphosphine)palladium (10.6 g, 9 mmol), potassium carbonate (84.8 g, 614 mmol), toluene (560 ml), ethanol (350 ml), and water (140 ml) were stirred for 12 hrs under reflux. After the completion of the reaction was confirmed using thin-layer chromatography, the reaction mixture was cooled to room temperature. The chilled solution was extracted with ethyl acetate and the organic layer thus obtained was concentrated in a vacuum, followed by column chromatography to isolate <Intermediate 1-b>. (70 g, 89.3%)

Synthesis Example 1-(3)

Synthesis of Intermediate 1-c

Intermediate 1-c was synthesized as illustrated in the following Reaction Scheme 3:

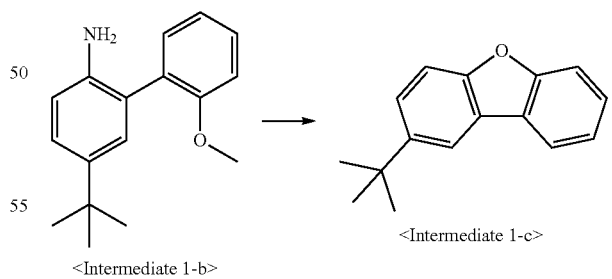

In a 1-L round-bottom flask reactor, <Intermediate 1-b> (111 g, 549 mmol) and water (444 ml) were stirred together. The reactant was gradually added with drops of sulfuric acid (106.6 g) at room temperature and then cooled to 0° C. before an aqueous sodium nitrite solution (30 g, 549 mmol) was dropwise added thereto. The reaction mixture was left for 3 hrs at 0° C. and then heated to room temperature. At room temperature, the reaction mixture was stirred. Addition of water (360 ml) induced crystallization. After filtration, the filtrate was extracted with dichloromethane and isolated by column chromatography to afford <Intermediate 1-c>. (82 g, 84.1%)

Synthesis Example 1-(4)

Synthesis of Intermediate 1-d

Intermediate 1-d was synthesized as illustrated in the following Reaction Scheme:

<Reaction Scheme 4>

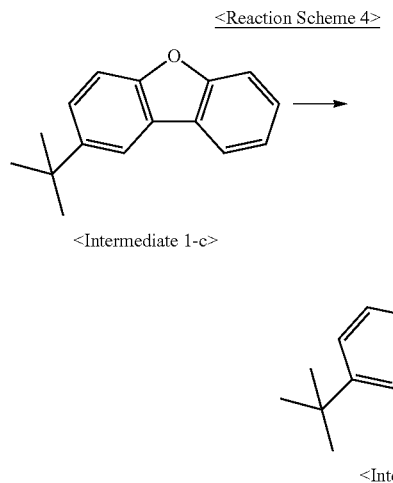

<Intermediate 1-d>

In a 1-L round-bottom flask reactor, <Intermediate 1-c> (28.4 g, 127 mmol) and tetrahydrofuran (227.2 ml) were stirred together at room temperature. Then, the temperature was reduced to −78° C., at which point normal butyl lithium (9.7 g, 152 mmol) was dropwise added. The temperature was elevated to room temperature, at which point the reaction was conducted for 12 hrs. Then, the temperature was reduced to −78° C., at which point trimethyl borate (19.7 g, 152 mmol) was dropwise added. Again, the temperature was elevated to room temperature and the completion of the reaction was confirmed using thin-layer chromatography, after which the reaction mixture was acidified with 2 N HCl and then extracted with ethyl acetate. Recrystallization in dichlorobenzene and heptane afforded <Intermediate 1-d>. (24 g, 70.7%)

Synthesis Example 1-(5)

Synthesis of Intermediate 1-e

Intermediate 1-e was synthesized as illustrated in the following Reaction Scheme 5:

<Reaction Scheme 5>

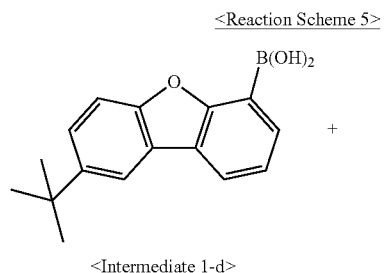

<Intermediate 1-d>

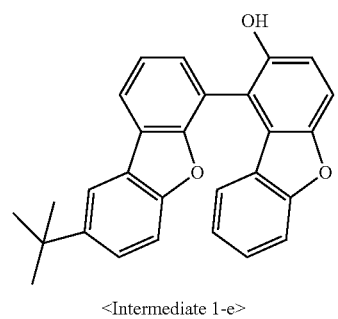

<Intermediate 1-e>

In a 500-ml round-bottom flask reactor, <Intermediate 1-d> (12.5 g, 46 mmol), 1-iodo 2-dibenzofuranol (12 g, 39 mmol), tetrakis(triphenylphosphine)palladium (1.3 g, 1 mmol), potassium carbonate (10.7 g, 77 mmol), toluene (96 ml), ethanol (60 ml), and water (24 ml) were stirred together under reflux. After the completion of the reaction was confirmed using thin-layer chromatography, the reaction mixture was extracted with ethyl acetate. The organic layer thus formed was isolated and concentrated in a vacuum. Separation by column chromatography afforded <Intermediate 1-e>. (13 g, 68.6%)

Synthesis Example 1-(6)

Synthesis of Intermediate 1-f

Intermediate 1-f was synthesized as illustrated in the following Reaction Scheme 6:

<Reaction Scheme 6>

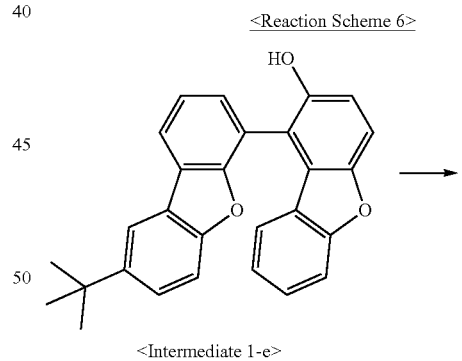

<Intermediate 1-e>

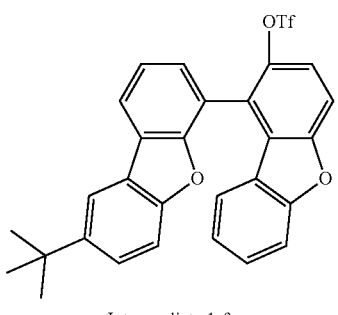

<Intermediate 1-f>

In a 500-ml round-bottom flask reactor, <Intermediate 1-e> (13 g, 32 mmol) and dichloromethane (203 ml) were stirred together under reflux and then added with pyridine (7.1 g, 96 mmol). The temperature was reduced to 0° C., at which point trifluoromethanesulfonic acid (13.5 g, 48 mmol) was dropwise added. After the completion of the reaction was confirmed using thin-layer chromatography, the reaction mixture was washed with water and stirred. After extraction with dichloromethane and water, the organic layer thus formed was concentrated and isolated through column chromatography to afford <Intermediate 1-f>. (14.5 g, 84.2%)

Synthesis Example 1-(7)

Synthesis of Intermediate 1-g

Intermediate 1-g was synthesized as illustrated in the following Reaction Scheme 7:

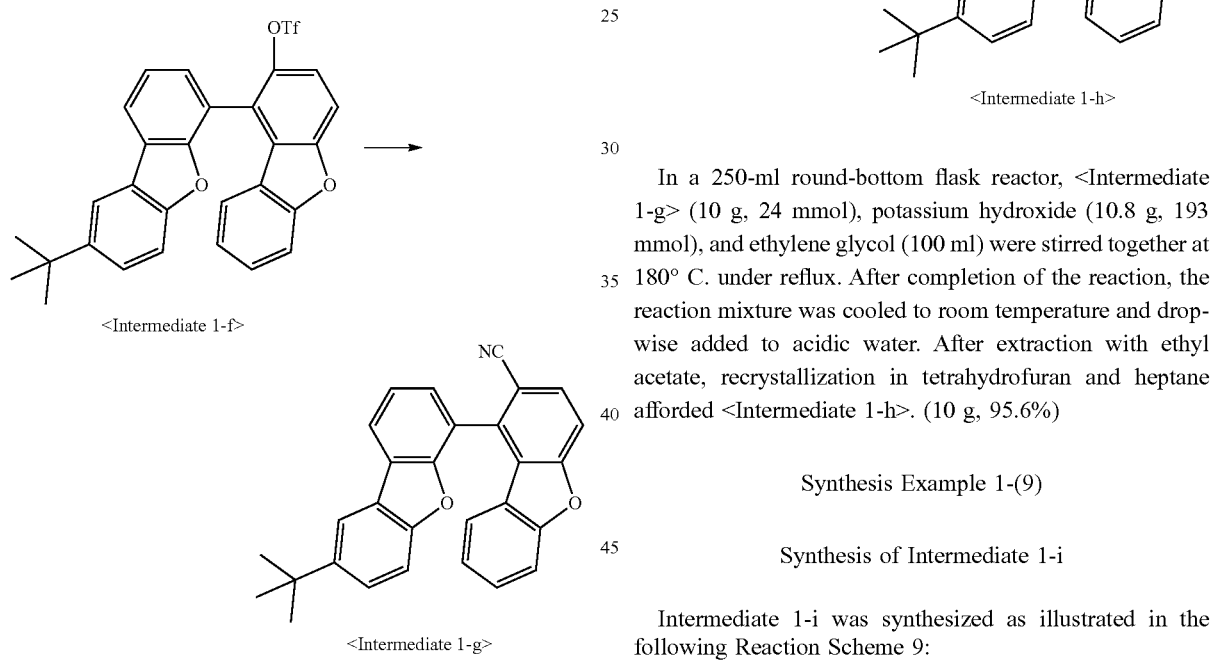

<Intermediate 1-f>

<Intermediate 1-g>

In a 250-ml round-bottom flask reactor, <Intermediate 1-f> (14 g, 26 mmol), zinc cyanide (6.1 g, 52 mmol), tetrakis(triphenylphosphine)palladium (1.2 g, 1 mmol), and dimethylformamide (84 ml) were stirred together under reflux in a nitrogen atmosphere. After completion of the reaction, the reaction mixture was cooled to room temperature and recrystallized in methanol to afford <Intermediate 1-g>. (10 g, 92.6%)

Synthesis Example 1-(8)

Synthesis of Intermediate 1-h

Intermediate 1-h was synthesized as illustrated in the following Reaction Scheme 8:

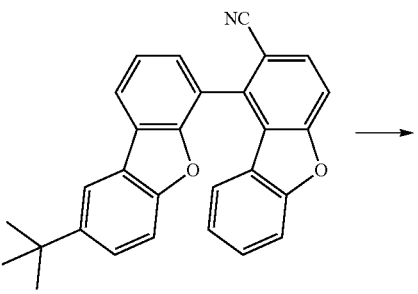

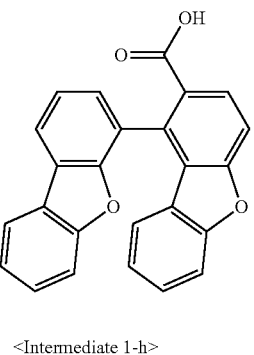

<Intermediate 1-h>

In a 250-ml round-bottom flask reactor, <Intermediate 1-g> (10 g, 24 mmol), potassium hydroxide (10.8 g, 193 mmol), and ethylene glycol (100 ml) were stirred together at 180° C. under reflux. After completion of the reaction, the reaction mixture was cooled to room temperature and dropwise added to acidic water. After extraction with ethyl acetate, recrystallization in tetrahydrofuran and heptane afforded <Intermediate 1-h>. (10 g, 95.6%)

Synthesis Example 1-(9)

Synthesis of Intermediate 1-i

Intermediate 1-i was synthesized as illustrated in the following Reaction Scheme 9:

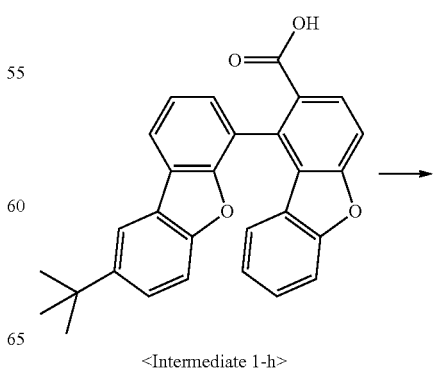

<Intermediate 1-h>

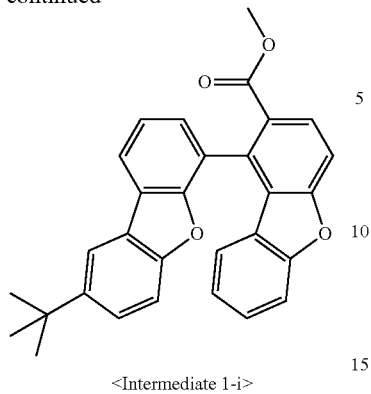

<Intermediate 1-i>

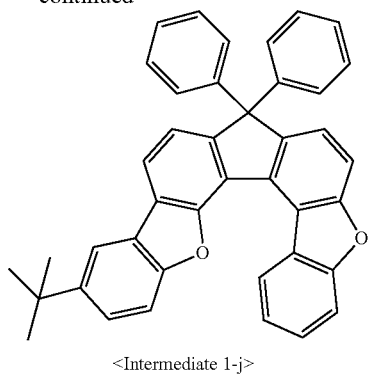

<Intermediate 1-j>

In a 250-ml round-bottom flask reactor, <Intermediate 1-h> (10 g, 23 mmol), methanol (100 ml), sulfuric acid (2 ml), and dioxane (30 ml) were stirred together under reflux. After completion of the reaction, the reaction mixture was cooled to room temperature and subjected to crystallization in excess water. Recrystallization in methanol afforded <Intermediate 1-i>. (9.5 g, 92%)

Synthesis Example 1-(10)

Synthesis of Intermediate 1-j

Intermediate 1-j was synthesized as illustrated in the following Reaction Scheme 10:

<Reaction Scheme 10>

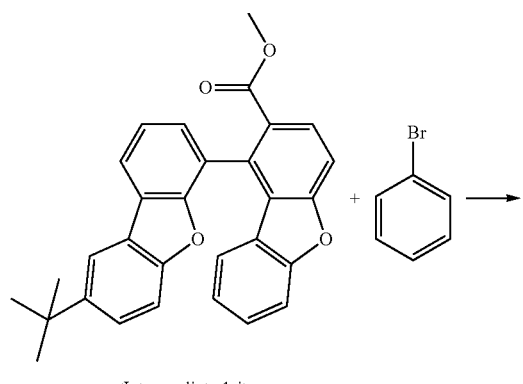

<Intermediate 1-i>

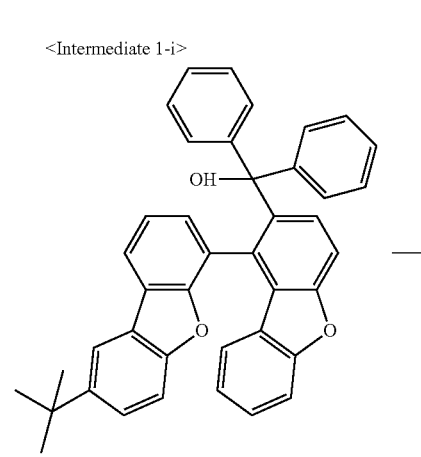

In a 250-ml round-bottom flask reactor, bromobenzene (8 g, 51 mmol) and tetrahydrofuran (64 ml) were stirred together under a nitrogen atmosphere. At −78° C., normal butyl lithium (3.1 g, 48 mmol) was dropwise added. While the low temperature was maintained, <Intermediate 1-i> (9.2 g, 20 mmol) was added and stirred. After the completion of the reaction was confirmed using thin-layer chromatography, the reaction mixture was washed with water and extracted with ethyl acetate. The organic layer thus formed was concentrated, added with acetone (80 ml) and HCl (0.8 ml), and stirred at 40° C. Subsequent to filtration, recrystallization in methanol and toluene afforded <Intermediate 1-j>. (9.2 g, 80.9%)

Synthesis Example 1-(11)

Synthesis of Intermediate 1-k

Intermediate 1-k was synthesized as illustrated in the following Reaction Scheme 11:

<Reaction Scheme 11>

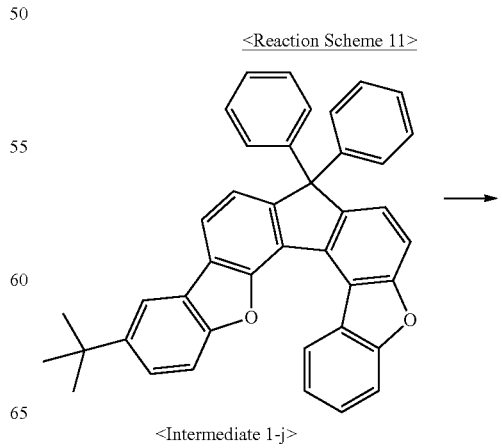

<Intermediate 1-j>

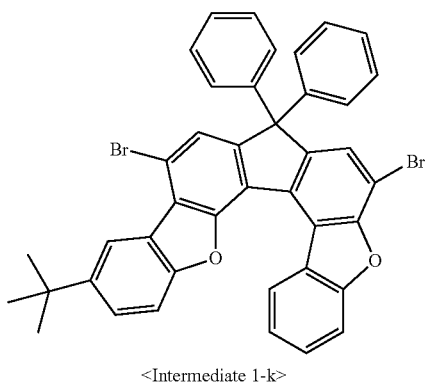

<Intermediate 1-k>

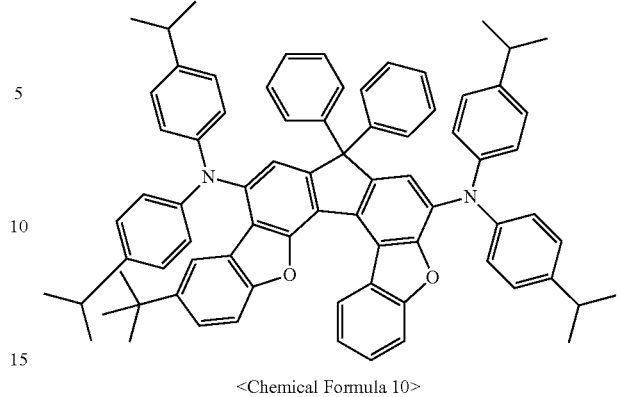

<Chemical Formula 10>

In a 250-ml round-bottom flask reactor, <Intermediate 1-j> (9.2 g, 17 mmol) and dichloromethane (230 ml) were stirred together. Drops of bromine (8 g, 50 mmol) were slowly added. After completion of the reaction, recrystallization in tetrahydrofuran and acetone afforded <Intermediate 1-k>. (5.8 g, 49.1%)

Synthesis Example 1-(12)

Synthesis of Compound of Chemical Formula 10

The compound of Chemical Formula 10 was synthesized as illustrated in the following Reaction Scheme 12:

<Reaction Scheme 12>

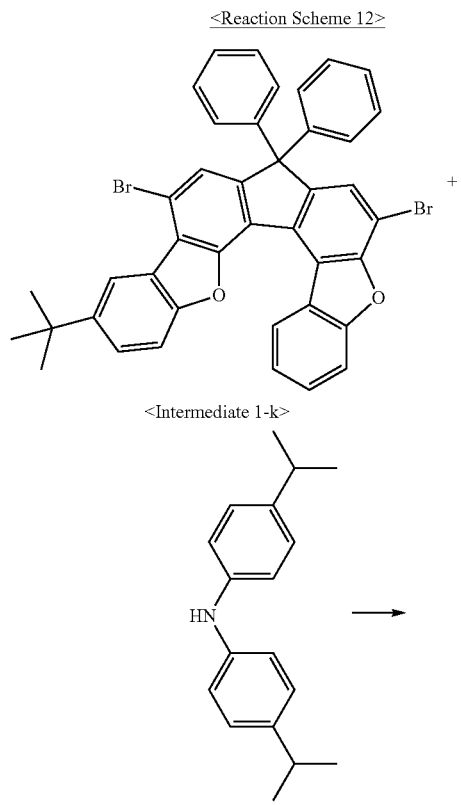

In a 250-ml round-bottom flask reactor, <Intermediate 1-k> (5.8 g, 8 mmol), dicumyl diphenylamine (4.8 g, 19 mmol), bis(dibenzylideneacetone)palladium (0.3 g, 0.1 mmol), tri-butylphosphine (0.3 g, 1 mmol), and sodium tert-butoxide (23.2 g, 241 mmol) were stirred together. After the completion of the reaction was confirmed using thin-layer chromatography, the reaction mixture was hot filtered with toluene. Recrystallization in dichloromethane and acetone afforded the compound of <Chemical Formula 10>. (4.2 g, 46.3%)

MS (MALDI-TOF):m/z 1156.56 [M⁺]

Synthesis Example 2

Synthesis of Compound of Chemical Formula 14

Synthesis Example 2-(1)

Synthesis of Intermediate 2-a

Intermediate 2-a was synthesized as illustrated in the following Reaction Scheme 13:

<Reaction Scheme 13>

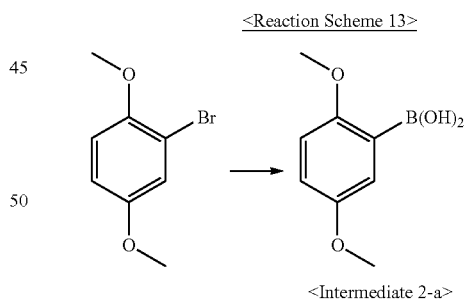

<Intermediate 2-a>

In a 1-L round-bottom flask reactor, 2-bromo-1,4-dimethoxybenzene (50 g, 230 mmol) was dissolved in tetrahydrofuran (400 ml) under a nitrogen atmosphere. The temperature was reduced to −78° C., at which point normal butyl lithium (167 ml, 280 mmol) was dropwise added. The solution was stirred for 2 hrs at the same temperature, added with trimethyl borate (36 ml, 320 mmol), and then stirred again overnight at room temperature. After completion of the reaction, drops of 2 N HCl were slowly added to acidify the reaction mixture. Subsequent to extraction with water and ethyl acetate, the organic layer thus formed was separated and dried over magnesium sulfate. The residue was concentrated in a vacuum and recrystallized in heptane and toluene to afford <Intermediate 2-a>. (14.2 g, 34%)

Synthesis Example 2-(2)

Synthesis of Intermediate 2-b

Intermediate 2-b was synthesized as illustrated in the following Reaction Scheme 14:

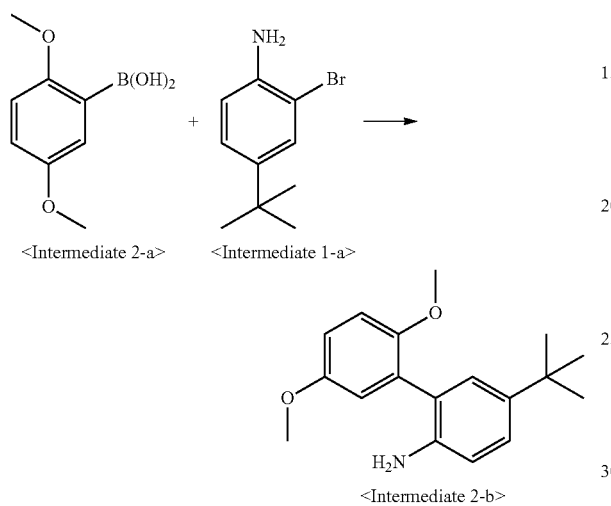

<Reaction Scheme 14>

<Intermediate 2-a>    <Intermediate 1-a>

<Intermediate 2-b>

The same procedure was conducted as in Synthesis Example 1-(2), with the exception of using <Intermediate 2-a> instead of 2-methoxyphenylboronic acid, to synthesize <Intermediate 2-b>. (14.5 g, 65%)

Synthesis Example 2-(3)

Synthesis of Intermediate 2-c

Intermediate 2-c was synthesized as illustrated in the following Reaction Scheme 15:

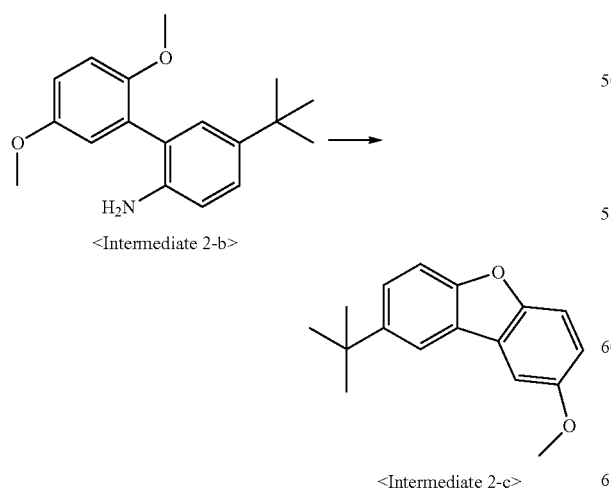

<Reaction Scheme 15>

<Intermediate 2-b>

<Intermediate 2-c>

The same procedure was conducted as in Synthesis Example 1-(3), with the exception of using <Intermediate 2-b> instead of <Intermediate 1-b>, to synthesize <Intermediate 2-c>. (11 g, 85%)

Synthesis Example 2-(4)

Synthesis of Intermediate 2-d

Intermediate 2-d was synthesized as illustrated in the following Reaction Scheme 16:

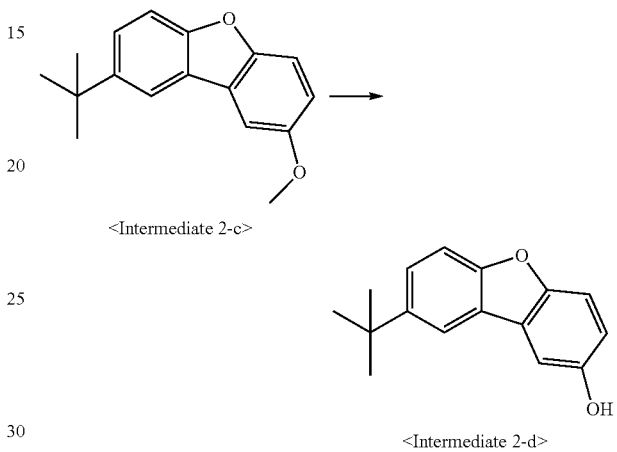

<Reaction Scheme 16>

<Intermediate 2-c>

<Intermediate 2-d>

In a 250-mL round-bottom flask reactor, <Intermediate 2-c> (11 g, 43 mmol), hydrogen bromic acid (8.4 g, 104 mmol) and acetic acid (132 ml) were stirred together. The reactants were stirred together with excess water at room temperature. After completion of the reaction, the reaction mixture was dissolved in ethyl acetate and recrystallized in heptane to afford <Intermediate 2-d>. (10 g, 96%)

Synthesis Example 2-(5)

Synthesis of Intermediate 2-e

Intermediate 2-e was synthesized as illustrated in the following Reaction Scheme 17:

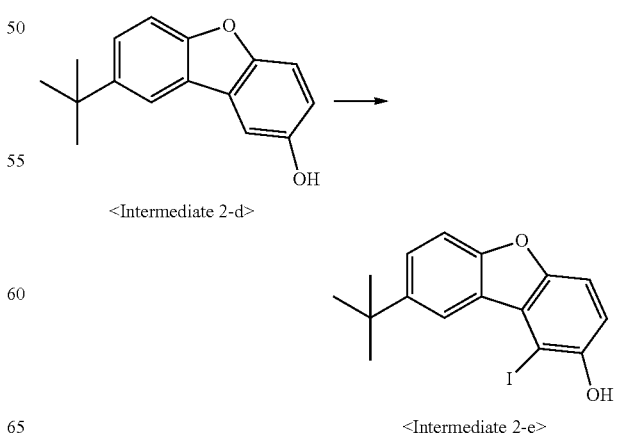

<Reaction Scheme 17>

<Intermediate 2-d>

<Intermediate 2-e>

In a 250-mL round-bottom flask reactor, <Intermediate 2-d> (10 g, 42 mmol) was dissolved in acetic acid (70 ml). A solution of iodine monochloride (7.4 g, 46 mmol) in HCl (13 ml) was dropwise added. The reactor containing the reactants was wrapped with aluminum foil, the reactants were stirred. After completion of the reaction, the reaction mixture was extracted with water and dichloromethane. The organic layer thus formed was separated and concentrated in a vacuum. Column chromatography isolated <Intermediate 2-e>. (12 g, 79%)

Synthesis Example 2-(6)

Synthesis of Intermediate 2-f

Intermediate 2-f was synthesized as illustrated in Reaction Scheme 5 to 11.

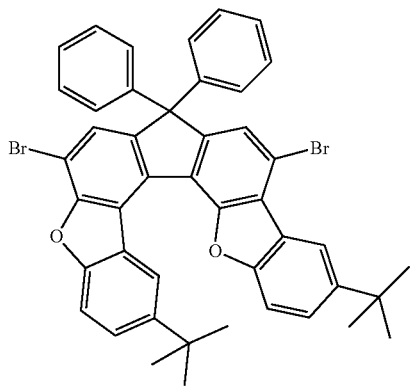

<Intermediate 2-f>

The same procedure was conducted as in Synthesis Examples 1-(5) to 1-(11), with the exception of using <Intermediate 2-e> instead of 1-iodo 2-dibenzofuranol in Synthesis Example 1-(5), to synthesize <Intermediate 2-f>. (4.4 g, 87%)

Synthesis Example 2-(7)

Synthesis of Intermediate 2-g

Intermediate 2-g was synthesized as illustrated in the following Reaction Scheme 18:

<Reaction Scheme 18>

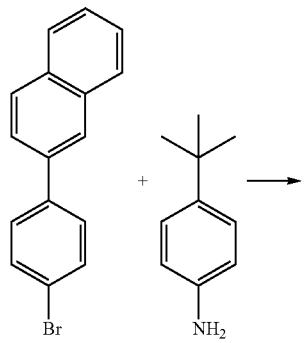

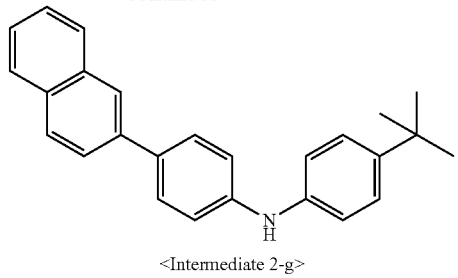

<Intermediate 2-g>

In a 250-ml round-bottom flask reactor, 1-bromo-4-(2-naphthyl)benzene (10.0 g, 0.035 mol), 4-tert-butylaniline (5.8 g, 0.039 mol), tris(dibenzylideneacetone)dipalladium (0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer thus formed was separated, dried over magnesium sulfate, and concentrated in a vacuum. Isolation through column chromatography afforded <Intermediate 2-g>. (10 g, 80%)

Synthesis Example 2-(8)

Synthesis of Compound of Chemical Formula 14

The compound of Chemical Formula 14 was synthesized as illustrated in the following Reaction Scheme 19:

<Reaction Scheme 19>

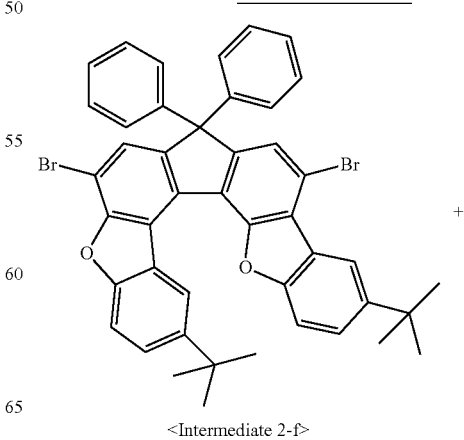

<Intermediate 2-f>

+

-continued

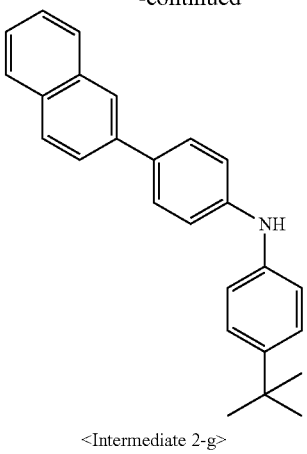

<Intermediate 2-g>

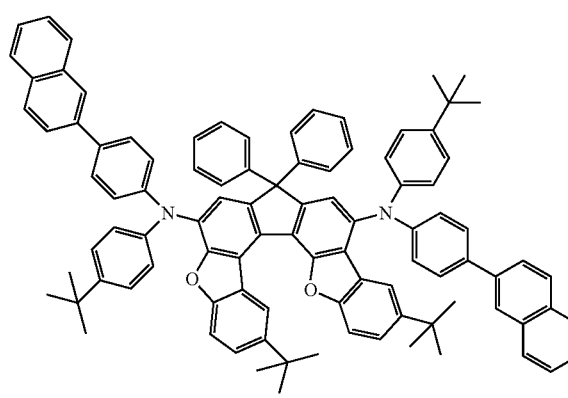

<Chemical Formula 14>

The same procedure was conducted as in Synthesis Example 1-(12), with the exception of using <Intermediate 2-f> and <Intermediate 2-g> instead of <Intermediate 1-k> and dicumyl diphenyl amine, respectively, to synthesize the compound of <Chemical Formula 15>. (5.1 g, 61%)

MS (MALDI-TOF):m/z 1309.66 [M$^+$]

Synthesis Example 3

Synthesis of Compound of Chemical Formula 15

Synthesis Example 3-(1)

Synthesis of Compound of Chemical Formula 15

The compound of Chemical Formula 15 was synthesized as illustrated in the following Reaction Scheme 20:

<Reaction Scheme 20>

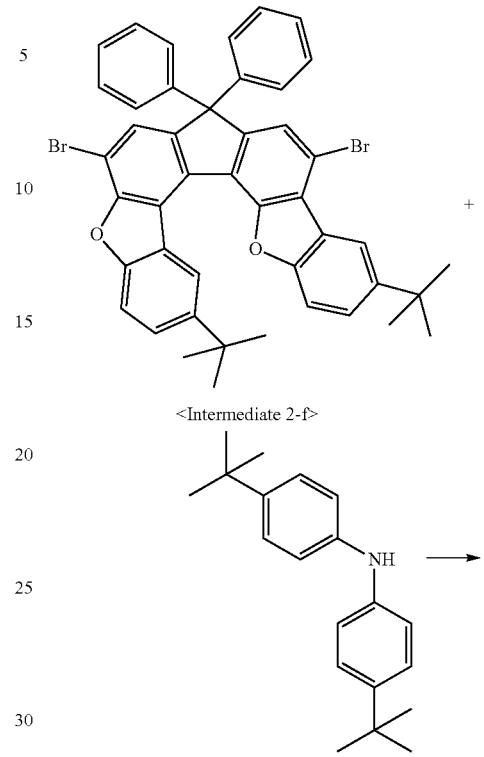

<Intermediate 2-f>

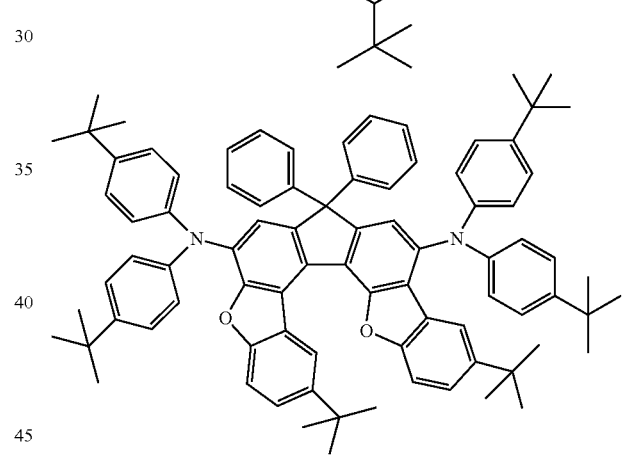

<Chemical Formula 15>

The same procedure was conducted as in Synthesis Example 1-(12), with the exception of using <Intermediate 2-f> and bis(4-tert-butylphenyl)amine instead of <Intermediate 1-k> and dicumyl diphenyl amine, respectively, to synthesize the compound of <Chemical Formula 15>. (5.1 g, 61%)

MS (MALDI-TOF):m/z 1168.68 [M$^+$]

Synthesis Example 4

Synthesis of Compound of Chemical Formula 20

Synthesis Example 4-(1)

Synthesis of Intermediate 4-a

Intermediate 3-a was synthesized as illustrated in the following Reaction Scheme 21:

<Reaction Scheme 21>

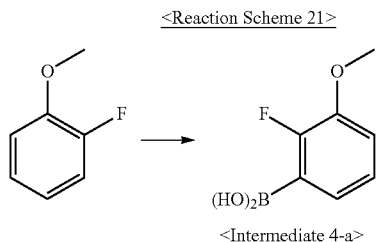

<Intermediate 4-a>

The same procedure was conducted as in Synthesis Example 1-(4), with the exception of using 2-fluoroanisole instead of <Intermediate 1-c>, to synthesize <Intermediate 4-a>. (81 g, 60%)

Synthesis Example 4-(2)

Synthesis of Intermediate 4-b

Intermediate 4-b was synthesized as illustrated in the following Reaction Scheme 22:

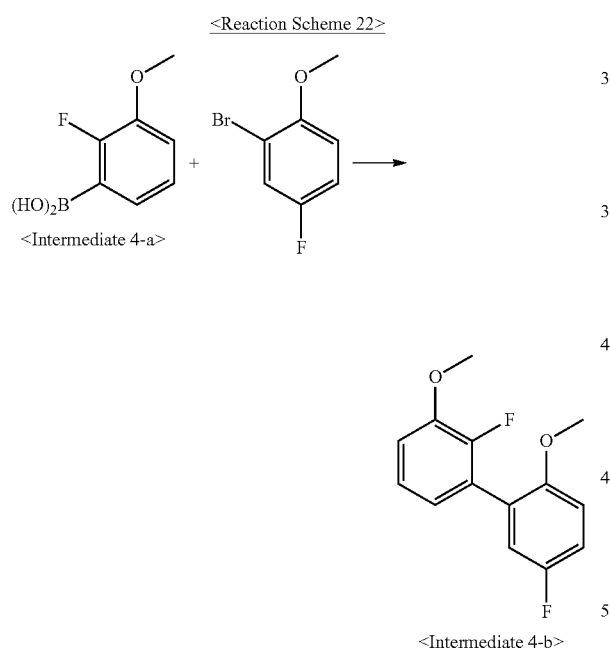

<Reaction Scheme 22>

<Intermediate 4-a>

<Intermediate 4-b>

The same procedure was conducted as in Synthesis Example 1-(2), with the exception of using 2-bromo-4-fluoro-1-methoxy benzene and <Intermediate 4-a> instead of <Intermediate 1-a> and 2-methoxyphenylboronic acid, respectively, to synthesize <Intermediate 4-b>. (84 g, 70%)

Synthesis Example 4-(3)

Synthesis of Intermediate 4-c

Intermediate 4-c was synthesized as illustrated in the following Reaction Scheme 23:

<Reaction Scheme 23>

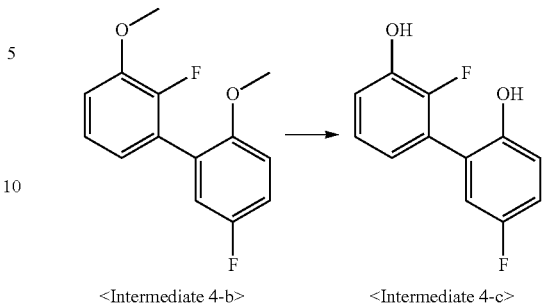

<Intermediate 4-b>   <Intermediate 4-c>

The same procedure was conducted as in Synthesis Example 2-(4), with the exception of using <Intermediate 4-b> instead of <Intermediate 2-c>, to synthesize <Intermediate 4-c>. (72 g, 97%)

Synthesis Example 4-(4)

Synthesis of Intermediate 4-d

Intermediate 4-d was synthesized as illustrated in the following Reaction Scheme 24:

<Reaction Scheme 24>

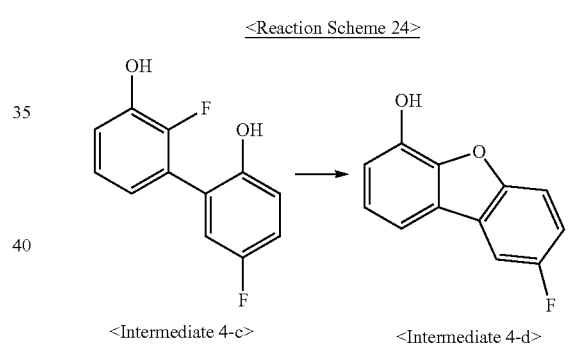

<Intermediate 4-c>   <Intermediate 4-d>

In a 1-L round-bottom flask reactor, <Intermediate 4-c> (72 g, 288 mmol), hydrogen bromic acid (116.4 g, 1.439 mol), and acetic acid (432 g) were stirred together under reflux. After completion of the reaction was confirmed using thin-layer chromatography, the reaction mixture was cooled to room temperature and extracted with water. The organic layer was separated, concentrated in a vacuum, and purified by column chromatography to afford <Intermediate 4-d>. (55 g, 84%)

Synthesis Example 4-(5)

Synthesis of Intermediate 4-e

Intermediate 4-e was synthesized as illustrated in the following Reaction Scheme 25:

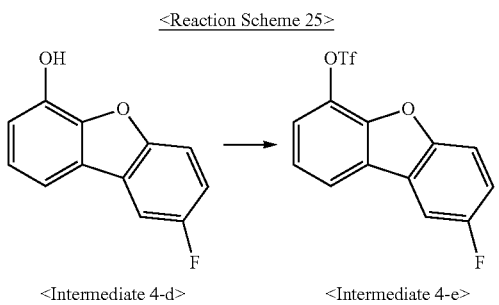 [SMILES: Oc1cccc2c1oc1ccc(F)cc12 ; O=S(=O)(Oc1cccc2c1oc1ccc(F)cc12)C(F)(F)F]

The same procedure was conducted as in Synthesis Example 1-(6), with the exception of using <Intermediate 4-d> instead of <Intermediate 1-e>, to synthesize <Intermediate 4-e>. (57 g, 63%)

Synthesis Example 4-(6)

Synthesis of Intermediate 4-f

Intermediate 4-f was synthesized as illustrated in the following Reaction Scheme 26:

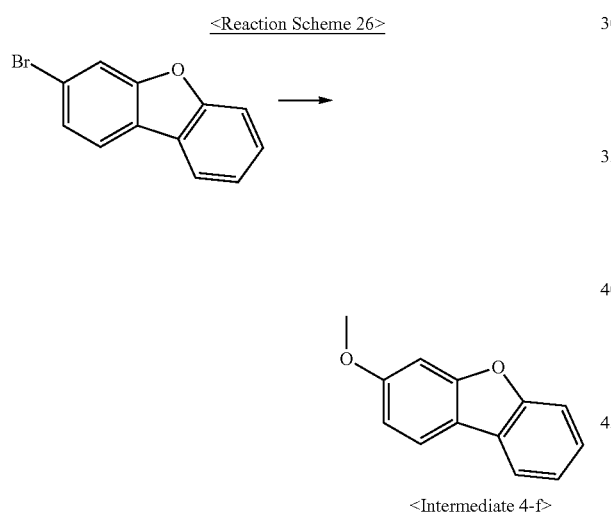

In a 1-L round-bottom flask reactor, 3-bromodibenzofuran (100 g, 405 mmol), copper bromide (5.8 g, 40 mmol), sodium methoxide (109.3 g, 2.024 mol), dimethylformamide (800 ml), and methanol (200 ml) were stirred together under reflux. The reaction mixture was cooled to room temperature and crystalized in water, followed by filtration. The filtrate was concentrated and recrystallized in heptane to afford <Intermediate 4-f>. (74 g, 92%)

Synthesis Example 4-(7)

Synthesis of Intermediate 4-g

Intermediate 4-g was synthesized as illustrated in the following Reaction Scheme 27:

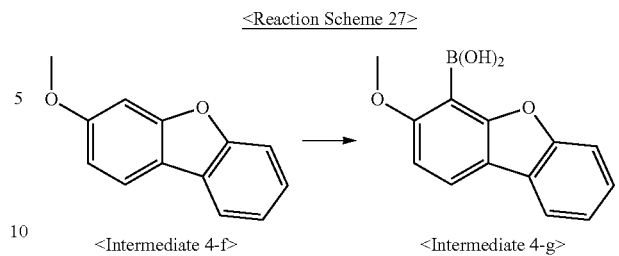

The same procedure was conducted as in Synthesis Example 1-(4), with the exception of using <Intermediate 4-f> instead of <Intermediate 1-c>, to synthesize <Intermediate 4-g>. (71 g, 79%)

Synthesis Example 4-(8)

Synthesis of Intermediate 4-h

Intermediate 4-h was synthesized as illustrated in the following Reaction Scheme 28:

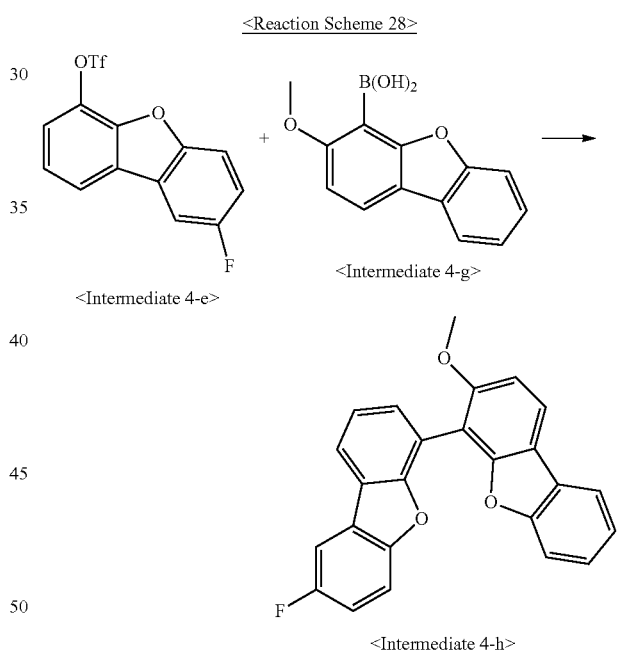

The same procedure was conducted as in Synthesis Example 1-(5), with the exception of using <Intermediate 4-g> and <Intermediate 4-e> instead of <Intermediate 1-d> and 1-iodo 2-dibenzofuranol, respectively, to synthesize <Intermediate 4-h>. (55 g, 84%)

Synthesis Example 4-(9)

Synthesis of Intermediate 4-i

Intermediate 4-i was synthesized as illustrated in the following Reaction Scheme 29:

<Reaction Scheme 29>

<Intermediate 4-h>

<Intermediate 4-i>

The same procedure was conducted as in Synthesis Example 2-(4), with the exception of using <Intermediate 4-h> instead of <Intermediate 2-c>, to synthesize <Intermediate 4-i>. (41 g, 77%)

Synthesis Example 4-(10)

Synthesis of Intermediate 4-j

Intermediate 4-j was synthesized as illustrated in Reaction Scheme 6 to 11.

<Intermediate 4-j>

The same procedure was conducted as in Synthesis Examples 1-(6) to 1-(11), with the exception of using <Intermediate 4-i> instead of <Intermediate 1-e> in Synthesis Example 1-(6), to synthesize <Intermediate 4-j>. (11 g, 73%)

Synthesis Example 4-(11)

Synthesis of Intermediate 4-k

Intermediate 4-k was synthesized as illustrated in the following Reaction Scheme 30:

<Reaction Scheme 30>

<Intermediate 4-k>

The same procedure was conducted as in Synthesis Example 2-(13), with the exception of using 1-bromo-4-(trimethylsilyl)benzene instead of 1-bromo 4-(2-naphthyl)benzene, to synthesize <Intermediate 4-k> (13.1 g, 72.1%).

Synthesis Example 4-(12)

Synthesis of Compound of Chemical Formula 20

The compound of Chemical Formula 20 was synthesized as illustrated in the following Reaction Scheme 31:

<Reaction Scheme 31>

<Intermediate 4-j>

-continued

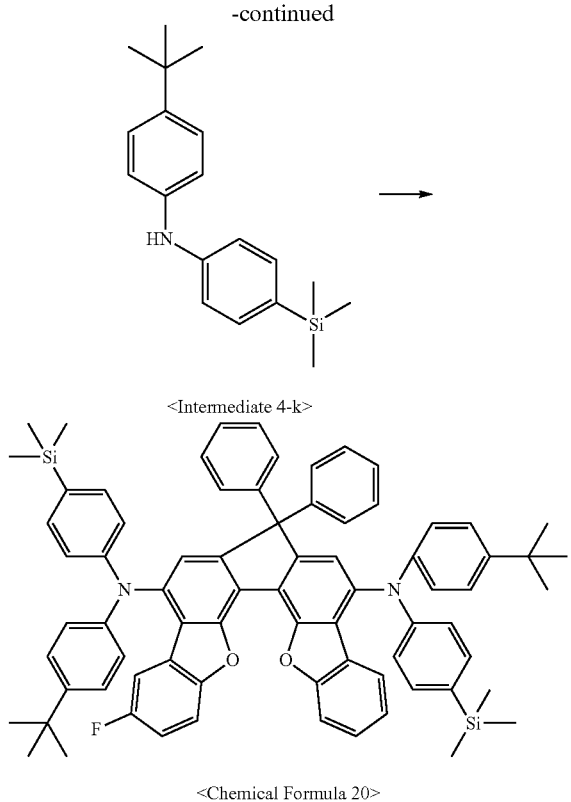

<Chemical Formula 20>

The same procedure was conducted as in Synthesis Example 1-(12), with the exception of using <Intermediate 4-j> and <Intermediate 4-k> instead of <Intermediate 1-k> and dicumyl diphenyl amine, respectively, to synthesize the compound of <Chemical Formula 20>. (12 g, 62%)
MS (MALDI-TOF):m/z 1106.50 [M⁺]

Synthesis Example 5

Synthesis of Compound of Chemical Formula 24

Synthesis Example 5-(1)

Synthesis of Intermediate 5-a

Intermediate 5-a was synthesized as illustrated in Reaction Scheme 6 to 9.

The same procedure was conducted as in Synthesis Examples 1-(6) to 1-(9), with the exception of using <Intermediate 4-i> instead of <Intermediate 1-e> in Synthesis Example 1-(6), to synthesize <Intermediate 5-a>. (33 g, 69%)

Synthesis Example 5-(2)

Synthesis of Intermediate 5-b

Intermediate 5-b was synthesized as illustrated in the following Reaction Scheme 32:

<Reaction Scheme 32>

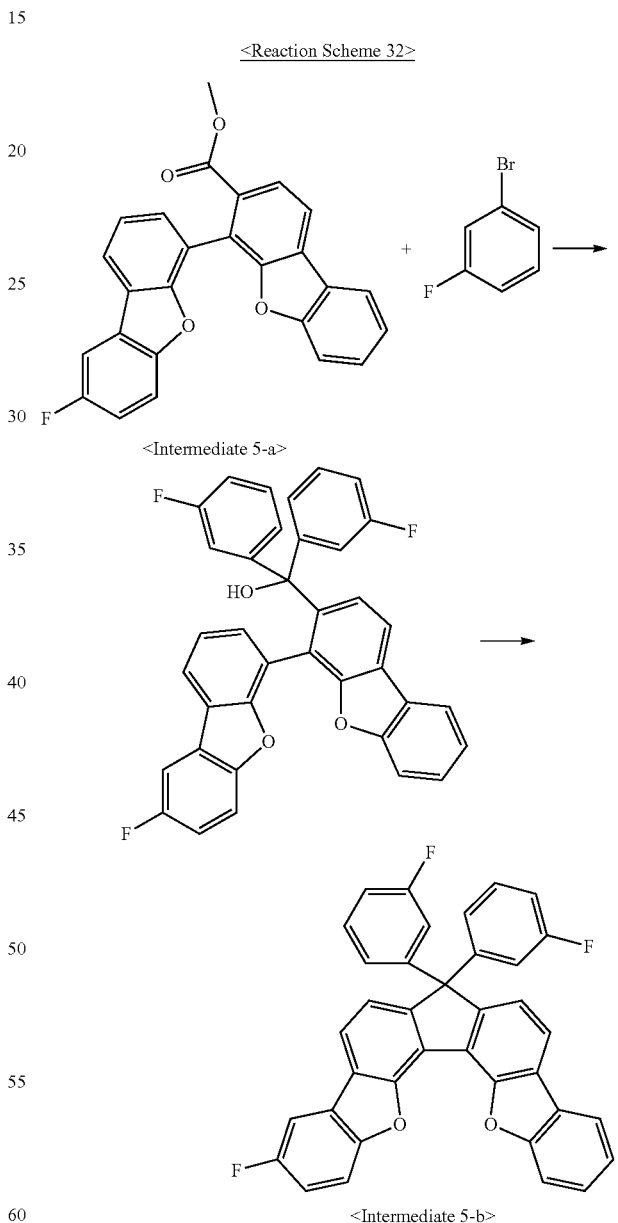

The same procedure was conducted as in Synthesis Example 1-(10), with the exception of using <Intermediate 5-a> and 3-fluorobromobenzene instead of <Intermediate 1-i> and bromobenzene, respectively, to synthesize <Intermediate 5-b>. (12.3 g, 52%)

Synthesis Example 5-(3)

Synthesis of Intermediate 5-c

Intermediate 5-c was synthesized as illustrated in the following Reaction Scheme 33:

<Reaction Scheme 33>

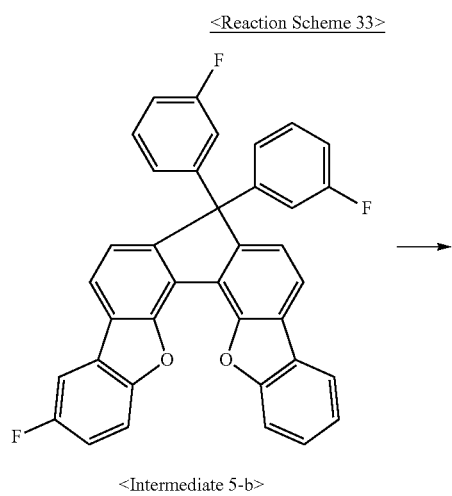

<Intermediate 5-b>

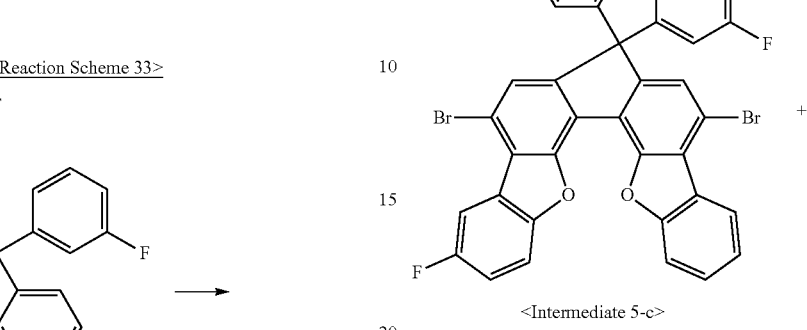

<Intermediate 5-c>

The same procedure was conducted as in Synthesis Example 1-(11), with the exception of using <Intermediate 5-b> instead of <Intermediate 1-j>, to synthesize <Intermediate 5-c>. (14 g, 66%)

Synthesis Example 5-(4)

Synthesis of Compound of Chemical Formula 24

The compound of Chemical Formula 24 was synthesized as illustrated in the following Reaction Scheme 34:

<Reaction Scheme 34>

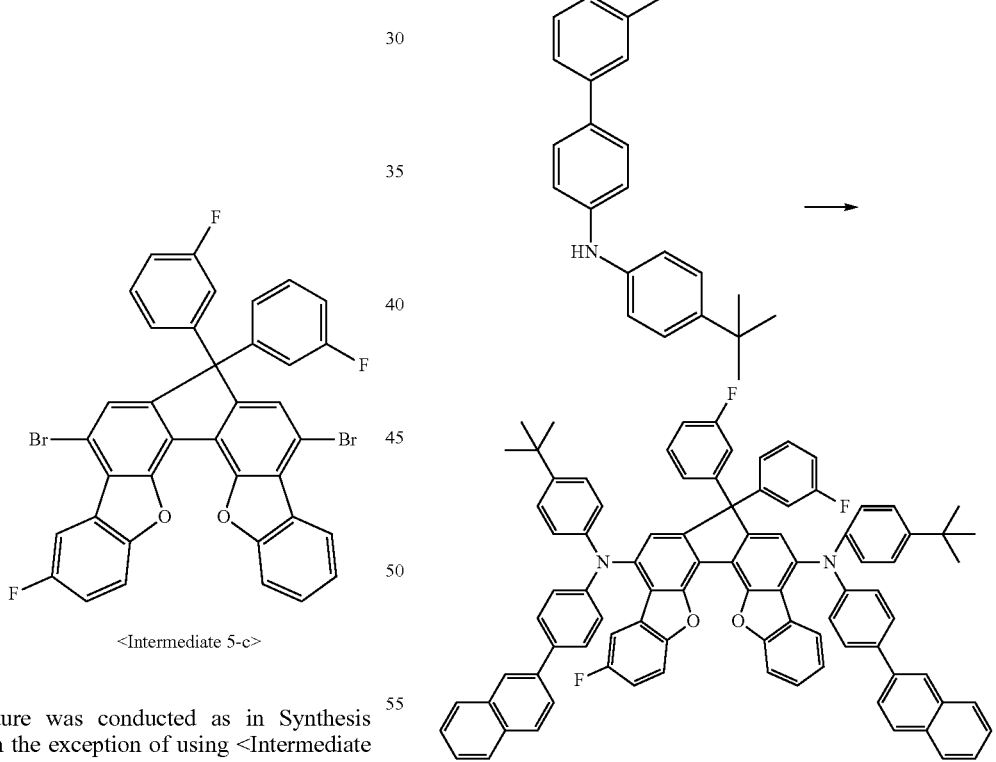

<Chemical Formula 24>

The same procedure was conducted as in Synthesis Example 1-(12), with the exception of using <Intermediate 5-c> and <Intermediate 2-g> instead of <Intermediate 1-k> and dicumyl diphenyl amine, to synthesize the compound of <Chemical Formula 24>. (12 g, 62%)

MS (MALDI-TOF):m/z 1250.50 [M$^+$]

Synthesis Example 6

Synthesis of Compound of Chemical Formula 44

Synthesis Example 6-(1)

Synthesis of Intermediate 6-a

Intermediate 6-a was synthesized as illustrated in the following Reaction Scheme 35:

<Reaction Scheme 35>

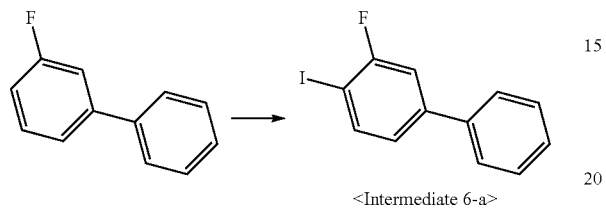

<Intermediate 6-a>

The same procedure was conducted as in Synthesis Example 2-(5), with the exception of using 3-fluorobiphenyl instead of <Intermediate 2-d>, to synthesize <Intermediate 6-a>. (53 g, 71%)

Synthesis Example 6-(2)

Synthesis of Intermediate 6-b

Intermediate 6-b was synthesized as illustrated in the following Reaction Scheme 36:

<Reaction Scheme 36>

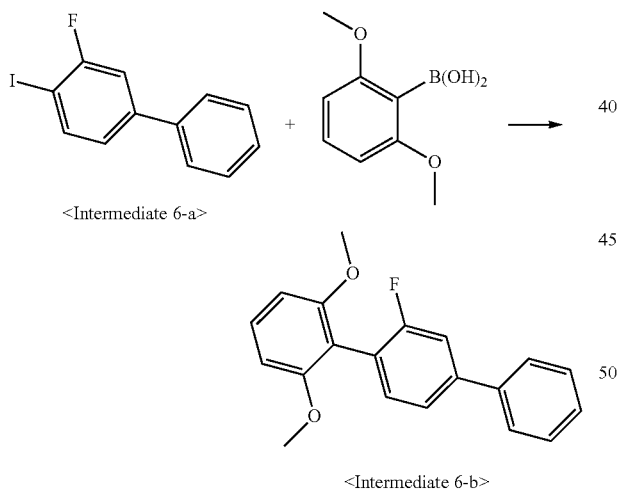

<Intermediate 6-b>

The same procedure was conducted as in Synthesis Example 1-(5), with the exception of using 2,6-dimethoxyphenyl boronic acid and <Intermediate 6-a> instead of <Intermediate 1-d> and 1-iodo 2-dibenzofuranol, respectively, to synthesize <Intermediate 6-b>. (48 g, 76%)

Synthesis Example 6-(3)

Synthesis of Intermediate 6-c

Intermediate 6-c was synthesized as illustrated in the following Reaction Scheme 37:

<Reaction Scheme 37>

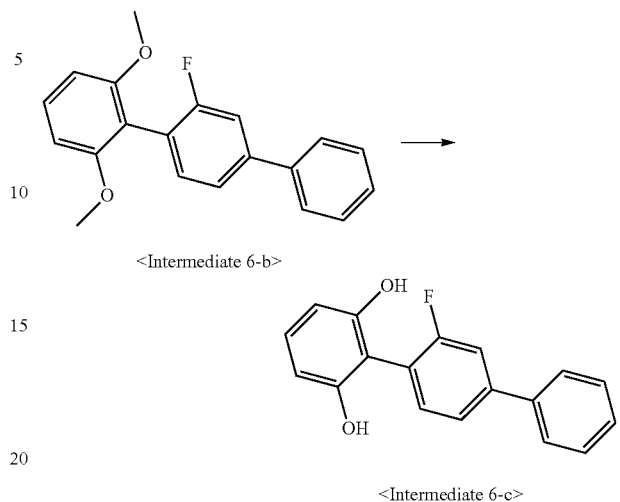

<Intermediate 6-c>

The same procedure was conducted as in Synthesis Example 2-(4), with the exception of using instead of <Intermediate 2-c>, to synthesize <Intermediate 6-c>. (52 g, 69%)

Synthesis Example 6-(4)

Synthesis of Intermediate 6-d

Intermediate 6-d was synthesized as illustrated in the following Reaction Scheme 38:

<Reaction Scheme 38>

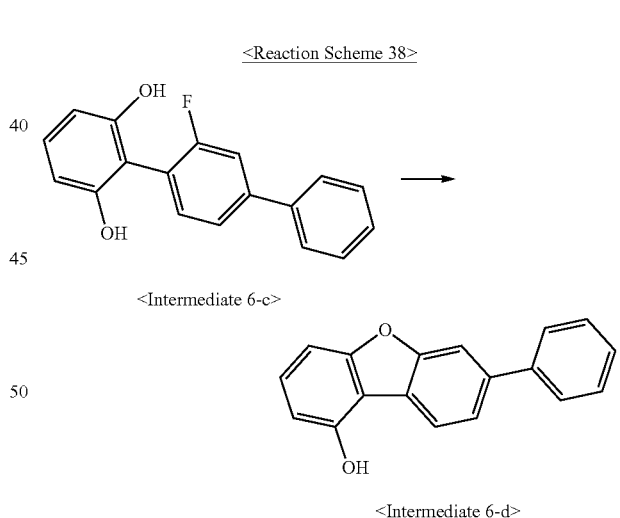

<Intermediate 6-d>

The same procedure was conducted as in Synthesis Example 6-(4), with the exception of using <Intermediate 6-c> instead of <Intermediate 3-c>, to synthesize <Intermediate 6-d>. (36 g, 52%)

Synthesis Example 6-(5)

Synthesis of Intermediate 6-e

Intermediate 6-e was synthesized as illustrated in the following Reaction Scheme 39:

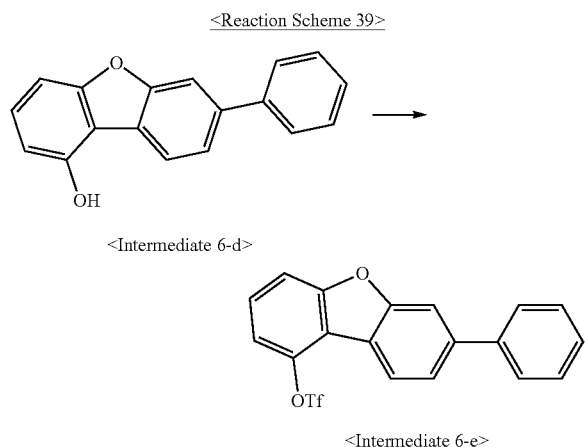

<Reaction Scheme 39>

<Intermediate 6-d>

<Intermediate 6-e>

The same procedure was conducted as in Synthesis Example 1-(6), with the exception of using <Intermediate 6-d> instead of <Intermediate 1-e>, to synthesize <Intermediate 6-e>. (42 g, 66%)

Synthesis Example 6-(6)

Synthesis of Intermediate 6-f

Intermediate 6-f was synthesized as illustrated in the following Reaction Scheme 40:

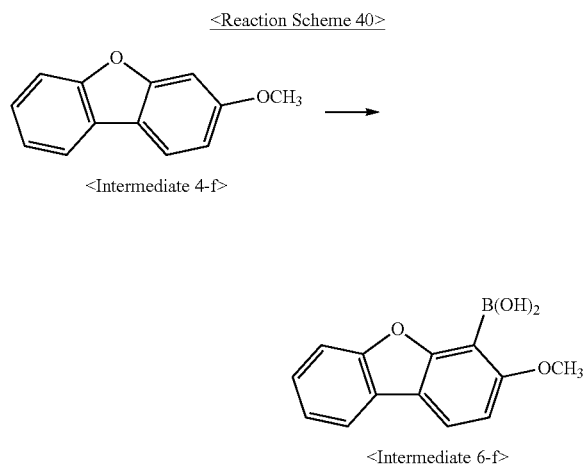

<Reaction Scheme 40>

<Intermediate 4-f>

<Intermediate 6-f>

The same procedure was conducted as in Synthesis Example 1-(4), with the exception of using <Intermediate 4-f> instead of <Intermediate 1-c>, to synthesize <Intermediate 6-f>. (22 g, 45%)

Synthesis Example 6-(7)

Synthesis of Intermediate 6-g

Intermediate 6-g was synthesized as illustrated in the following Reaction Scheme 41:

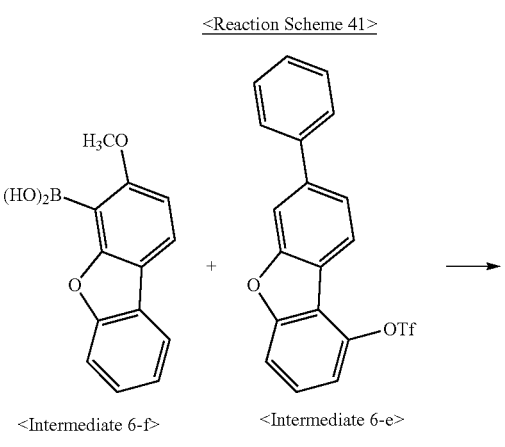

<Reaction Scheme 41>

<Intermediate 6-f> + <Intermediate 6-e>

<Intermediate 6-g>

The same procedure was conducted as in Synthesis Example 1-(5), with the exception of using <Intermediate 6-f> and <Intermediate 6-e> instead of <Intermediate 1-d> and 1-iodo 2-dibenzofuranol, respectively, to synthesize <Intermediate 6-g>. (17 g, 63%)

Synthesis Example 6-(8)

Synthesis of Intermediate 6-h

Intermediate 6-h was synthesized as illustrated in the following Reaction Scheme 42:

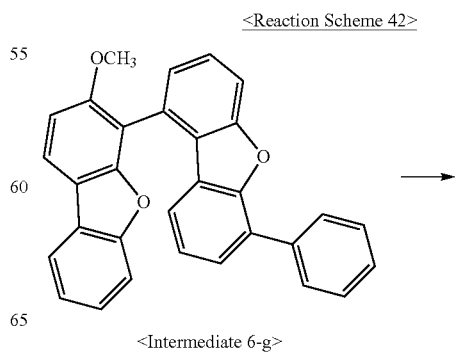

<Reaction Scheme 42>

<Intermediate 6-g>

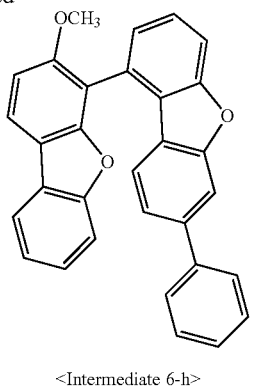

<Intermediate 6-h>

The same procedure was conducted as in Synthesis Example 2-(4), with the exception of using <Intermediate 6-g> instead of <Intermediate 2-c>, to synthesize <Intermediate 6-h>. (10.2 g, 72%)

Synthesis Example 6-(9)

Synthesis of Intermediate 6-i

Intermediate 6-i was synthesized as illustrated in Reaction Scheme 6 to 11.

<Intermediate 6-i>

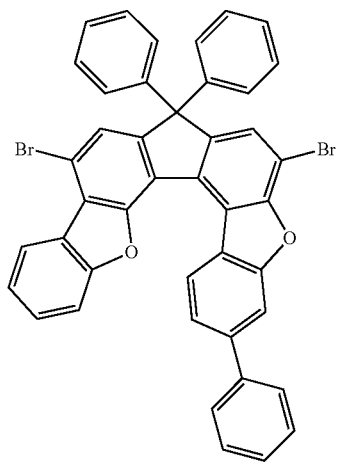

The same procedure was conducted as in Synthesis Examples 1-(6) to 1-(11), with the exception of using <Intermediate 6-h> instead of <Intermediate 1-e> in Synthesis Example 1-(6), to synthesize <Intermediate 6-i>. (20.5 g, 78%)

Synthesis Example 6-(10)

Synthesis of Compound of Chemical Formula 44

The compound of Chemical Formula 44 was synthesized as illustrated in the following Reaction Scheme 43:

<Reaction Scheme 43>

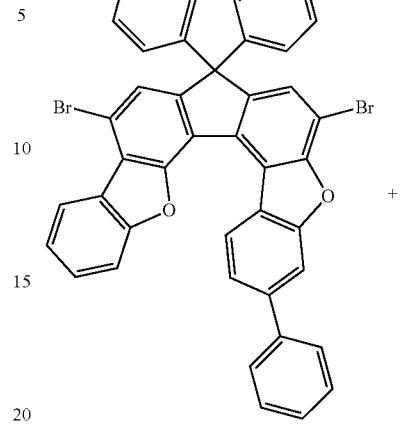

<Intermediate 6-i>

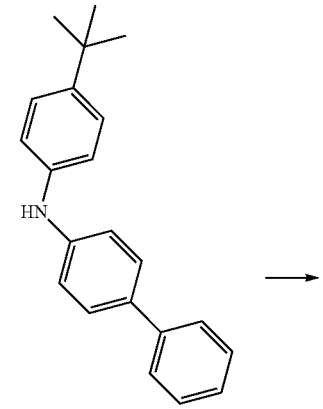

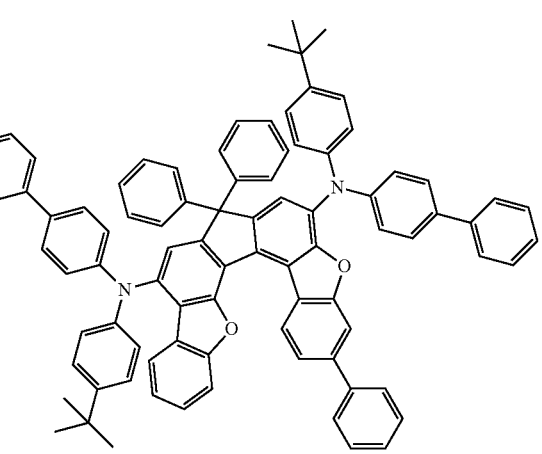

<Chemical Formula 44>

The same procedure was conducted as in Synthesis Example 1-(12), with the exception of using <Intermediate 6-i> and N-(4-(tert-butyl)phenyl)-[1,1'-biphenyl]-4-amine instead of <Intermediate 1-k> and dicumyl diphenyl amine, respectively, to synthesize the compound of <Chemical Formula 44>. (19 g, 66%)

MS (MALDI-TOF):m/z 1172.53[M$^+$]

Synthesis Example 7

Synthesis of Compound of Chemical Formula 49

Synthesis Example 7-(1)

Synthesis of Intermediate 7-a

Intermediate 7-a was synthesized as illustrated in Reaction Scheme 33 to 36.

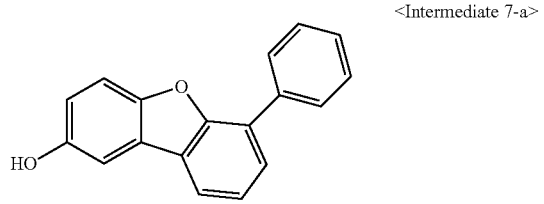 [SMILES: Oc1ccc2oc3c(-c4ccccc4)cccc3c2c1]
<Intermediate 7-a>

The same procedure was conducted as in Synthesis Examples 6-(1) to 6-(4), with the exception of using 2-fluorobiphenyl instead of 3-fluorobiphenyl in Synthesis Example 6-(1), to synthesize <Intermediate 7-a>. (12 g, 48%)

Synthesis Example 7-(2)

Synthesis of Intermediate 7-b

Intermediate 7-b was synthesized as illustrated in the following Reaction Scheme 44:

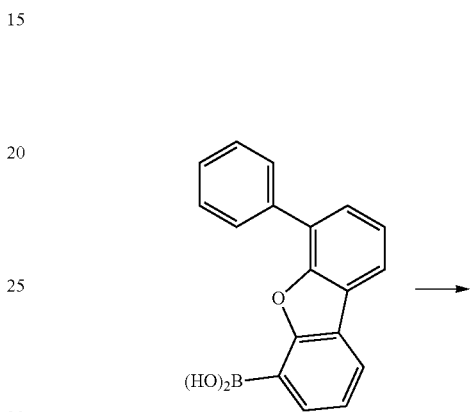

The same procedure was conducted as in Synthesis Example 2-(5), with the exception of using <Intermediate 7-a> instead of <Intermediate 2-d>, to synthesize <Intermediate 7-b>. (16 g, 50.3%)

Synthesis Example 7-(3)

Synthesis of Intermediate 7-c

Intermediate 7-c was synthesized as illustrated in the following Reaction Scheme 45:

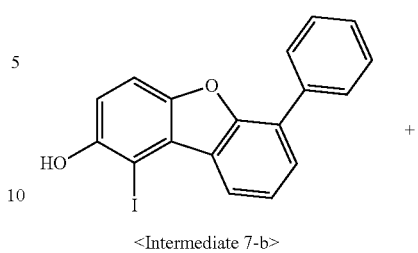

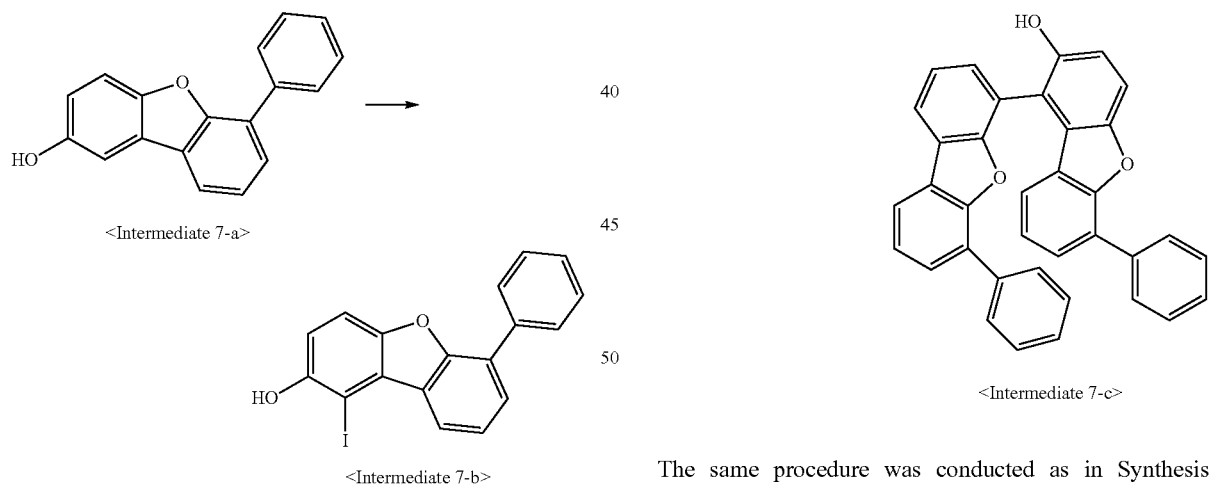

The same procedure was conducted as in Synthesis Example 1-(5), with the exception of using (6-phenyldibenzofuran-4-yl)boronic acid and <Intermediate 7-b> instead of <Intermediate 1-d> and 1-iodo 2-dibenzofuranol, respectively, to synthesize <Intermediate 7-c>. (14.5 g, 52%)

Synthesis Example 7-(4)

Synthesis of Intermediate 7-d

Intermediate 7-d was synthesized as illustrated in the following Reaction Scheme 6 to 11:

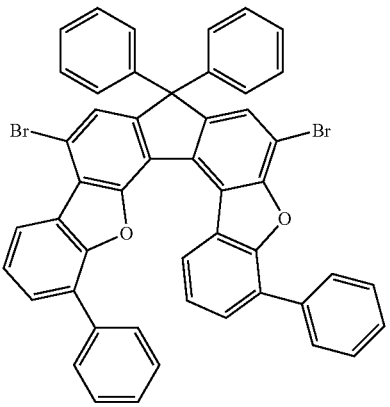

<Intermediate 7-d>

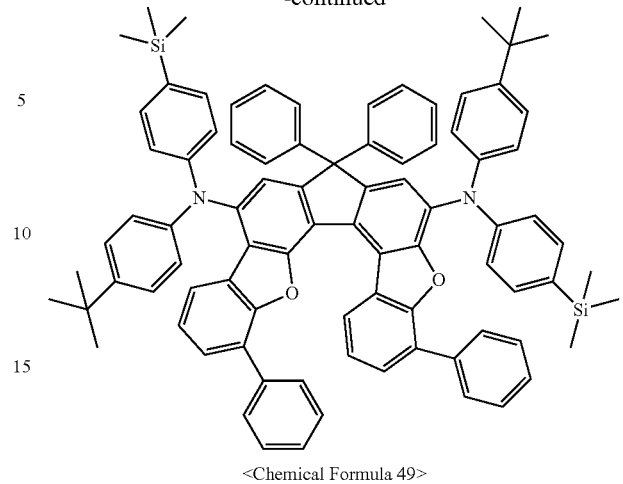

<Chemical Formula 49>

The same procedure was conducted as in Synthesis Examples 1-(6) to 1-(11), with the exception of using <Intermediate 7-c> instead of <Intermediate 1-e> in Synthesis Example 1-(6), to synthesize <Intermediate 7-d>. (16.1 g, 71%)

Synthesis Example 7-(5)

Synthesis of Compound of Chemical Formula 49

The compound of Chemical Formula 49 was synthesized as illustrated in the following Reaction Scheme 46:

<Reaction Scheme 46>

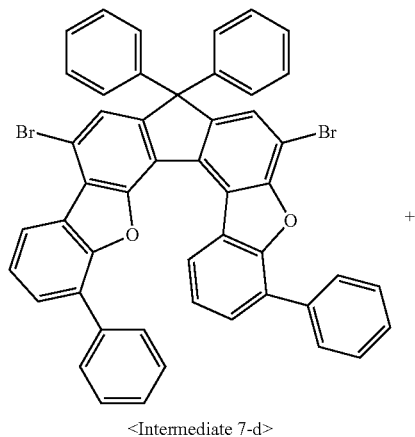

<Intermediate 7-d>

+

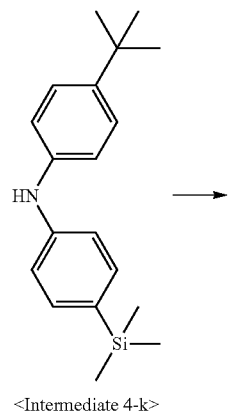

<Intermediate 4-k>

The same procedure was conducted as in Synthesis Example 4-(12), with the exception of using <Intermediate 7-d> instead of <Intermediate 4-j>, to synthesize the compound of <Chemical Formula 49>. (14 g, 62.2%)

MS (MALDI-TOF):m/z 1241.58 [M$^+$]

Examples 1 to 7

Fabrication of Organic Light-Emitting Diode

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of DNTPD (700 Å) and α-NPD (300 Å) in that order. A light-emitting layer (250 Å) was formed of a mixture including [BH1] and 3% of each of the compounds shown in Table 1 according to the present disclosure. Then, [Chemical Formula E-1] and [Chemical Formula E-2] were deposited at a ratio of 1:1 to form an electron transport layer 300 Å thick, on which an electron injection layer of [Chemical Formula E-1] (5 Å thick) was formed and then covered with an Al layer (1000 Å) to fabricate an organic light-emitting diode. The organic light-emitting diodes thus obtained were measured at 0.4 mA for luminescence properties:

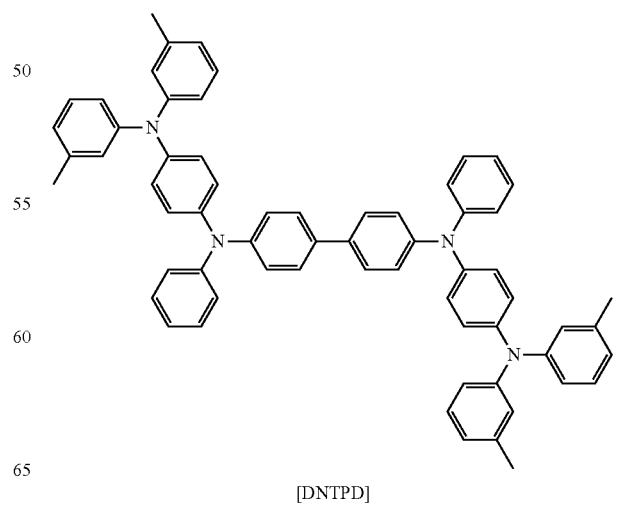

[DNTPD]

was used, instead of the dopant compound used in Example 1. The luminescence of the organic light-emitting diode was measured at 0.4 mA. The structure of [BD1] is as follows:

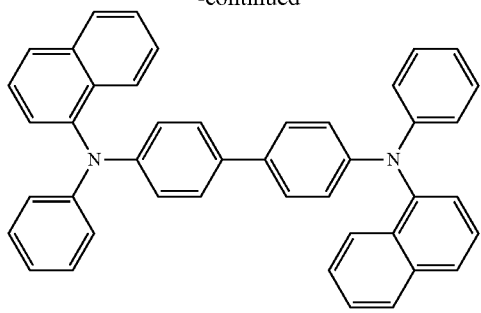

[α-NPD]

[Chemical Formula E-1]

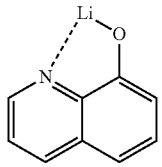

[Chemical Formula E-2]

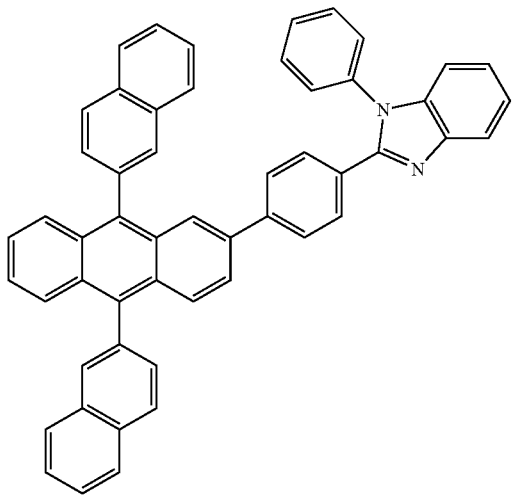

[BH1]

[BD1]

The organic light-emitting diodes fabricated in Examples 1 to 7 and Comparative Example 1 were measured for voltage, luminance, color coordinates, and lifespan, and the results are summarized in Table 1, below.

TABLE 1

| Ex. No. | Dopant (Chemical Formula) | Volt.(V) | Q.E(%) | CIEx | CIEy | T97 (hr) |
|---|---|---|---|---|---|---|
| C. 1 | BD1 | 3.8 | 7.6 | 0.141 | 0.125 | 80 |
| 1 | Chemical Formula 10 | 3.6 | 8.9 | 0.138 | 0.104 | 110 |
| 2 | Chemical Formula 14 | 3.7 | 8.5 | 0.137 | 0.110 | 107 |
| 3 | Chemical Formula 15 | 3.6 | 8.8 | 0.138 | 0.107 | 116 |
| 4 | Chemical Formula 20 | 3.7 | 8.7 | 0.139 | 0.099 | 106 |
| 5 | Chemical Formula 24 | 3.6 | 8.6 | 0.138 | 0.095 | 103 |
| 6 | Chemical Formula 44 | 3.7 | 8.9 | 0.139 | 0.097 | 107 |
| 7 | Chemical Formula 49 | 3.7 | 8.7 | 0.138 | 0.101 | 111 |

As is understood from the data of Table 1, the organic light-emitting diodes of Examples 1 to 7 exhibited outstanding quantum efficiency and longevity, compared to that of Comparative Example 1, which corresponds to a compound having no substituents on the aromatic rings of $A_1$ to $A_4$ of Chemical Formula A, thereby demonstrating their high applicability to organic electroluminescence devices.

INDUSTRIAL APPLICABILITY

Available for use in organic light-emitting devices having excellent properties, such as high light emission efficiency and long lifespan, the novel amine compound according to the present disclosure is industrially applicable.

Comparative Example 1

An organic light-emitting diode was fabricated in the same manner as in Example 1, with the exception that [BD1]

The invention claimed is:

1. An amine compound represented by the following Chemical Formula A-1:

[Chemical Formula A-1]

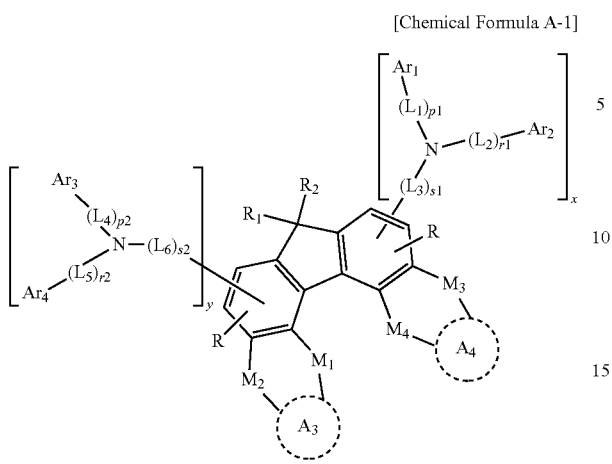

wherein,

A$_3$ and A$_4$, which are the same or different, are each independently a substituted or unsubstituted aromatic hydrocarbon ring of 6 to 50 carbon atoms;

two adjacent carbon atoms within the aromatic ring of A$_3$ are linked to M$_1$ and M$_2$, respectively, in order to form a 5-membered, fused ring;

two adjacent carbon atoms within the aromatic ring of A$_4$ are linked to M$_3$ and M$_4$, respectively, in order to form a 5-membered, fused ring;

linkers L$_1$ to L$_6$, which are the same or different, are each independently selected from among a single bond and a substituted or unsubstituted arylene of 6 to 60 carbon atoms;

at least one of the aromatic rings of A$_3$ to A$_4$ has one substituent selected from among a substituted or unsubstituted alkyl of 1 to 30 carbon atoms, a substituted or unsubstituted cycloalkyl of 1 to 30 carbon atoms, a substituted or unsubstituted aryl of 6 to 50 carbon atoms, and a halogen selected from F, Cl, Br, and I;

M$_1$ to M$_4$, which are the same or different, are each independently a single bond, O, S, or CR$_3$R$_4$, with a proviso that one of M$_1$ and M$_2$ is a single bond, and one of M$_3$ and M$_4$ is a single bond;

substituents R$_1$ to R$_4$ and Ar$_1$ to Ar$_4$, which are the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 5 to 30 carbon atoms, a cyano, a nitro, and a halogen;

in the alterative for R$_1$ and R$_2$, R$_1$ and R$_2$ are connected to each other to form a mono- or polycyclic aliphatic or aromatic ring which may bear at least one heteroatom selected from among N, O, P, Si, and S as a ring member;

p1 and p2, r1 and r2, and s1 and s2 are each independently an integer of 1 to 3 and when any of them is 2 or greater, the corresponding linkers L$_1$ to L$_6$ are the same or different;

x is an integer of 1;

y is an integer of 1;

in the alternative for Ar$_1$ and Ar$_4$, Ar$_1$ and Ar$_2$ are connected to each other to form a ring and/or Ar$_3$ and Ar$_4$ are connected to each other to form a ring;;

substituents R's which are the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 5 to 30 carbon atoms, a cyano, a nitro, and a halogen;

Chemical Formula A-1 excludes compounds in which A$_3$ and A$_4$ each have one phenyl group and R$_1$ and R$_2$ form a ring with each other; and the term "substituted" in the expression "substituted or unsubstituted" used for Chemical Formula A means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an aryl of 6 to 24 carbon atoms, an arylalkyl of 6 to 24 carbon atoms, an alkylsilyl of 1 to 24 carbon atoms, and an arylsilyl of 6 to 24 carbon atoms.

2. The amine compound of claim 1, wherein the substituted or unsubstituted aromatic hydrocarbon ring of 6 to 50 carbon atoms in A$_2$ and A$_4$, which are the same or different, are each independently one selected from among [Structural Formula 10] to [Structural Formula 21]:

[Structural Formula 10]

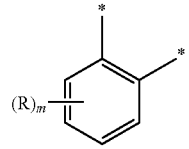

[Structural Formula 11]

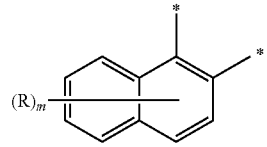

[Structural Formula 12]

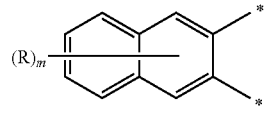

[Structural Formula 13]

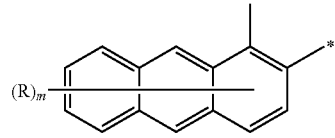

[Structural Formula 14]

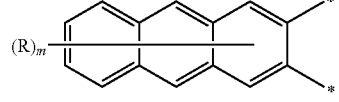

-continued

[Structural Formula 15]

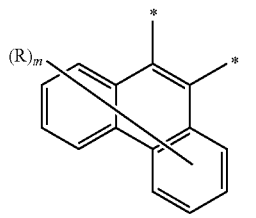

[Structural Formula 16]

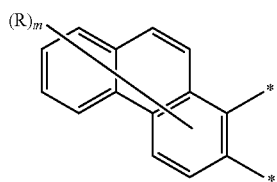

[Structural Formula 17]

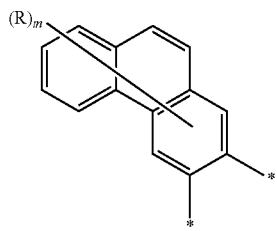

[Structural Formula 18]

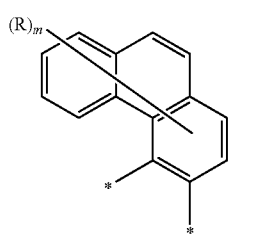

[Structural Formula 19]

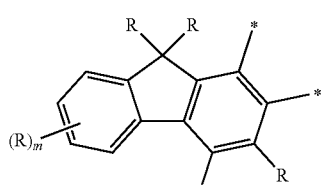

[Structural Formula 20]

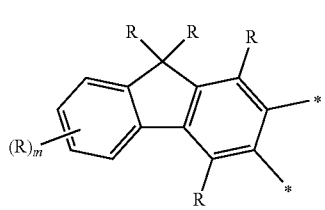

[Structural Formula 21]

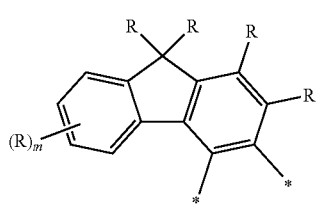

wherein,

"_*" denotes a bonding site linked to $M_1$ to $M_4$ to form a fuse ring; and

R is as defined for $R_1$ and $R_2$, and m is an integer of 1 to 8 wherein when m is 2 or greater or when R exists as multiple radicals, the resulting R's may be the same or different.

3. The amine compound of claim 1, wherein the linkers $L_1$ to $L_6$ are each a single bond or a substituted or unsubstituted arylene of 6 to 20 carbon atoms.

4. The amine compound of claim 3, wherein the linkers $L_1$ to $L_6$ are each a single bond or one selected from among the following [Structural Formula 22], [Structural Formula 23], [Structural Formula 25], [Structural Formula 27], [Structural Formula 28], and [Structural Formula 30], p1 and p2, r1 and r2, and s1 and s2 are each 1 or 2, and x is 1:

[Structural Formula 22]

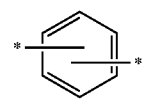

[Structural Formula 23]

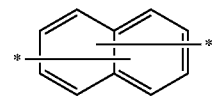

[Structural Formula 25]

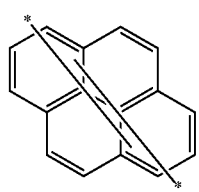

[Structural Formula 27]

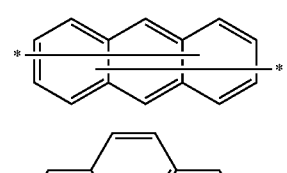

[Structural Formula 28]

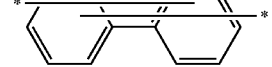

[Structural Formula 30]

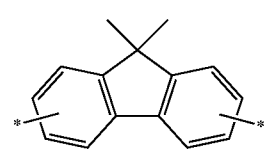

wherein, each of unsubstituted carbon atoms of the aromatic ring moiety may be bound with a hydrogen atom or a deuterium atom.

5. The amine compound of claim 1, wherein the substituents $R_1$ to $R_4$, and $Ar_1$ to $Ar_4$, which are the same or different, are each independently one selected from among a hydrogen atom, a deuterium atom, a substituted or unsubstituted aryl of 6 to 20 carbon atoms, a substituted or unsubstituted cycloalkyl of 3 to 30 carbon atoms, and a substituted or unsubstituted heteroaryl of 2 to 20 carbon atoms bearing at least one selected from among O, N, S, and Si as a heteroatom, a cyano, and a halogen.

6. The amine compound of claim 1, wherein the amine compound is one selected from among the compounds represented by [Chemical Formula 1] to [Chemical Formula 15], [Chemical Formula 17], [Chemical Formula 19] to [Chemical Formula 30],

[Chemical Formula 32], [Chemical Formula 34] to [Chemical Formula 47], and [Chemical Formula 49] to [Chemical Formula 51]:
<Chemical Formula 1>
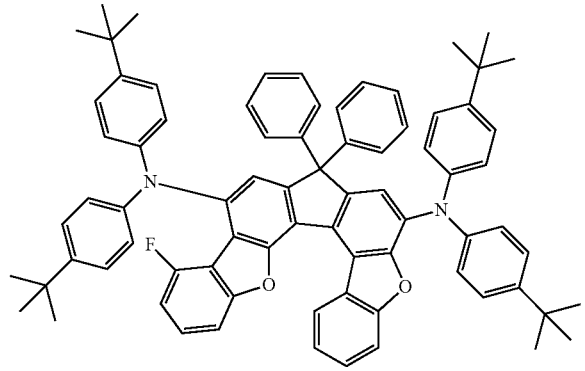
<Chemical Formula 2>
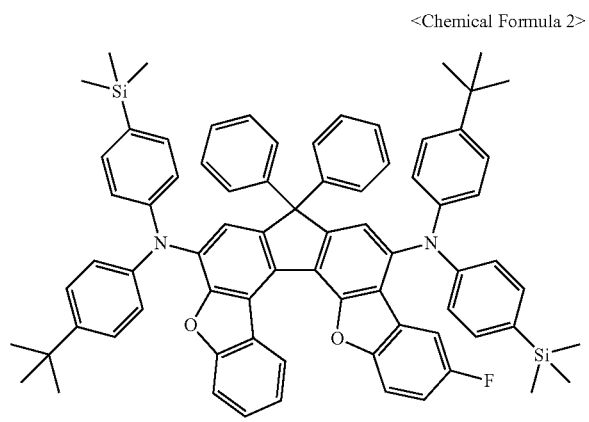
<Chemical Formula 3>
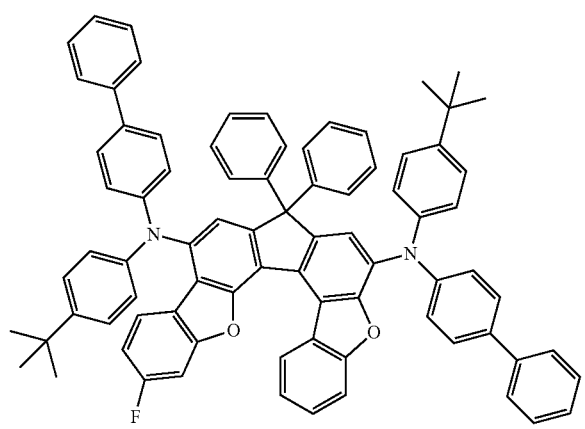
<Chemical Formula 4>
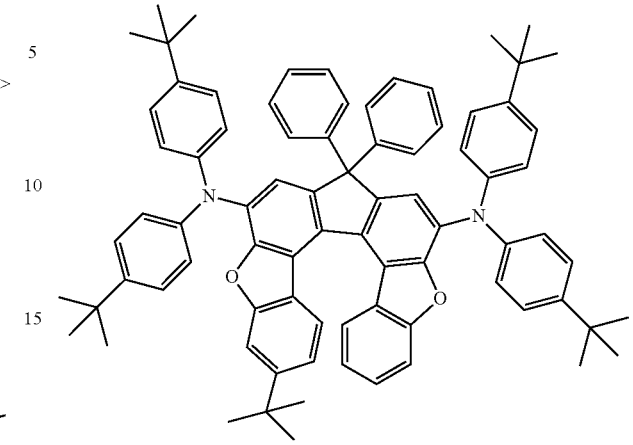
<Chemical Formula 5>
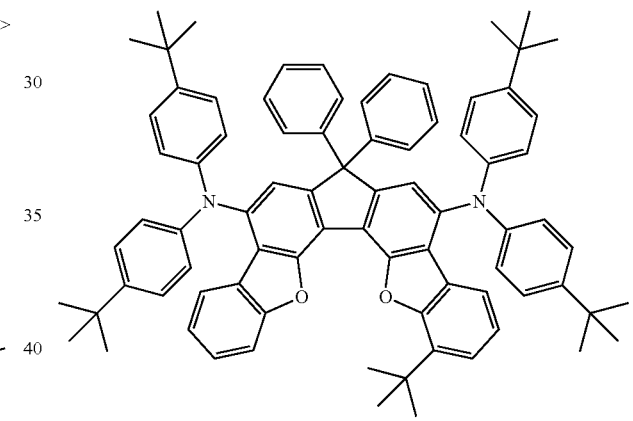
<Chemical Formula 6>
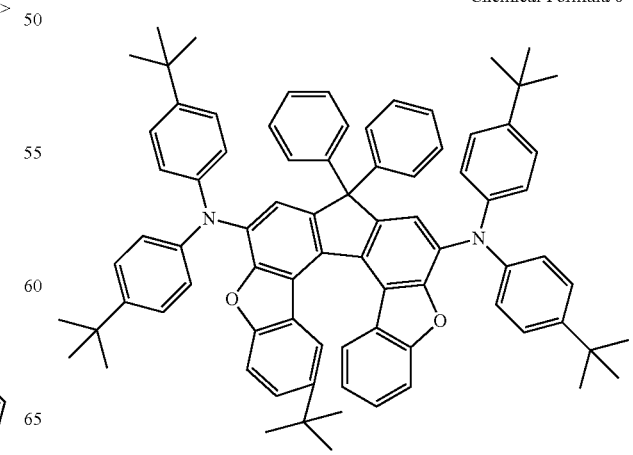

<Chemical Formula 7>
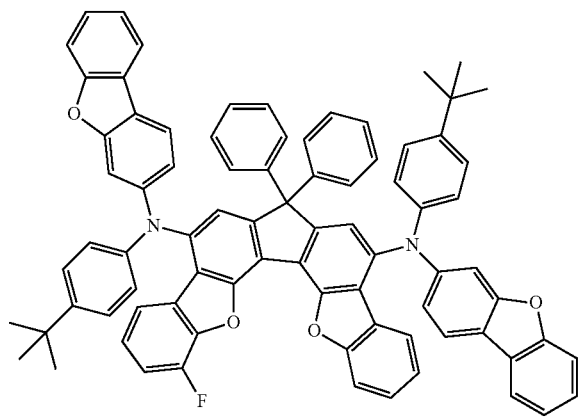
<Chemical Formula 8>
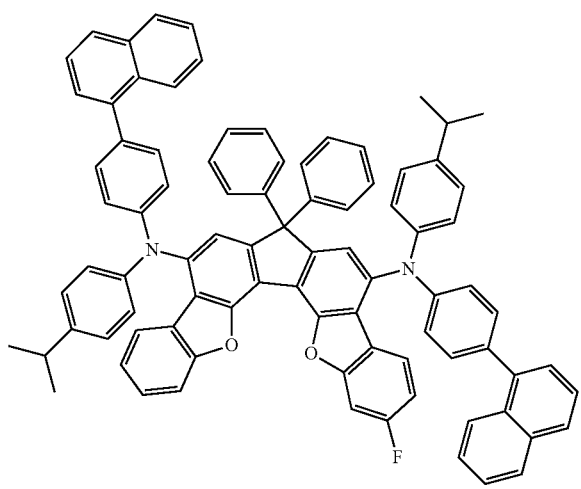
<Chemical Formula 9>
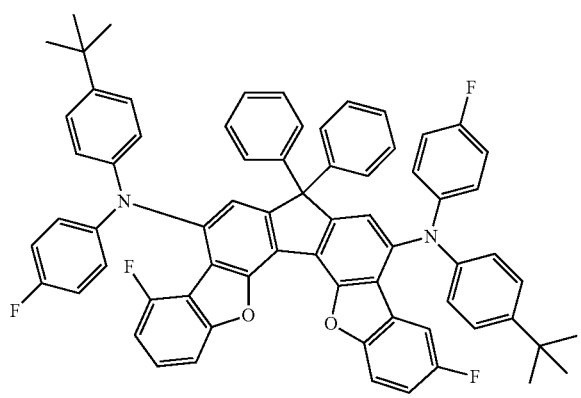
<Chemical Formula 10>
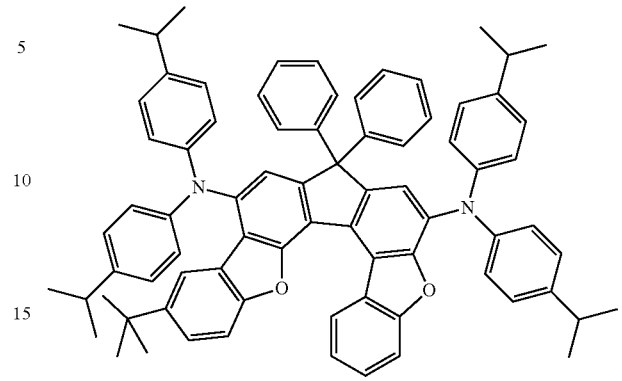
<Chemical Formula 11>
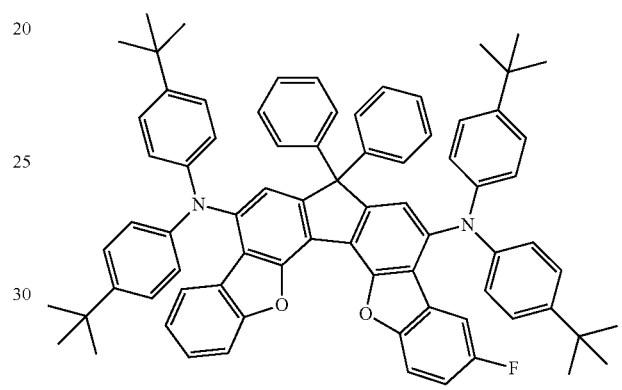
<Chemical Formula 12>
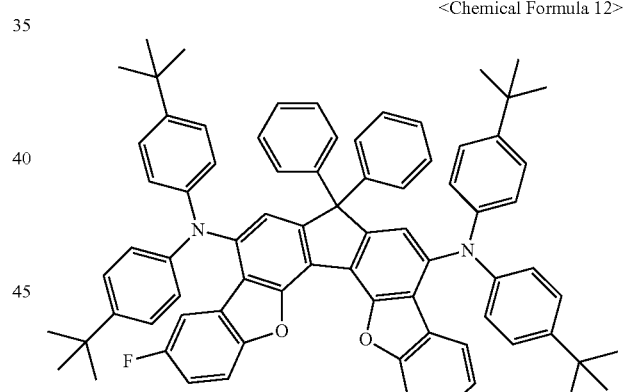
<Chemical Formula 13>
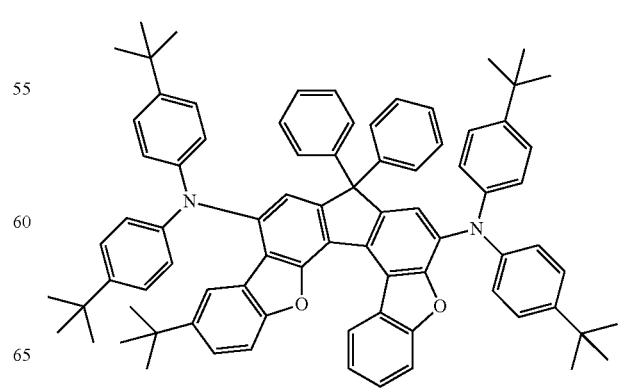

<Chemical Formula 14>
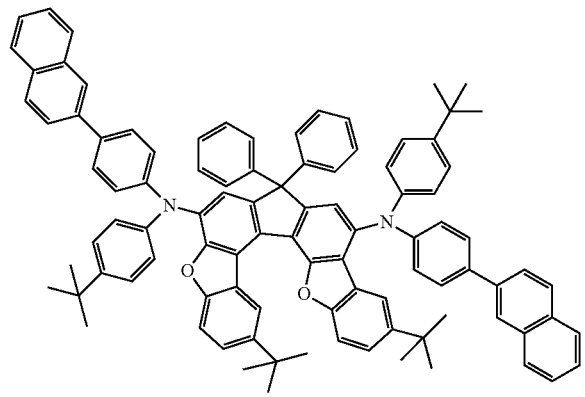
<Chemical Formula 19>
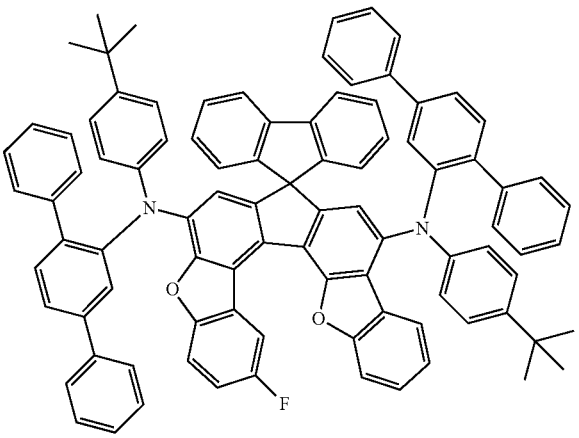
<Chemical Formula 15>
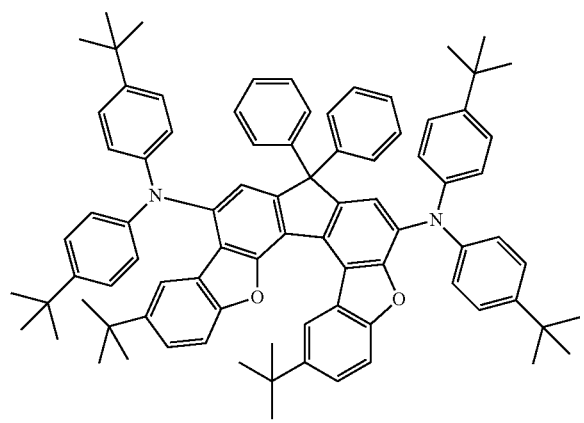
<Chemical Formula 20>
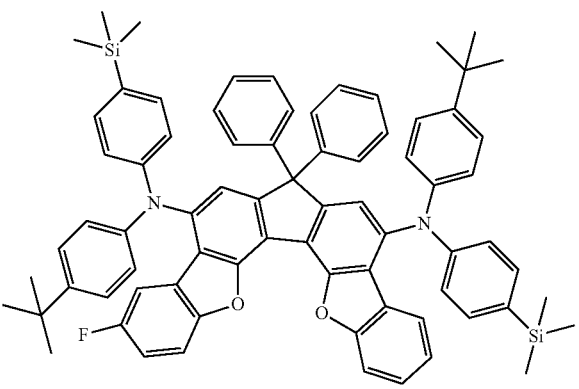
<Chemical Formula 17>
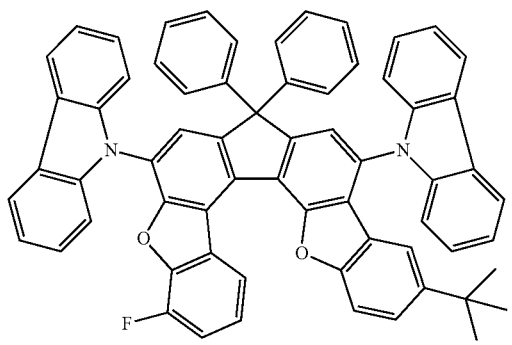
<Chemical Formula 21>
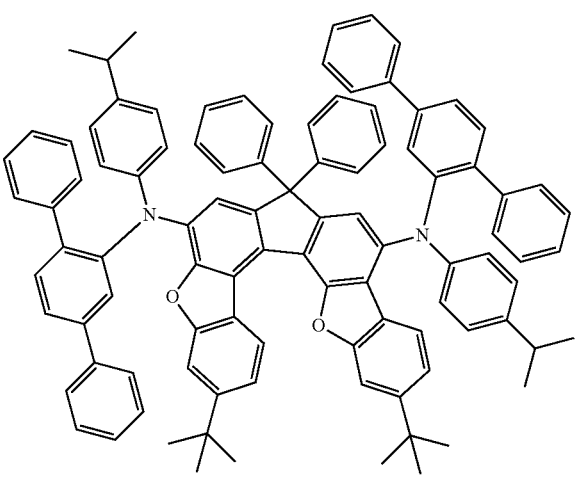

<Chemical Formula 22>
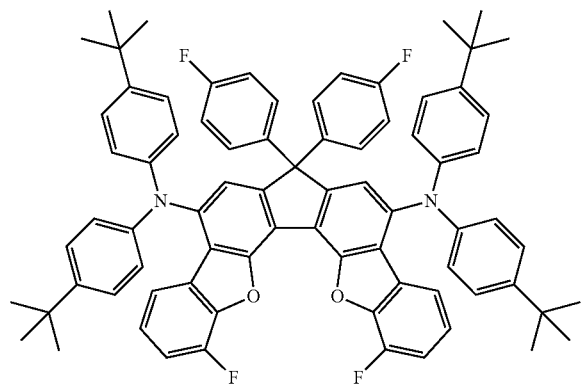
<Chemical Formula 23>
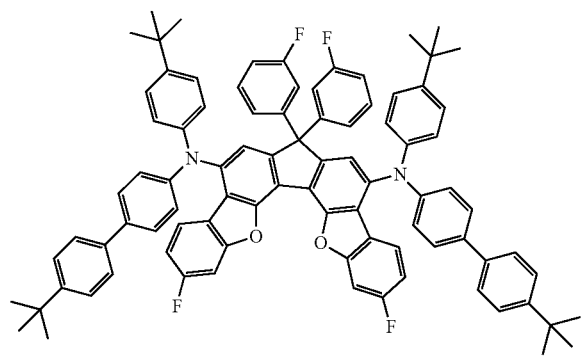
<Chemical Formula 24>
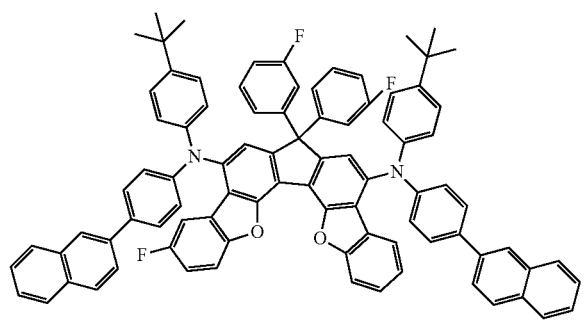
<Chemical Formula 25>
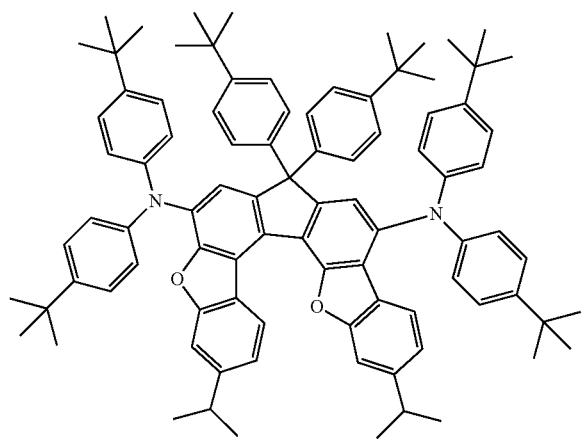
<Chemical Formula 26>
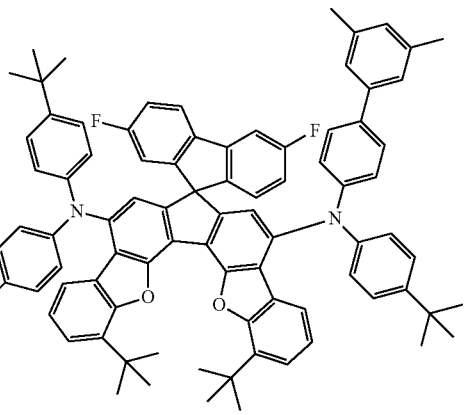
<Chemical Formula 27>
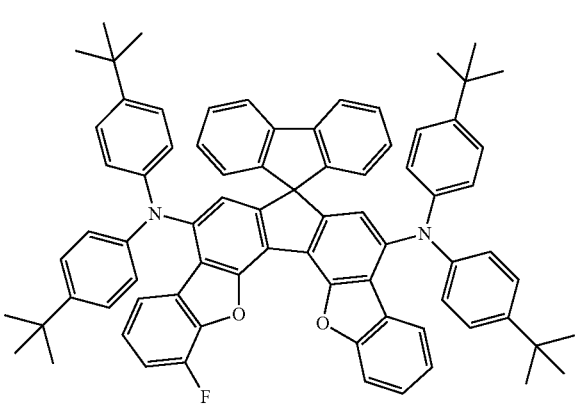
<Chemical Formula 28>
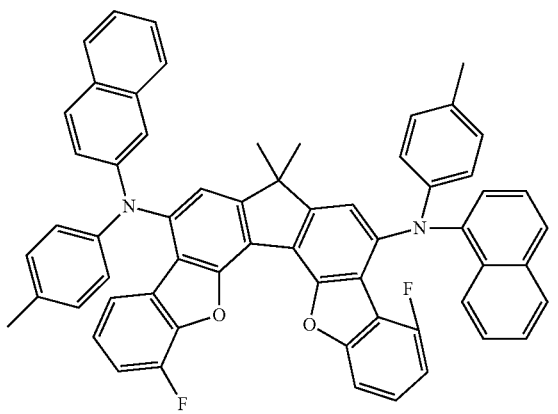
<Chemical Formula 29>
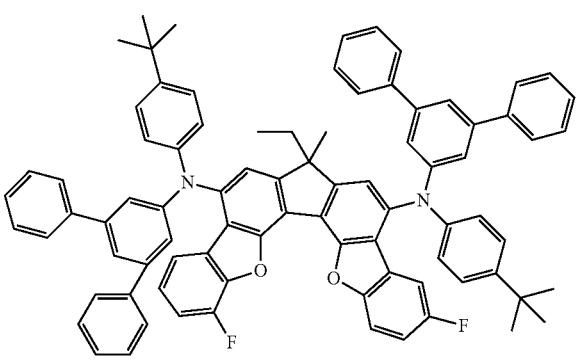

<Chemical Formula 30>
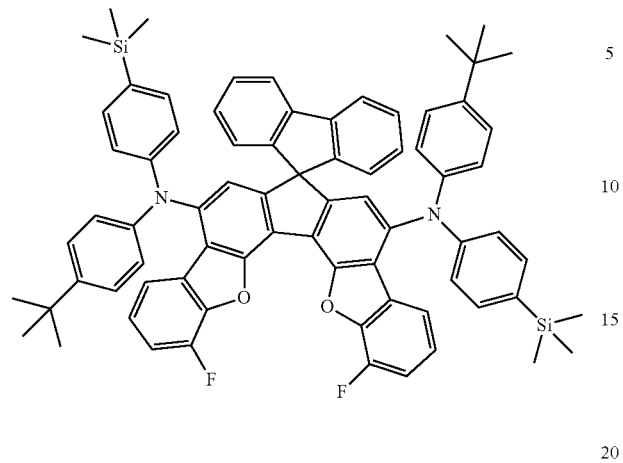
<Chemical Formula 32>
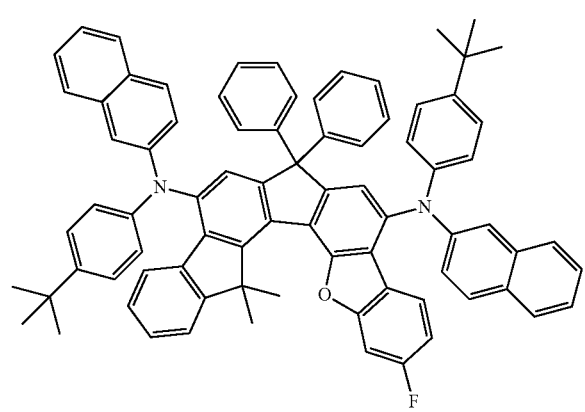
<Chemical Formula 34>
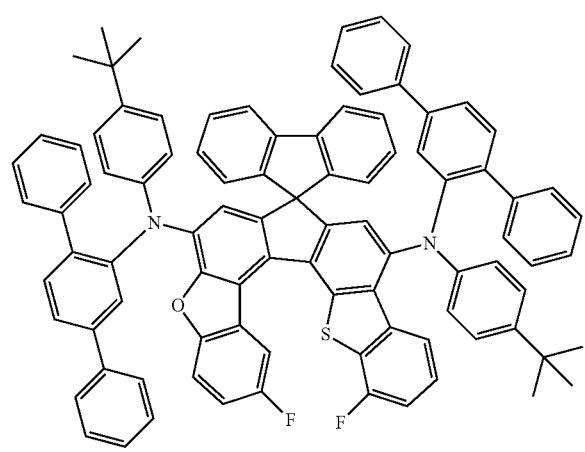
<Chemical Formula 35>
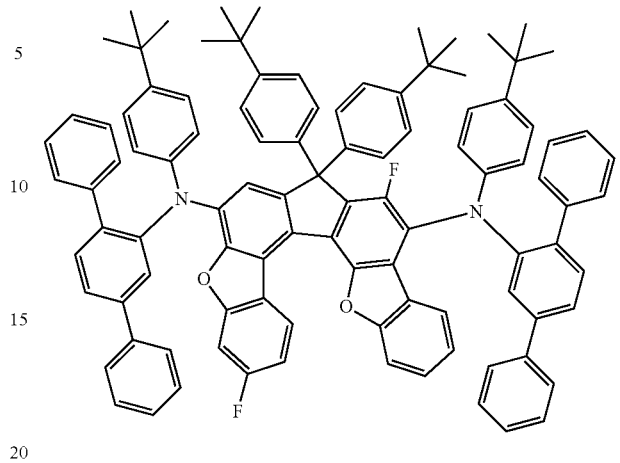
<Chemical Formula 36>
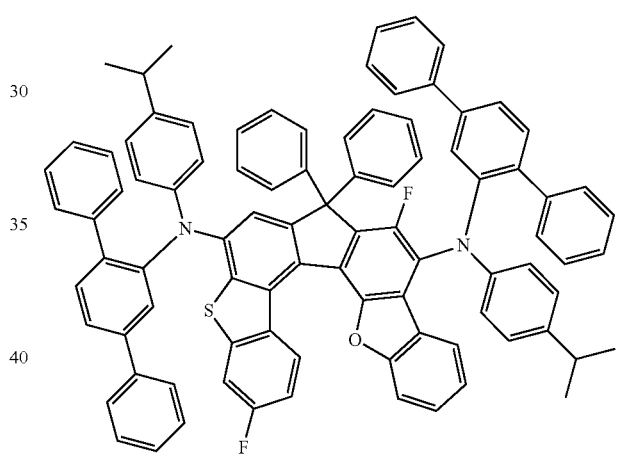
<Chemical Formula 37>
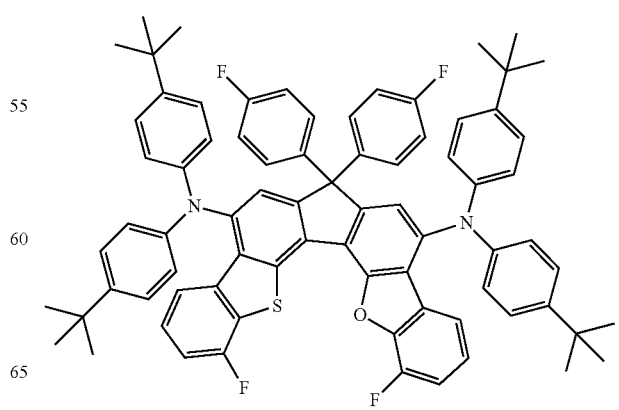

101
-continued
<Chemical Formula 38>
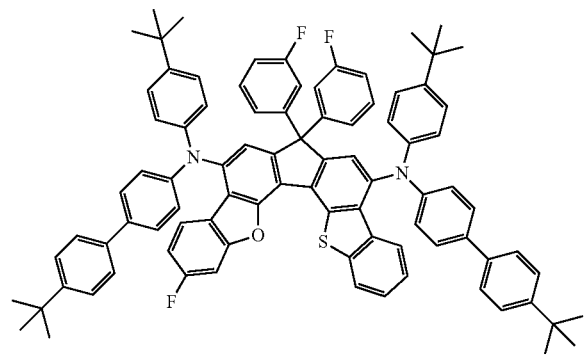
<Chemical Formula 39>
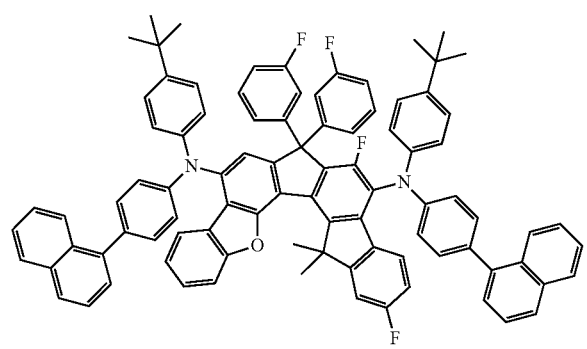
<Chemical Formula 40>
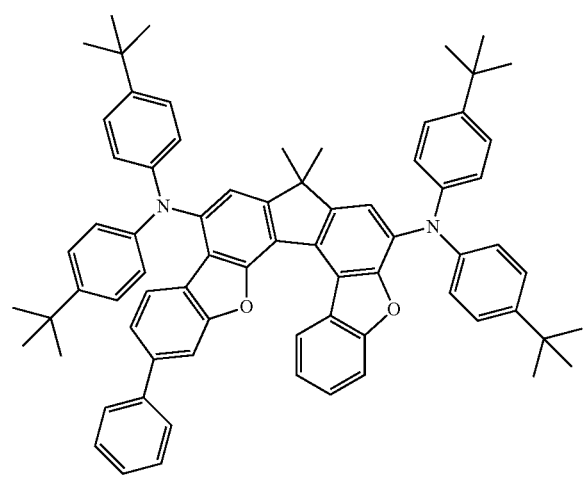
102
-continued
<Chemical Formula 41>
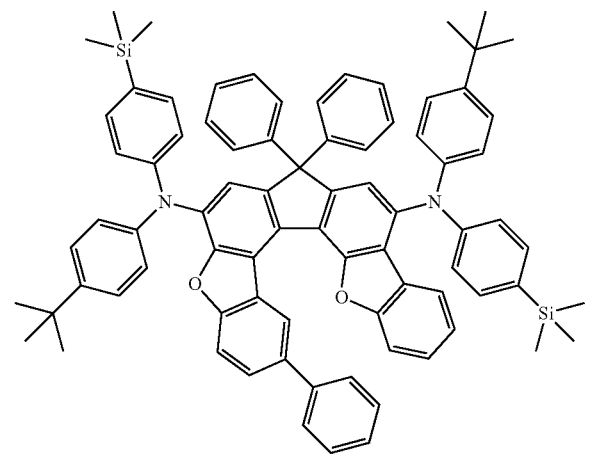
<Chemical Formula 42>
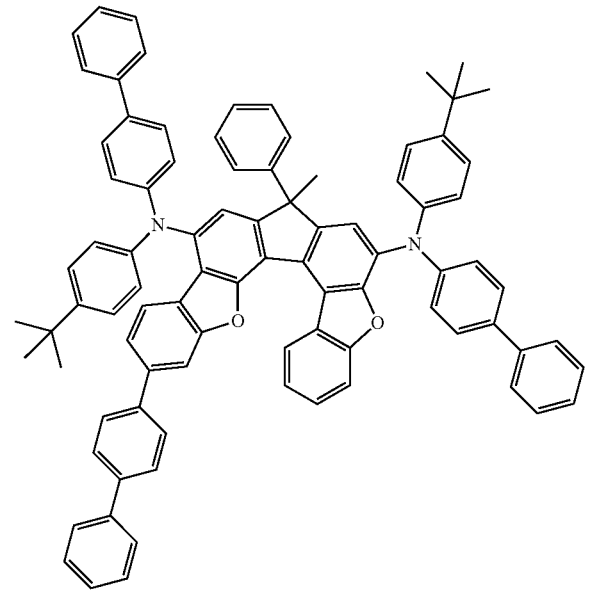
<Chemical Formula 43>
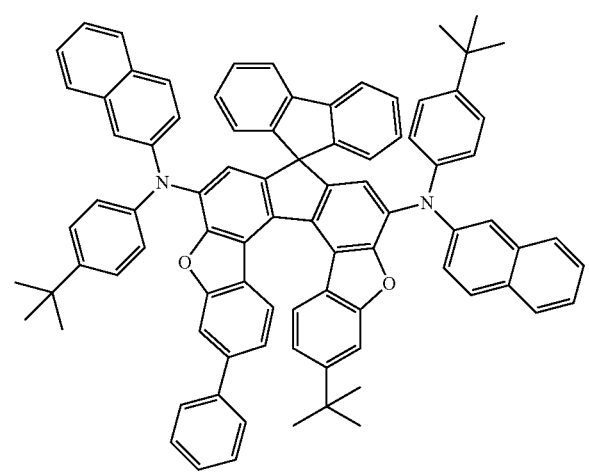

<Chemical Formula 44>
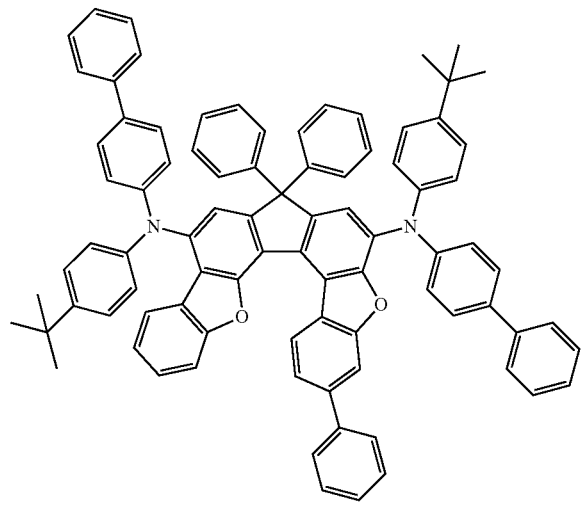
<Chemical Formula 45>
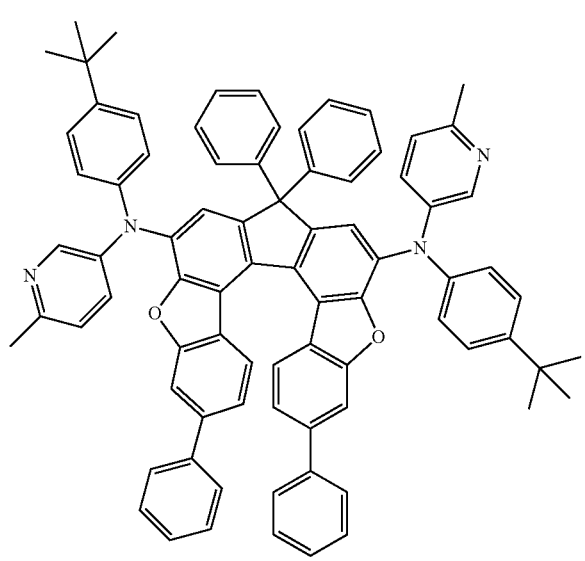
<Chemical Formula 46>
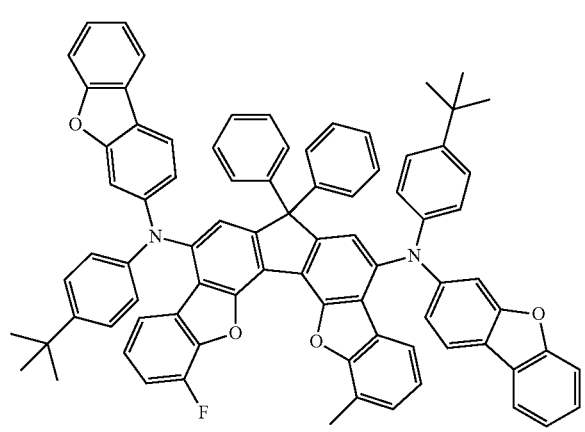
<Chemical Formula 47>
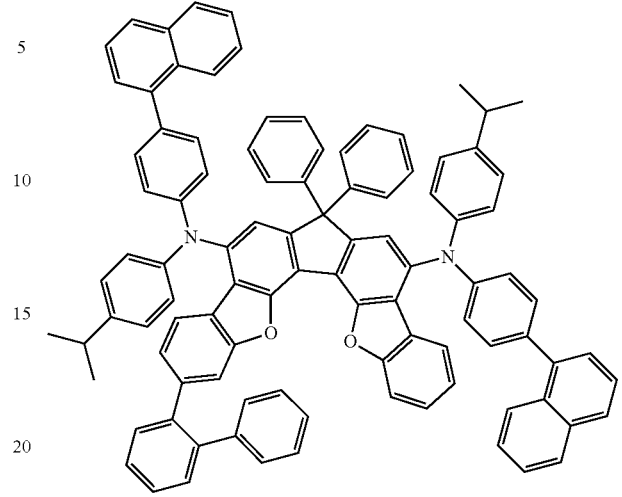
<Chemical Formula 49>
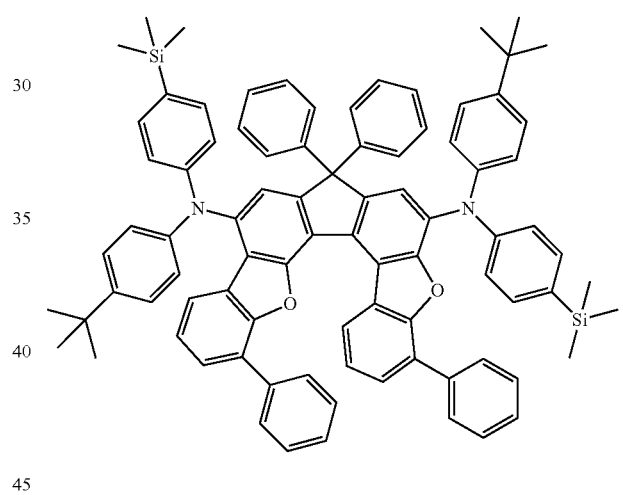
<Chemical Formula 50>
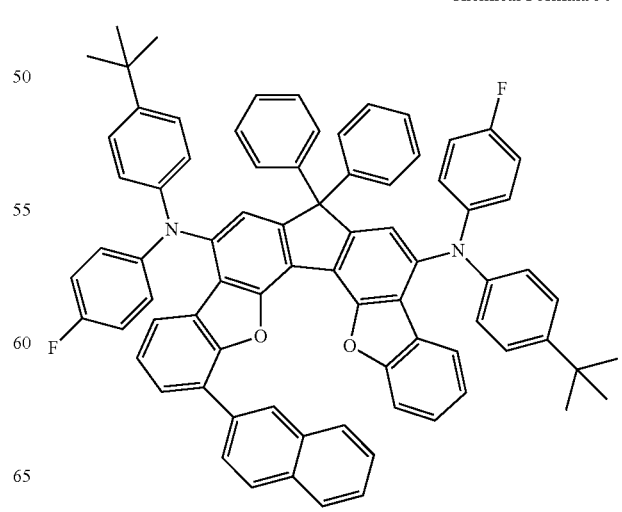

105

-continued

<Chemical Formula 51>

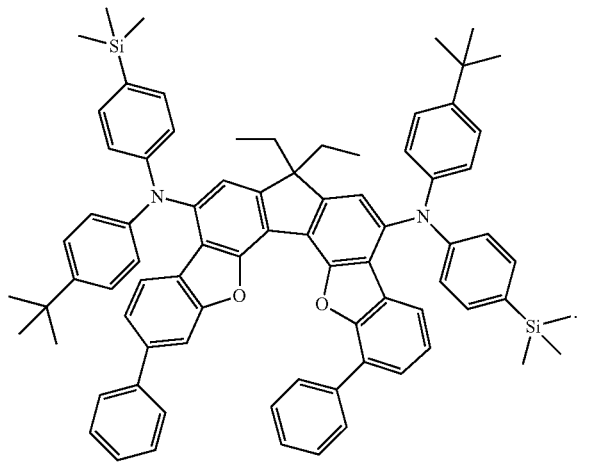

7. An organic light-emitting diode, comprising a first electrode; a second electrode facing the first electrode, and a light-emitting layer interposed between the first electrode and the second electrode, wherein the light-emitting layer comprises at least one of the amine compounds of claim 1.

8. The organic light-emitting diode of claim 7, further comprising at least one selected from among a hole injection layer, a hole transport layer, a functional layer capable of both hole injection and hole transport, an electron transport layer, and an electron injection layer, in addition to the light-emitting layer.

9. The organic light-emitting diode of claim 7, wherein the light emitting layer includes a host and a dopant wherein the amine compound represented by Chemical Formula A is used as the dopant.

10. The organic light-emitting diode of claim 8, wherein at least one of the layers is formed using a deposition process or a solution process.

11. The organic light-emitting diode of claim 7, wherein the organic light-emitting diode is used for a device selected from among a flat display device, a flexible display device, a monochrome or grayscale flat illumination device, and a monochrome or grayscale flexible illumination device.

* * * * *